(12) United States Patent
Hadd et al.

(10) Patent No.: US 7,795,228 B2
(45) Date of Patent: Sep. 14, 2010

US007795228B2

(54) SPIROHETEROCYCLIC GLYCOSIDES AND METHODS OF USE

(75) Inventors: Michael J. Hadd, San Diego, CA (US); Yuanwei Chen, North Haven, CT (US); Yan Feng, Shanghai (CN); Sengen Sen, San Diego, CA (US); Brian Seed, Derry, NH (US)

(73) Assignee: Theracos, Inc., Sunnyvale, CA (US)

( * ) Notice: Subject to any disclaimer, the term of this patent is extended or adjusted under 35 U.S.C. 154(b) by 184 days.

(21) Appl. No.: 11/964,493

(22) Filed: Dec. 26, 2007

(65) Prior Publication Data

US 2008/0182802 A1 Jul. 31, 2008

Related U.S. Application Data

(60) Provisional application No. 60/877,904, filed on Dec. 28, 2006.

(51) Int. Cl.
*A01N 43/04* (2006.01)
*C07H 1/00* (2006.01)
*C07H 3/00* (2006.01)
*C08B 37/00* (2006.01)

(52) U.S. Cl. .................................. 514/23; 536/1.11

(58) Field of Classification Search ....................... None
See application file for complete search history.

(56) References Cited

U.S. PATENT DOCUMENTS

| | | | |
|---|---|---|---|
| 5,663,377 | A | 9/1997 | Curley, Jr. et al. |
| 6,069,238 | A | 5/2000 | Hitchcock et al. |
| 6,414,126 | B1 | 7/2002 | Ellsworth et al. |
| 7,094,763 | B2 | 8/2006 | Rybczynski et al. |
| 2002/0111315 | A1 | 8/2002 | Washburn et al. |
| 2003/0114390 | A1 | 6/2003 | Washburn et al. |
| 2004/0138148 | A1 | 7/2004 | Fushimi et al. |
| 2004/0138439 | A1 | 7/2004 | Deshpande et al. |
| 2004/0259819 | A1 | 12/2004 | Frick et al. |
| 2005/0014704 | A1 | 1/2005 | Frick et al. |
| 2005/0032712 | A1 | 2/2005 | Urbanski |
| 2005/0037980 | A1 | 2/2005 | Rybczynski et al. |
| 2005/0187168 | A1 | 8/2005 | Eickelmann et al. |
| 2005/0209166 | A1 | 9/2005 | Eckhardt et al. |
| 2005/0209309 | A1 | 9/2005 | Sato et al. |
| 2005/0233988 | A1 | 10/2005 | Nomura et al. |
| 2006/0009400 | A1 | 1/2006 | Eckhardt et al. |
| 2006/0019948 | A1 | 1/2006 | Eckhardt et al. |
| 2006/0063722 | A1 | 3/2006 | Washburn et al. |
| 2006/0074031 | A1 | 4/2006 | Eckhardt et al. |
| 2006/0122126 | A1 | 6/2006 | Imamura et al. |
| 2006/0189548 | A1 | 8/2006 | Himmelsbach et al. |
| 2006/0234953 | A1 | 10/2006 | Himmelsbach et al. |
| 2006/0235062 | A1 | 10/2006 | Neogi et al. |
| 2006/0258749 | A1 | 11/2006 | Eckhardt et al. |
| 2007/0004648 | A1 | 1/2007 | Himmelsbach et al. |
| 2007/0027092 | A1 | 2/2007 | Himmelsbach et al. |
| 2007/0049537 | A1 | 3/2007 | Eckhardt et al. |
| 2007/0185197 | A1 | 8/2007 | Fujikura et al. |
| 2007/0197450 | A1 | 8/2007 | Fushimi et al. |
| 2007/0275907 | A1 | 11/2007 | Chen et al. |
| 2008/0027014 | A1 | 1/2008 | Nomura et al. |
| 2008/0132563 | A1 | 6/2008 | Kakinuma et al. |
| 2008/0139484 | A1 | 6/2008 | Teranishi et al. |

FOREIGN PATENT DOCUMENTS

| | | |
|---|---|---|
| EP | 1 783 110 A1 | 5/2007 |
| EP | 1 803 721 A1 | 7/2007 |
| EP | 1 852 439 A1 | 11/2007 |
| WO | WO 98/31697 A1 | 7/1998 |
| WO | WO 2006/110654 A1 | 10/2006 |

OTHER PUBLICATIONS

Stella, "Prodrugs as Therapeutics", Expert Opinion Ther. Patents (2004) 14(3), pp. 277-280.*
International Search Report mailed on Aug. 1, 2008, for PCT Application No. PCT/US07/88905, filed on Dec. 27, 2007, 2 pages.
Isaji, M., "Sodium-Glucose Cotransporter Inhibitors for Diabetes," *Current Opinion in Investigational Drugs*, 2007, vol. 8, No. 4, pp. 285-292.
Kuribayashi, T. et al., "C-Glycosylated Diphenylmethanes and benzophenones: The Stille Coupling Reaction of C-Glycosylated Aryl Tins With Benzyl Bromides and Acid Chlorides," *J. Carbohydrate Chemistry*, 1999, vol. 18, No. 4, pp. 393-401.
Raj, A.A. et al., "A Novel Entry Into a New Class of Spiroheterocyclic Framework: Regioselective Synthesis of Dispiro[oxindolecyclohexanone]-Pyrrolidines and Dispiro[oxindolehexahydroindazole]pyrrolidines," *Tetrahedron*, 2001, vol. 57, pp. 10293-10298.

* cited by examiner

*Primary Examiner*—Traviss C McIntosh, III
(74) *Attorney, Agent, or Firm*—Townsend and Townsend and Crew LLP

(57) ABSTRACT

Provided are compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions which are affected by SGLT inhibition.

41 Claims, 18 Drawing Sheets

*Scheme IX*

Scheme X

*Scheme 1A*

*Scheme 1B*

*Scheme 2A*

*Scheme 2B*

*Scheme 3A*

*Scheme 3B*

Scheme 4

*Scheme 5*

*Scheme 6*

*Scheme 7*

Scheme 8

Scheme 9

Scheme 10

Scheme 11

SPIROHETEROCYCLIC GLYCOSIDES AND METHODS OF USE

CROSS-REFERENCES TO RELATED APPLICATIONS

This application claims the benefit of U.S. Provisional Application Ser. No. 60/877,904 filed Dec. 28, 2006, the disclosure of which is incorporated herein by reference.

STATEMENT AS TO RIGHTS TO INVENTIONS MADE UNDER FEDERALLY SPONSORED RESEARCH OR DEVELOPMENT

NOT APPLICABLE

BACKGROUND OF THE INVENTION

According to the World Health Organization, approximately 150 million people worldwide have diabetes mellitus. The two principle forms of diabetes are type 1 diabetes, in which the pancreas fails to produce insulin, and type 2 diabetes, in which the body fails to respond properly to the insulin produced (insulin resistance). Accounting for about 90% of all diabetes cases, type 2 diabetes is by far the most common. In both types of diabetes, the absence of insulin action or proper response to insulin results in elevated levels of serum glucose (hyperglycemia). Serious complications associated with diabetes include retinopathy (leading to visual impairment or blindness), cardiovascular disease, nephropathy, neuropathy, ulcers and diabetic foot disease.

Individuals with type 1 diabetes currently require insulin therapy. While in many cases type 2 diabetes can be managed with diet and exercise, drug intervention also frequently is required. Besides insulin, which is needed by about one-third of patients with type 2 diabetes, current antidiabetic therapies include biguanides (which decrease glucose production in the liver and increase sensitivity to insulin), sulfonylureas and meglitinides (which stimulate insulin production), alpha-glucosidase inhibitors (which slow starch absorption and glucose production), and thiazolidinediones (which increase insulin sensitivity). These medicines are often used in combination, and even then may not provide adequate glycemic control or may produce undesired side effects. Such side effects include lactic acidosis (biguanides), hypoglycemia (sulfonylureas), and edema and weight gain (thiazolidinediones). Therefore, new antidiabetic agents providing improved glycemic control and lacking these adverse effects are highly desired.

One promising target for therapeutic intervention in diabetes and related disorders is the glucose transport system of the kidneys. Cellular glucose transport is conducted by either facilitative ("passive") glucose transporters (GLUTs) or sodium-dependent ("active") glucose cotransporters (SGLTs). SGLT1 is found predominantly in the intestinal brush border, while SGLT2 is localized in the renal proximal tubule and is reportedly responsible for the majority of glucose reuptake by the kidneys. Recent studies suggest that inhibition of renal SGLT may be a useful approach to treating hyperglycemia by increasing the amount of glucose excreted in the urine (Arakawa K, et al., Br J Pharmacol 132:578-86, 2001; Oku A, et al., Diabetes 48:1794-1800, 1999). The potential of this therapeutic approach is further supported by recent findings that mutations in the SGLT2 gene occur in cases of familial renal glucosuria, an apparently benign syndrome characterized by urinary glucose excretion in the presence of normal serum glucose levels and the absence of general renal dysfunction or other disease (Santer R, et al., J Am Soc Nephrol 14:2873-82, 2003). Therefore, compounds which inhibit SGLT, particularly SGLT2, are promising candidates for use as antidiabetic drugs. Compounds previously described as useful for inhibiting SGLT include spiroketal-glycoside derivatives (described in WO2006080421), C-glycoside derivatives (such as those described in U.S. Pat. No. 6,414,126, US20050209166, US20050233988, WO2005085237, U.S. Pat. No. 7,094,763, US20060122126 and WO2006108842), O-glycoside derivatives (such as those described in U.S. Pat. No. 6,683,056, US20050187168, US20060166899, US20060234954 and US20060247179), cyclohexane derivatives (such as those described in WO2006011469), and thio-glucopyranoside derivatives (such as those described in US20050209309 and WO2006073197).

BRIEF SUMMARY OF THE INVENTION

The present invention provides compounds having an inhibitory effect on sodium-dependent glucose cotransporter SGLT. The invention also provides pharmaceutical compositions, methods of preparing the compounds, synthetic intermediates, and methods of using the compounds, independently or in combination with other therapeutic agents, for treating diseases and conditions which are affected by SGLT inhibition.

DETAILED DESCRIPTION OF THE INVENTION

Definitions

Figure 1:
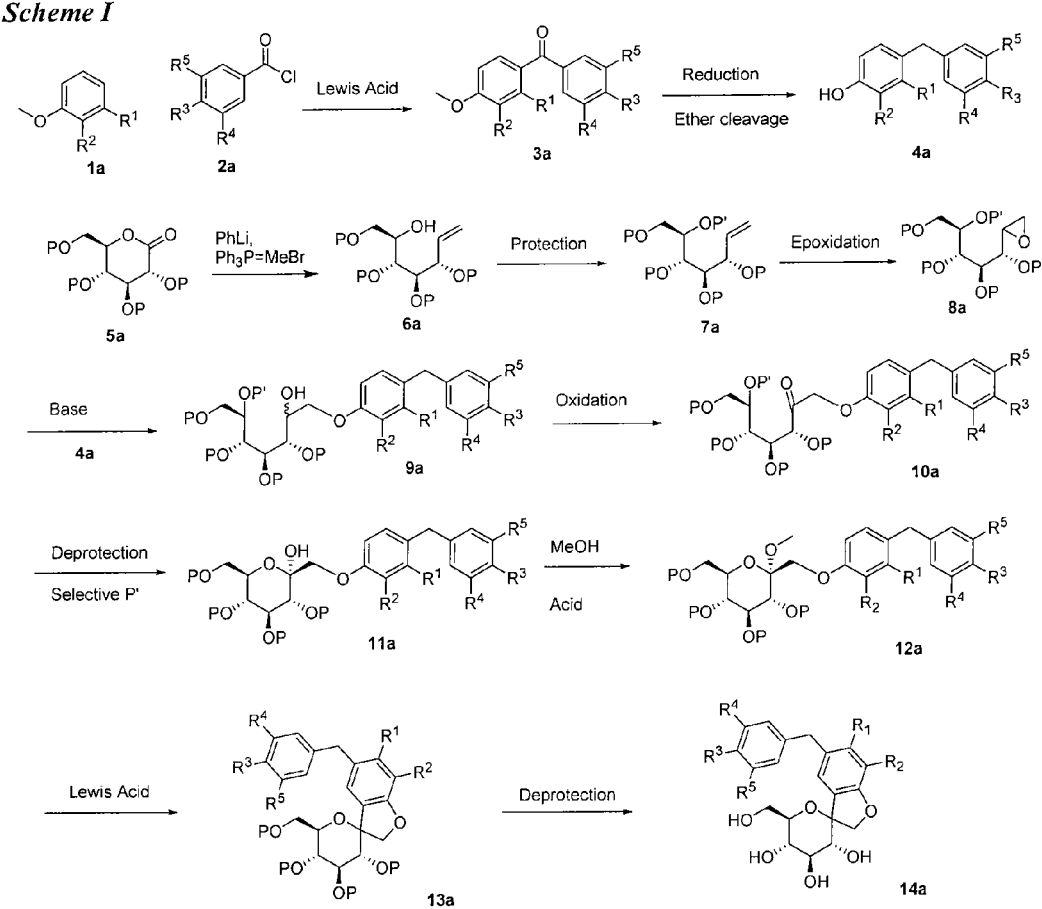
FIGS. 1-10 provide general synthesis schemes (Schemes I through X) as described in detail below.

As used herein, the term "halo" means a monovalent halogen radical or atom selected from fluoro, chloro, bromo and iodo. Preferred halo groups are fluoro, chloro and bromo.

As used herein, the term "suitable substituent" means a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents may be selected independently from the group consisting of halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl)$C_1$-$C_6$ alkoxy, $C_3$-$C_7$ heterocycloalkyl, ($C_3$-$C_7$ heterocycloalkyl)$C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxy, hydroxy, carboxy, oxo, sulfanyl, $C_1$-$C_6$ alkylsulfanyl, aryl, heteroaryl, aryloxy, heteroaryloxy, aralkyl, heteroaralkyl, aralkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, unless otherwise indicated, the term "alkyl" alone or in combination refers to a saturated aliphatic hydrocarbon radical having the indicated number of carbon atoms. The radical may be a linear or branched chain and, where specified, optionally substituted with one to three suitable substituents as defined above. Illustrative examples of alkyl groups include, but are not limited to, methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, n-dodecyl, n-tetradecyl, n-hexadecyl, n-octadecyl, n-eicosyl and the like. Preferred alkyl groups include methyl, ethyl, n-propyl and isopropyl. Preferred optional substituents include halo, methoxy, ethoxy, cyano, nitro and amino.

As used herein, unless otherwise indicated, the term "alkenyl" alone or in combination refers to an aliphatic hydrocarbon radical having the indicated number of carbon atoms and at least one carbon-carbon double bond. The radical may be a linear or branched chain, in the E or Z form, and, where specified, optionally substituted with one to three suitable substituents as defined above. Illustrative examples of alkenyl groups include, but are not limited to, vinyl, 1-propenyl, 2-propenyl, isopropenyl, 1-butenyl, 2-butenyl, isobutenyl, 2-methyl-1-propenyl, 1-pentenyl, 2-pentenyl, 4-methyl-2-pentenyl, 1,3-pentadienyl, 2,4-pentadienyl, 1,3-butadienyl and the like. Preferred alkenyl groups include vinyl, 1-propenyl and 2-propenyl. Preferred optional substituents include halo, methoxy, ethoxy, cyano, nitro and amino.

As used herein, unless otherwise indicated, the term "alkynyl" alone or in combination refers to an aliphatic hydrocarbon radical having the indicated number of carbon atoms and at least one carbon-carbon triple bond. The radical may be a linear or branched chain and, where specified, optionally substituted with one to three suitable substituents as defined above. Illustrative examples of alkynyl groups include, but are not limited to, ethynyl, 1-propynyl, 2-propynyl, 1-butynyl, 2-butynyl, 1-pentynyl, 2-pentynyl, 3-methyl-1-pentynyl, 3-pentynyl, 1-hexynyl, 2-hexynyl, 3-hexynyl and the like. Preferred alkynyl groups include ethynyl, 1-propynyl and 2-propynyl. Preferred optional substituents include halo, methoxy, ethoxy, cyano, nitro and amino.

As used herein, unless otherwise indicated, the term "cycloalkyl" alone or in combination refers to an alicyclic saturated hydrocarbon radical having three to ten carbons forming a carbocyclic ring and, where specified, optionally substituted with one to three suitable substituents as defined above. Illustrative examples of cycloalkyl groups include, but are not limited to, cyclopropyl, cyclobutyl, cyclopentyl, cyclohexyl, cycloheptyl, cyclooctyl, cyclononyl and the like.

As used herein, unless otherwise indicated, the term "cycloalkenyl" alone or in combination refers to an alicyclic hydrocarbon radical having three to ten carbons forming a carbocyclic ring and at least one carbon-carbon double bond and, where specified, optionally substituted with one to three suitable substituents as defined above. Illustrative examples of cycloalkenyl groups include, but are not limited to, cyclopentenyl, cyclohexenyl and the like.

As used herein, unless otherwise indicated, the term "aryl" alone or in combination refers to an aromatic hydrocarbon radical having six to ten carbon atoms forming a carbocyclic ring and, where specified, optionally substituted with one to three suitable substituents as defined above. Illustrative examples of aryl groups include, but are not limited to, phenyl, naphthyl, tetrahydronaphthyl, indanyl and the like. Preferred aryl groups are phenyl and naphthyl, optionally mono- or disubstituted by identical or different substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the term "heterocycloalkyl" alone or in combination refers to a cycloalkyl group as defined above in which one or more carbons in the ring is replaced by a heteroatom selected from N, S and O. Illustrative examples of heterocycloalkyl groups include, but are not limited to, pyrrolidinyl, tetrahydrofuranyl, piperazinyl, morpholinyl, tetrahydropyranyl, and the like.

As used herein, unless otherwise indicated, the term "heteroaryl" alone or in combination refers to an aromatic heterocyclic radical having two to nine carbon atoms and one to four heteroatoms selected from N, S and O forming a five- to ten-membered monocyclic or fused bicyclic ring and, where specified, optionally substituted with one to three suitable substituents as defined above. Illustrative examples of heteroaryl groups include, but are not limited to, pyridyl, pyridazinyl, pyrazinyl, pyrimidinyl, triazinyl, quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridines, benzothiaxolyl, benzofuranyl, benzothienyl, indolyl, isothiazolyl, pyrazolyl, indazolyl, imidazolyl, triazolyl, tetrazolyl, oxazolyl, isoxazolyl, oxadiazolyl, thiadiazolyl, pyrrolyl, thiazolyl, furyl, thienyl and the like. Five- or six-membered monocyclic heteroaryl rings include: pyridyl, pyridazinyl, pyrazinyl, pyrimidinyl, triazinyl, isothiazolyl, pyrazolyl, imidazolyl, triazolyl, tetrazolyl, oxazolyl, isoxazolyl, oxadiazolyl, thiadiazolyl, pyrrolyl, thiazolyl, furyl, thienyl and the like. Eight- to ten-membered bicyclic heteroaryl rings having one to four heteroatoms include: quinolinyl, isoquinolinyl, quinoxalinyl, quinazolinyl, benzotriazinyl, benzimidazolyl, benzopyrazolyl, benzotriazolyl, benzisoxazolyl, isobenzofuryl, isoindolyl, indolizinyl, thienopyridinyl, thienopyrimidinyl, pyrazolopyrimidinyl, imidazopyridinyl, benzothiaxolyl, benzofuranyl, benzothienyl, indolyl, indazolyl, and the like. Preferred optional substitutions include one or two identical or different substituents selected from halo, cyano, $C_1$-$C_3$ alkyl, $C_3$-$C_6$ cycloalkyl, difluoromethyl, trifluoromethyl, $C_1$-$C_3$ alkoxy, difluoromethoxy and trifluoromethoxy.

As used herein, unless otherwise indicated, the term "alkoxy" alone or in combination refers to an aliphatic radical of the form alkyl-O—, wherein alkyl is as defined above. Illustrative examples of alkoxy groups include, but are not limited to, methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy, octoxy and the like. Preferred alkoxy groups include methoxy and ethoxy.

As used herein, unless otherwise indicated, the term "haloalkyl" refers to an alkyl radical as described above substituted with one or more halogens. Illustrative examples of haloalkyl groups include, but are not limited to, chloromethyl, dichloromethyl, fluoromethyl, difluoromethyl, trifluoromethyl, 2,2,2-trichloroethyl and the like.

As used herein, unless otherwise indicated, the term "haloalkoxy" refers to an alkoxy radical as described above substituted with one or more halogens. Illustrative examples of haloalkoxy groups include, but are not limited to, trifluoromethoxy, difluoromethoxy and the like.

As used herein, unless otherwise indicated, the term "aralkyl" refers to an alkyl radical of one to six carbons as described above substituted with an aryl group as described above.

As used herein, unless otherwise indicated, the term "heteroaralkyl" refers to an alkyl radical of one to six carbons as described above substituted with a heteroaryl group as described above.

As used herein, unless otherwise indicated, the term "aralkoxy" refers to an alkoxy radical of one to six carbons as described above substituted with an aryl group as described above.

As used herein, unless otherwise indicated, the term "heteroaralkoxy" refers to an alkoxy radical of one to six carbons as described above substituted with a heteroaryl group as described above.

As used herein, unless otherwise indicated, the term "carbamoyl" refers to a monovalent radical of the form —C(O)NH(R), wherein R is hydrogen, $C_1$-$C_6$ alkyl, $C_2$-$C_6$ alkenyl, $C_3$-$C_6$ cycloalkyl, or aryl as such terms are defined above.

As used herein, unless otherwise indicated, the terms "di-($C_1$-$C_3$ alkyl)amino" and "di-($C_1$-$C_6$ alkyl)amino" alone or in combination refer to an amino group that is substituted with two groups independently selected from $C_1$-$C_3$ alkyl or $C_1$-$C_6$ alkyl, respectively.

As used herein, the terms "treating" and "treatment" refer to delaying the onset of, retarding or reversing the progress of, or alleviating or preventing either the disease or condition to which the term applies, or one or more symptoms of such disease or condition.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, and the like.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound).

As used herein, the term "compound" refers to a molecule produced by any means including, without limitation, synthesis in vitro or generation in situ or in vivo.

The terms "controlled release," "sustained release," "extended release," and "timed release" are intended to refer interchangeably to any drug-containing formulation in which release of the drug is not immediate, i.e., with a "controlled release" formulation, oral administration does not result in immediate release of the drug into an absorption pool. The terms are used interchangeably with "nonimmediate release" as defined in *Remington: The Science and Practice of Pharmacy*, 21$^{st}$ Ed., Gennaro, Ed., Lippencott Williams & Wilkins (2003). As discussed therein, immediate and nonimmediate release can be defined kinetically by reference to the following equation:

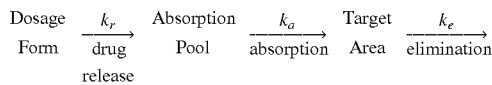

The "absorption pool" represents a solution of the drug administered at a particular absorption site, and $k_r$, $k_a$ and $k_e$ are first-order rate constants for (1) release of the drug from the formulation, (2) absorption, and (3) elimination, respectively. For immediate release dosage forms, the rate constant for drug release $k_r$ is far greater than the absorption rate constant $k_a$. For controlled release formulations, the opposite is true, i.e., $k_r \ll k_a$, such that the rate of release of drug from the dosage form is the rate-limiting step in the delivery of the drug to the target area.

The terms "sustained release" and "extended release" are used in their conventional sense to refer to a drug formulation that provides for gradual release of a drug over an extended period of time, for example, 12 hours or more, and that preferably, although not necessarily, results in substantially constant blood levels of a drug over an extended time period.

As used herein, the term "delayed release" refers to a pharmaceutical preparation that passes through the stomach intact and dissolves in the small intestine.

General

The present invention provides compounds having an inhibitory effect on sodium-dependent glucose cotransporter SGLT, preferably SGLT2. Some compounds according to the present invention also have an inhibitory effect on sodium-dependent glucose cotransporter SGLT1. Owing to their ability to inhibit SGLT, the compounds of the present invention are suitable for the treatment and/or prevention of any and all conditions and diseases that are affected by inhibition of SGLT activity, particularly SGLT2 activity. Therefore, the compounds of the present invention are suitable for the prevention and treatment of diseases and conditions, particularly metabolic disorders, including but not mited to type 1 and type 2 diabetes mellitus, hyperglycemia, diabetic complications (such as retinopathy, nephropathy [e.g., progressive renal disease], neuropathy, ulcers, micro- and macroangiopathies, and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases.

The present invention also provides pharmaceutically acceptable salts and prodrugs of compounds according to the present invention.

The present invention further provides pharmaceutical compositions comprising an effective amount of a compound or mixture of compounds according to the present invention, or a pharmaceutically acceptable salt or prodrug thereof, in a pharmaceutically acceptable carrier.

The present invention further provides synthetic intermediates and processes for preparing the compounds of the present invention.

The present invention also provides methods of using the compounds according to the present invention, independently or in combination with other therapeutic agents, for treating diseases and conditions which may be affected by SGLT inhibition.

The present invention also provides methods of using the compounds according to the present invention for the preparation of a medicament for treating diseases and conditions which may be affected by SGLT inhibition.

Detailed Embodiments

Compounds and Preparative Methods

In one aspect, the present invention provides for compounds of Formula I:

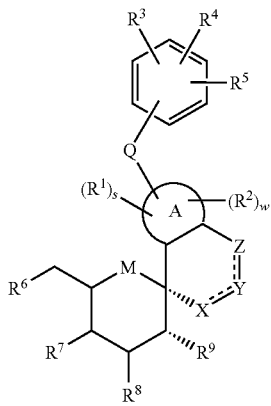

wherein
the bond between X and Y may be a single bond or a double bond, and the bond between Y and Z may be a single bond or a double bond; or optionally, Y represents a bond which is a single bond or a double bond covalently attaching X to Z;

subscript s is an integer from 0 to 1 and subscript w is an integer from 0 to 2;

M represents oxygen; sulfur; SO; $SO_2$; methylene optionally substituted with one to two substituents independently selected from halo, $C_1$-$C_6$ alkyl, $C_1$-$C_6$ alkoxy, $C_3$-$C_6$ cycloalkyl and $C_3$-$C_6$ cycloalkyloxy; $C_3$-$C_5$ 1,1-cycloalkylene optionally substituted with one to two substituents independently selected from halo, $C_1$-$C_6$ alkyl, $C_1$-$C_6$ alkoxy, $C_3$-$C_6$ cycloalkyl and $C_3$-$C_6$ cycloalkyloxy; or $NR^a$;

wherein in cycloalkyl groups or portions one or two methylene groups may be optionally replaced independently of one another by $NR^b$, O, S, CO, SO or $SO_2$;

X is defined as follows:

(a1) when Y represents a single bond or when the bond between X and Y is a single bond, X represents oxygen; sulfur; SO; $SO_2$; $NR^c$; methylene optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; or $C_3$-$C_5$ 1,1-cycloalkylene optionally substituted with one to two substituents independently selected from halo, $C_1$-$C_6$ alkyl and $C_1$-$C_6$ alkoxy; or (b1) when Y represents a double bond or when the bond between X and Y is a double bond, X represents N; or CH optionally substituted with a substituent selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl;

wherein in cycloalkyl groups or portions one or two methylene groups may be optionally replaced independently of one another by $NR^b$, O, S, CO, SO or $SO_2$;

Y is further defined as follows:

(a2) when the bond between X and Y is a single bond and the bond between Y and Z is a single bond, Y represents $(CH_2)_n$; $(CH_2)_kC(O)$; $C(O)(CH_2)_k$; $C(O)NH(CH_2)_p$; $C(O)O(CH_2)_p$; $(CH_2)_mSO_2$; $SO_2(CH_2)_k$; or $(O)C(CH_2)_pC(O)$; wherein n is an integer from 1 to 3, k is an integer from 1 to 2, m is an integer from 0 to 2, p is an integer from 0 to 1, and each $CH_2$ independently may be optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; or (b2) when the bond between X and Y is a single bond and the bond between Y and Z is a double bond, Y represents $(CH_2)_kCH$; $C(O)(CH_2)_pCH$; $C(O)NHCH$; $C(O)N$; $C(O)OCH$; or $SO_2(CH_2)_pCH$; wherein k is an integer from 1 to 2, p is an integer from 0 to 1, and each hydrogen independently may be optionally replaced with a substituent independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; or (c2) when the bond between X and Y is a double bond and the bond between Y and Z is a single bond, Y represents $CH(CH_2)_m$; $CH(CH_2)_pC(O)$; or $CH(CH_2)_pSO_2$; wherein m is an integer from 0 to 2, p is an integer from 0 to 1, and each hydrogen independently may be optionally replaced with a substituent independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; or (d2) when the bond between X and Y is a double bond and the bond between Y and Z is a double bond, Y represents $CH(CH_2)_pCH$; wherein p is an integer from 0 to 1, and each hydrogen independently may be optionally replaced with a substituent independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl;

wherein in cycloalkyl groups one or two methylene groups may be optionally replaced independently of one another by $NR^b$, O, S, CO, SO or $SO_2$;

Z is defined as follows:

(a3) when Y represents other than a bond, Z represents oxygen; sulfur; SO; or $NR^d$; or (b3) when Y represents a single bond, Z represents $O(CH_2)_m$; $S(CH_2)_m$; $SO(CH_2)_m$; or $NR^d(CH_2)_m$, wherein m is an integer from 0 to 2, and each $CH_2$ independently is optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; or (c3) when Y represents a double bond, Z represents $N(CH_2)_m$, wherein m is an integer from 0 to 2, and each $CH_2$ independently is optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl;

wherein in cycloalkyl groups or portions one or two methylene groups may be optionally replaced independently of one another by $NR^b$, O, S, CO, SO or $SO_2$;

Ring A represents (a4) a benzene ring; or (b4) a five- or six-membered monocyclic heteroaryl ring having one or two heteroatom(s) independently selected from N, S, and O; or (c4) an eight- to ten-membered bicyclic heteroaryl ring having one to four heteroatom(s) independently selected from N, S, and O;

In view of the various embodiments for ring A, one of skill in the art will appreciate that the subscripts s and w in combination will not exceed the available valences for the available attachment sites on ring vertices. Additionally, for those embodiments in which s and/or w are 0, the available valences will be substituted with hydrogen.

Q represents oxygen; sulfur; SO; $SO_2$; 1,1-cyclopropylene; carbonyl; or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy;

wherein in cycloalkyl groups or portions one or two methylene groups may be optionally replaced independently of one another by $NR^b$, O, S, CO, SO or $SO_2$;

$R^1$ independently represents halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy)$C_1$-$C_3$ alkyl, $C_5$-$C_{10}$ cycloalkenyl, ($C_5$-$C_{10}$ cycloalkenyl)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_1$-$C_4$ alkyl)carbonyl, aryl, heteroaryl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy; (heteroaryl)$C_1$-$C_3$ alkyloxy; $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano or nitro;

wherein alkyl, alkenyl, alkynyl, cycloalkyl and cycloalkenyl groups or portions may be partly or completely fluorinated or may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^b$, O, S, CO, SO or $SO_2$, and in N-heterocycloalkyl groups or portions a methylene group may be replaced by CO or $SO_2$;

each $R^2$ independently represents halo, hydroxy, $C_1$-$C_4$ alkyl, $C_3$-$C_{10}$ cycloalkyl, $C_1$-$C_4$ alkyloxy, $C_3$-$C_{10}$ cycloalkyloxy, cyano or nitro, wherein alkyl groups or portions may be mono- or polysubstituted by fluorine, and in cycloalkyl groups one or two methylene groups may be optionally replaced independently of one another by $NR^b$, O, S, CO, SO or $SO_2$;

$R^3$ independently represents hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy)$C_1$-$C_3$ alkyl, $C_5$-$C_{10}$ cycloalkenyl, ($C_5$-$C_{10}$ cycloalkenyl)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_1$-$C_4$ alkyl)carbonyl, aryl, heteroaryl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy; (heteroaryl)$C_1$-$C_3$ alkyloxy; $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano, nitro, ($C_1$-$C_6$ alkyloxy)$C_1$-$C_6$ alkyloxy, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkyloxy, ($C_3$-$C_7$ cycloalkyloxy)$C_2$-$C_4$ alkenyl, ($C_3$-$C_7$ cycloalkyloxy)$C_2$-$C_4$ alkynyl or ($C_3$-$C_7$ cycloalkyloxy)$C_1$-$C_3$ alkyloxy;

wherein alkyl, alkenyl, alkynyl, cycloalkyl and cycloalkenyl groups or portions may be partly or completely fluorinated or may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^b$, O, S, CO, SO or $SO_2$, and in N-heterocycloalkyl groups or portions a methylene group may be replaced by CO or $SO_2$;

$R^4$ independently represents hydrogen, halo, hydroxy, cyano, nitro, $C_1$-$C_3$ alkyl, $C_3$-$C_{10}$ cycloalkyl, $C_1$-$C_3$ alkoxy or methyl or methoxy substituted by 1 to 3 fluorine atoms, and in cycloalkyl groups one or two methylene groups may be optionally replaced independently of one another by $NR^b$, O, S, CO, SO or $SO_2$; or if $R^3$ and $R^4$ are bound to two adjacent C atoms of the phenyl ring, $R^3$ and $R^4$ may be joined together such that $R^3$ and $R^4$ together form a $C_3$-$C_5$ alkylene or $C_3$-$C_5$ alkenylene bridge, which may be partly or completely fluorinated or mono- or disubstituted by identical or different substituents selected from chlorine, hydroxy, $C_1$-$C_3$ alkoxy and $C_1$-$C_3$ alkyl, and wherein one or two methylene groups are optionally replaced independently of one another by O, S, CO, SO, $SO_2$ or $NR^b$, and wherein one or two methylene groups may be replaced by an N atom;

$R^5$ independently represents hydrogen, halo, hydroxy, cyano, nitro, $C_1$-$C_3$ alkyl, $C_3$-$C_{10}$ cycloalkyl, $C_1$-$C_3$ alkoxy or methyl or methoxy substituted by 1 to 3 fluorine atoms, and in cycloalkyl groups one or two methylene groups may be optionally replaced independently of one another by $NR^b$, O, S, CO, SO or $SO_2$;

$R^6$, $R^7$, $R^8$ and $R^9$ each independently represent hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, hydrogen, halo, $C_1$-$C_6$ alkyl, $C_2$-$C_6$ alkenyl, $C_2$-$C_6$ alkynyl, ($C_3$-$C_{10}$) cycloalkyl-($C_1$-$C_3$)alkyl, ($C_5$-$C_7$)cycloalkenyl-($C_1$-$C_3$)alkyl, aryl-($C_1$-$C_3$)alkyl, heteroaryl-($C_1$-$C_3$)alkyl, $C_1$-$C_6$ alkyloxy, $C_2$-$C_6$ alkenyloxy, $C_2$-$C_6$ alkynyloxy, ($C_3$-$C_7$)cycloalkyloxy, $C_5$-$C_7$ cycloalkenyloxy, aryloxy, heteroaryloxy, ($C_3$-$C_7$)cycloalkyl-($C_1$-$C_3$)alkyloxy, ($C_5$-$C_7$)cycloalkenyl-($C_1$-$C_3$)alkyloxy, aryl-($C_1$-$C_3$)alkyloxy, heteroaryl-($C_1$-$C_3$)alkyloxy, aminocarbonyl, hydroxycarbonyl, ($C_1$-$C_4$ alkyl)aminocarbonyl, di-($C_1$-$C_3$ alkyl)aminocarbonyl, ($C_1$-$C_4$ alkyloxy)carbonyl, aminocarbonyl-($C_1$-$C_3$)alkyl, ($C_1$-$C_4$)alkylaminocarbonyl-($C_1$-$C_3$)alkyl, di-($C_1$-$C_3$ alkyl)aminocarbonyl-($C_1$-$C_3$)alkyl, hydroxycarbonyl-($C_1$-$C_3$)alkyl, ($C_1$-$C_4$ alkyloxy)carbonyl-($C_1$-$C_3$)alkyl, ($C_3$-$C_7$)cycloalkyloxy-($C_1$-$C_3$)alkyl, ($C_5$-$C_7$)cycloalkenyloxy-($C_1$-$C_3$)alkyl, aryloxy-($C_1$-$C_3$)alkyl, heteroaryloxy-($C_1$-$C_3$)alkyl, $C_1$-$C_4$ alkylsulfonyloxy, arylsulfonyloxy, aryl-($C_1$-$C_3$)alkyl-sulfonyloxy, trimethylsilyloxy, t-butyldimethylsilyloxy, or cyano;

wherein alkyl, alkenyl, alkynyl, cycloalkyl and cycloalkenyl groups or portions may be partly or completely fluorinated or may be mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^b$, O, S, CO, SO or $SO_2$;

$R^a$, $R^b$ and $R^c$ each independently represent H, $C_1$-$C_6$ alkyl, $C_3$-$C_6$ cycloalkyl or ($C_1$-$C_4$ alkyl)carbonyl, wherein alkyl and cycloalkyl groups or portions may be partly or completely fluorinated;

$R^d$ independently represents H, $C_1$-$C_6$ alkyl, $CHR^eR^f$, ($C_1$-$C_4$ alkyl)carbonyl, $SO_2R^e$, $C(O)OR^e$ or $C(O)NR^eR^f$, wherein alkyl groups or portions may be partly or completely fluorinated; and $R^e$ and $R^f$ each independently represent H or $C_1$-$C_6$ alkyl, wherein alkyl groups or portions may be partly or completely fluorinated.

The style used above and hereinafter, in which a bond of a substituent on a phenyl group is shown ending near the center of the phenyl ring, denotes, unless otherwise stated, that this substituent may be bound to any free position of the phenyl group bearing a hydrogen atom.

The present invention includes all tautomers and stereoisomers of compounds of Formula I, Formulae IA and Formula IB (below) either in admixture or in pure or substantially pure form. The compounds of the present invention can have asymmetric centers at the carbon atoms, and therefore the compounds of Formula I, IA and IB can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

The present invention also provides for the prodrugs of compounds of Formula I, IA and IB. Prodrugs of compounds of the invention include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Prodrug esters and carbonates may be formed, for example, by reacting one or more hydroxyl groups of compounds of Formula I, IA and IB, with alkyl, alkoxy or aryl substituted acylating reagents using methods known to those of skill in the art to produce methyl carbonates, acetates, benzoates, pivalates and the like. Illustrative examples of prodrug esters of the compounds of the present invention include, but are not limited to, compounds of Formula I, IA and IB having a carboxyl moiety wherein the free hydrogen is replaced by $C_1$-$C_4$ alkyl, $C_1$-$C_7$ alkanoyloxymethyl, 1-(($C_1$-$C_5$)alkanoyloxy)ethyl, 1-methyl-1-(($C_1$-$C_5$)alkanoyloxy)-ethyl, $C_1$-$C_5$ alkoxycarbonyloxymethyl, 1-(($C_1$-$C_5$)alkoxycarbonyloxy)ethyl, 1-methyl-1-(($C_1$-$C_5$)alkoxycarbonyloxy) ethyl, N—(($C_1$-$C_5$)alkoxycarbonyl)aminomethyl, 1-(N—(($C_1$-$C_5$)alkoxycarbonyl)amino)ethyl, 3-phthalidyl, 4-crotonolactonyl, gamma-butyrolacton-4-yl, di-N,N—($C_1$-$C_2$)alkylamino($C_2$-$C_3$)alkyl (e.g., beta-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino ($C_2$-$C_3$)alkyl. Oligopeptide modifications and biodegradable polymer derivatives (as described, for example, in Int. J. Pharm. 115, 61-67, 1995) are within the scope of the invention Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, "Design of Prodrugs," Elsevier, 1985; and "Bioreversible Carriers in Drug Design," ed. Edward Roche, American Pharmaceutical Association and Pergamon Press, 1987.

The present invention also provides for the pharmaceutically acceptable salts of compounds of Formula I, IA and IB and prodrugs thereof. The acids that can be used as reagents to prepare the pharmaceutically acceptable acid addition salts of the basic compounds of this invention are those which form non-toxic acid addition salts, i.e., salts containing pharmacologically acceptable anions (such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (1,1'-methylene-bis-2-hydroxy-3-naphthoate) salts). The bases that can be used as reagents to prepare the pharmaceutically acceptable base salts of the acidic compounds of the present invention are those that form non-toxic base salts with such compounds, including, but not limited to, those derived from pharmacologically acceptable cations such as alkali metal cations (e.g., potassium, lithium and sodium) and alkaline earth metal cations (e.g., calcium and magnesium), ammonium or water-soluble amine addition salts such as N-methylglucamine (meglumine), and the lower alkanolammonium and other base salts of pharmaceutically acceptable organic amines (e.g., methylamine, ethylamine, propylamine, dimethylamine, triethanolamine, diethylamine, t-butylamine, t-octylamine, trimethylamine, triethylamine, ethylenediamine, hydroxyethylamine, morpholine, piperazine, dehydroabietylamine, lysine and guanidine).

The present invention also includes isotopically-labeled compounds of Formula I, IA and IB, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2H$, $^3H$, $^{13}C$, $^{14}C$, $^{15}N$, $^{18}O$, $^{17}O$, $^{18}F$, $^{35}S$ and $^{36}Cl$). Isotopically-labeled compounds of Formula I, IA and IB and prodrugs thereof, as well as isotopically-labeled, pharmaceutically acceptable salts of compounds of Formula I, IA and IB and prodrugs thereof, are within the scope of the present invention. Isotopically-labeled compounds of the present invention are useful in assays of the tissue distribution of the compounds and their prodrugs and metabolites; preferred isotopes for such assays include $^3H$ and $^{14}C$. In addition, in certain circumstances substitution with heavier isotopes, such as deuterium ($^2H$), can provide increased metabolic stability, which offers therapeutic advantages such as increased in vivo half-life or reduced dosage requirements. Isotopically-labeled compounds of this invention and prodrugs thereof can generally be prepared according to the methods described herein by substituting an isotopically-labeled reagent for a non-isotopically labeled reagent.

In preferred embodiments, M represents oxygen or sulfur. In particularly preferred embodiments, M represents oxygen.

In preferred embodiments, X represents methylene optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; Y represents a single bond; and Z represents $O(CH_2)_m$, $S(CH_2)_m$, $SO(CH_2)_m$ or $NR^d(CH_2)_m$. In other preferred embodiments, X represents methylene optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; Y represents $(CH_2)_n$; and Z represents oxygen, sulfur, SO or $NR^d$. In particularly preferred embodiments, X represents methylene, Y represents a single bond and Z represents $O(CH_2)_m$. In other particularly preferred embodiments, X represents methylene, Y represents $(CH_2)_n$ and Z represents oxygen.

In preferred embodiments, ring A represents a benzene ring or a five- or six-membered monocyclic heteroaryl ring having one or two heteroatom(s) independently selected from N, S, and O. In particularly preferred embodiments, ring A represents a benzene ring.

In preferred embodiments, Q represents oxygen, sulfur, or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy. In particularly preferred embodiments, Q represents methylene.

In certain preferred embodiments, the subscript s is 0. In other preferred embodiments the subscript s is 1 and $R^1$ represents halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro, wherein alkyl and cycloalkyl groups or portions may be partly or completely fluorinated. In particularly preferred embodiments, the subscript s is 0, or the subscript s is 1 and $R^1$ represents halo or $C_1$-$C_6$ alkyl.

In certain preferred embodiments, the subscript w is 0. In other preferred embodiments the subscript w is 1 or 2 and $R^2$ represents halo, $C_1$-$C_4$ alkyl, or $C_1$-$C_4$ alkyloxy. In particularly preferred embodiments, the subscript w is 0, or the subscript w is 1 and $R^2$ represents halo.

In preferred embodiments, $R^3$ represents hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro, wherein alkyl and cycloalkyl groups or portions may be partly or completely fluorinated, and in cycloalkyl groups one or two methylene groups are optionally replaced independently of one another by $NR^b$, O, S, CO, SO or $SO_2$. In particularly preferred embodiments, $R^3$ represents hydrogen, halo, $C_1$-$C_6$ alkyl, $C_1$-$C_6$ alkyloxy, or $C_3$-$C_{10}$ cycloalkyloxy, wherein alkyl and cycloalkyl groups or portions may be partly or completely fluorinated, and in cycloalkyl groups a methylene group is optionally replaced by $NR^b$, O, S, CO, SO or $SO_2$.

In preferred embodiments, $R^4$ and $R^5$ independently represent hydrogen, halo, $C_1$-$C_3$ alkyl, $C_3$-$C_{10}$ cycloalkyl or $C_1$-$C_3$ alkoxy. In particularly preferred embodiments, $R^4$ and $R^5$ independently represent hydrogen or halo.

In preferred embodiments, $R^6$, $R^7$, $R^8$ and $R^9$ each independently represent hydroxy, halo, $C_1$-$C_6$ alkyl, $C_1$-$C_6$ alkyloxy, ($C_3$-$C_7$)cycloalkyloxy, or ($C_3$-$C_7$)cycloalkyl-($C_1$-$C_3$) alkyloxy, wherein alkyl and cycloalkyl groups or portions may be partly or completely fluorinated. In particularly preferred embodiments, $R^6$, $R^7$, $R^8$ and $R^9$ each represent hydroxy.

As noted above, Formula IA and IB represent still other preferred embodiments. In one group, the compounds are represented by Formula IA:

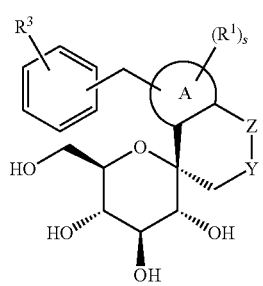

wherein the subscript s is 0, or the subscript s is 1 and $R^1$ represents halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro; Y represents a single bond and Z represents $O(CH_2)_m$, $S(CH_2)_m$, $SO(CH_2)_m$ or $NR^d(CH_2)_m$ wherein m is an integer from 0 to 2, or Y represents $(CH_2)_n$ wherein n is an integer from 1 to 3 and Z represents oxygen, sulfur, SO or $NR^d$; ring A represents a benzene ring or a five- or six-membered monocyclic heteroaryl ring having one or two heteroatom(s) independently selected from N, S, and O; and $R^3$ represents hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro, wherein in cycloalkyl groups one or two methylene groups are optionally replaced independently of one another by $NR^b$, O, S, CO, SO or $SO_2$.

Particularly preferred are compounds of Formula IB:

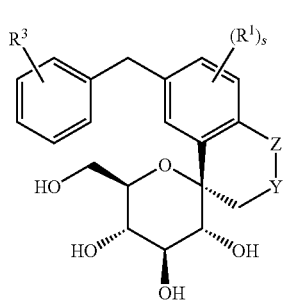

wherein the subscript s is 0, or the subscript s is 1 and $R^1$ represents halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro; Y represents a single bond and Z represents $O(CH_2)_m$, $S(CH_2)_m$, $SO(CH_2)_m$ or $NR^d(CH_2)_m$ wherein m is an integer from 0 to 2, or Y represents $(CH_2)_n$ wherein n is an integer from 1 to 3 and Z represents oxygen, sulfur, SO or $NR^d$; and $R^3$ represents hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano or nitro, wherein in cycloalkyl groups one or two methylene groups are optionally replaced independently of one another by $NR^b$, O, S, CO, SO or $SO_2$.

In another aspect, the present invention includes the compounds of Formula I and pharmaceutically acceptable salts, prodrugs and/or isotopically labeled compounds thereof, wherein alkyl, alkenyl, alkynyl, cycloalkyl, cycloalkenyl, aryl and heteroaryl groups or portions are optionally substituted with one to three suitable substituents as defined above.

In another aspect, the present invention provides for processes of preparing the compounds of Formula I, and pharmaceutically acceptable salts and prodrugs thereof. Such processes are outlined in the following general preparative methods depicted in Schemes I-VI, with more detailed particular examples being presented below in the experimental section describing the working examples. By following the general preparative methods discussed below, or employing variations or alternative methods, the compounds of the invention can be readily prepared by the use of chemical reactions and procedures known to those of skill in the art. Unless otherwise specified, the variables (e.g., R groups) denoting groups in the general methods described below have the meanings as hereinbefore defined.

Those of skill in the art will recognize that compounds of the invention with each described functional group are generally prepared using slight variations of the below-listed general methods. Within the scope of each method, functional groups which are suitable to the reaction conditions are used. Functional groups which might interfere with certain reactions are presented in protected forms where necessary, and the removal of such protective groups is completed at appropriate stages by methods well known to those skilled in the art.

In certain cases compounds of the invention can be prepared from other compounds of the invention by elaboration, transformation, exchange and the like of the functional groups present. Such elaboration includes, but is not limited to, hydrolysis, reduction, oxidation, alkylation, acylation, esterification, amidation and dehydration. Such transformations can in some instances require the use of protecting groups by the methods disclosed in T. W. Greene and P. G. M. Wuts, *Protective Groups in Organic Synthesis*; Wiley: New York, (1999), and incorporated herein by reference. Such methods would be initiated after synthesis of the desired compound or at another place in the synthetic route that would be readily apparent to one skilled in the art.

In another aspect, the present invention provides for synthetic intermediates useful for preparing the compounds of Formula I, and pharmaceutically acceptable salts and prodrugs thereof, according to the general preparative methods discussed below and other processes known to those of skill in the art.

In view of the above, the present invention provides a method of preparing compounds of Formula I, wherein the portion

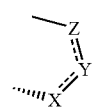

is selected from —CH$_2$O—, —CH$_2$CH$_2$O— and —CH$_2$CH$_2$CH$_2$O—, M is oxygen and ring A is benzene, the method comprising:

(i) coupling a phenol intermediate having the formula:

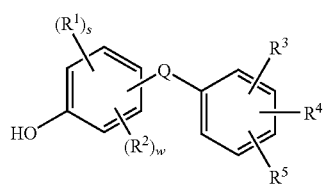

with a suitable sugar derivative to form a framework intermediate having formula IIa:

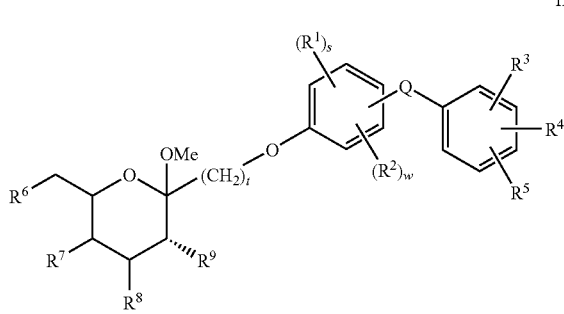

wherein the subscript t is an integer of from 1 to 3; and (ii) cyclizing the framework intermediate to form the compound having the formula:

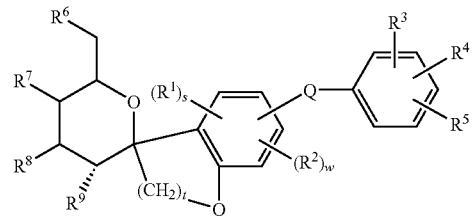

wherein the variables have the meanings provided with respect to Formula I, unless otherwise indicated. In one group of embodiments, the cyclizing is carried out in the presence of a Lewis acid catalyst. In another group of embodiments, subscript t is 1. In still another group of embodiments, the subscript t is 2. In yet another group of embodiments, the subscript t is 3.

In a related group of embodiments, the present invention provides a method of preparing compounds of Formula I, wherein the portion

is selected from —CH$_2$CH$_2$NR$^d$— and —CH$_2$CH$_2$CH$_2$NR$^d$—, M is oxygen and ring A is benzene, the method comprising:

(i) coupling an aniline intermediate having the formula:

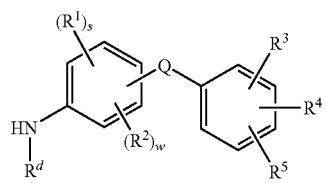

with a suitable sugar derivative to form a framework intermediate having formula IIb:

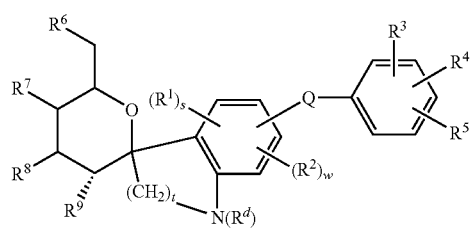

IIb wherein the subscript t is an integer of from 2 to 3; and (ii) cyclizing the framework intermediate to form the compound having the formula:

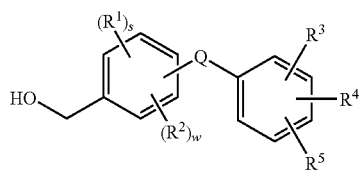

wherein the variables have the meanings provided with respect to Formula I, unless otherwise indicated. In one group of embodiments, the cyclizing is carried out in the presence of a Lewis acid catalyst. In another group of embodiments, subscript t is 2 and $R^d$ is hydrogen.

In another related group of embodiments, the present invention provides a method of preparing compounds of Formula I, wherein the portion

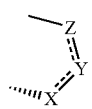

is selected from —CH$_2$OCH$_2$—, and —CH$_2$CH$_2$OCH$_2$—, M is oxygen and ring A is benzene, the method comprising:

(i) coupling a benzylic alcohol intermediate having the formula:

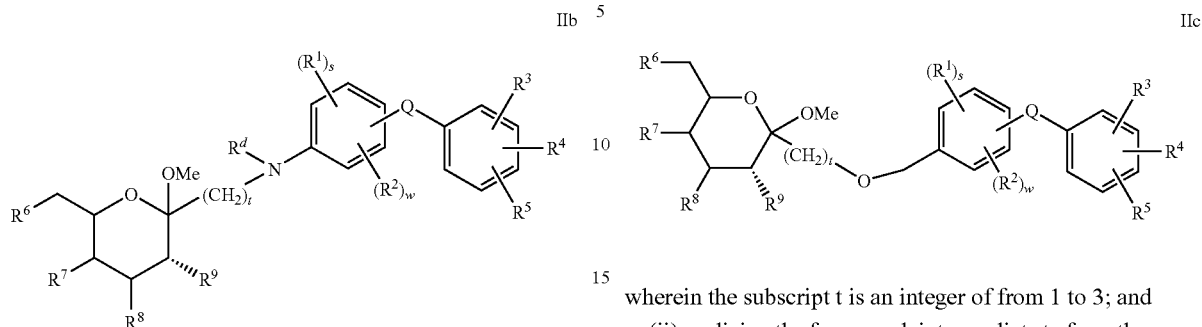

with a suitable sugar derivative to form a framework intermediate having formula IIc:

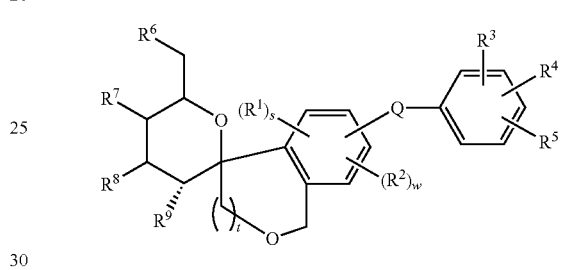

IIc wherein the subscript t is an integer of from 1 to 3; and (ii) cyclizing the framework intermediate to form the compound having the formula:

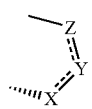

wherein the variables have the meanings provided with respect to Formula I, unless otherwise indicated. In one group of embodiments, the cyclizing is carried out in the presence of a Lewis acid catalyst.

In a related group of embodiments, the present invention provides a method of preparing compounds of Formula I, wherein the portion

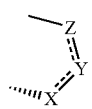

is selected from the group consisting of —CH$_2$O—, —CH$_2$CH$_2$O—, —CH$_2$CH(OH)O—, —CH$_2$CH(CH$_3$)O—, —CH$_2$C(CH$_2$OH)(CH$_3$)O—, —CH$_2$C(OH)(CH$_3$)O—, —CH$_2$CH(OCH$_3$)O—, and —CH$_2$CH$_2$CH$_2$O—, M is oxygen and ring A is benzene, the method comprising:

(i) coupling an intermediate having the formula:

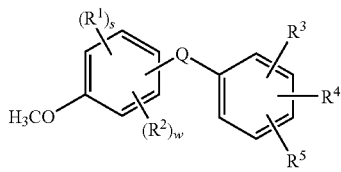

with a suitable sugar derivative to form a framework intermediate having formula:

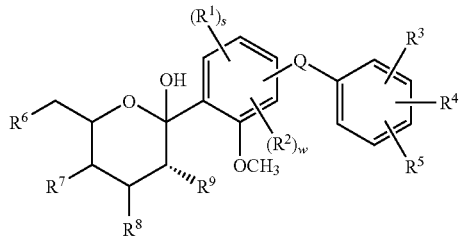

(ii) coupling an allyl or methallyl component to the C1-position of the sugar portion to produce an intermediate having the formula:

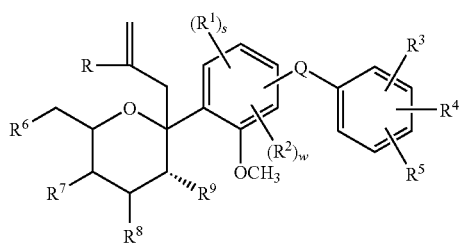

wherein R is H or CH₃;
(iii) converting said framework intermediate to said compound having the formula:

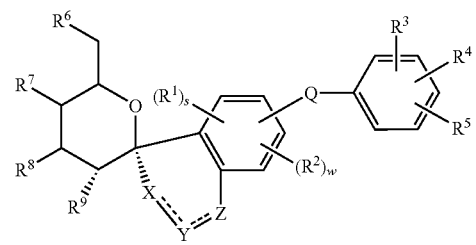

through one or more steps comprising ether cleavage, ozonolysis, hydroboration or epoxidation.

The present invention further provides an intermediate compound having a formula selected from the group consisting of IIa, IIb, IIc, IId and IIe:

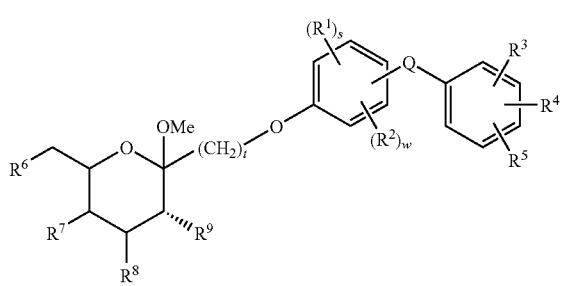

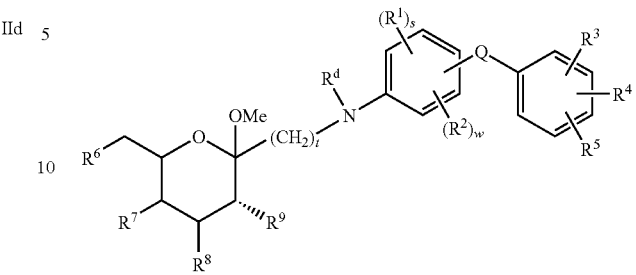

wherein the subscript t is an integer from 1 to 3 if formula IIa, an integer of from 2 to 3 in formula IIb and an integer of from 1 to 2 in formula IIc; the subscript s is an integer from 0 to 1; the subscript w is an integer from 0 to 2; Q is a member selected from the group consisting of oxygen; sulfur; SO; SO₂; 1,1-cyclopropylene; carbonyl; or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy; wherein in cycloalkyl groups one or two methylene groups are optionally replaced independently of one another by $NR^b$, O, S, CO, SO or SO₂;

$R^1$ is a member selected from the group consisting of halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy)$C_1$-$C_3$ alkyl, $C_5$-$C_{10}$ cycloalkenyl, ($C_5$-$C_{10}$ cycloalkenyl)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_1$-$C_4$ alkyl)carbonyl, aryl, heteroaryl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, pyrrolidin-1-ylcarbonyl, piperidin-1-ylcarbonyl, morpholin- 4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy; (heteroaryl)$C_1$-$C_3$ alkyloxy; $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano or nitro;

wherein alkyl, alkenyl, alkynyl, cycloalkyl and cycloalkenyl groups are optionally partly or completely fluorinated or mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by $NR^b$, O, S, CO, SO or $SO_2$, and in N-heterocycloalkyl groups a methylene group is optionally replaced by CO or $SO_2$;

each $R^2$ is independently selected from the group consisting of halo, hydroxy, $C_1$-$C_4$ alkyl, $C_3$-$C_{10}$ cycloalkyl, $C_1$-$C_4$ alkyloxy, $C_3$-$C_{10}$ cycloalkyloxy, cyano and nitro, wherein alkyl groups are optionally mono- or polysubstituted by fluorine, and in cycloalkyl groups one or two methylene groups are optionally replaced independently of one another by $NR^b$, O, S, CO, SO or $SO_2$;

$R^3$ is a member selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy)$C_1$-$C_3$ alkyl, $C_5$-$C_{10}$ cycloalkenyl, ($C_5$-$C_{10}$ cycloalkenyl)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_1$-$C_4$ alkyl)carbonyl, aryl, heteroaryl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy; (heteroaryl)$C_1$-$C_3$ alkyloxy; $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano, nitro, ($C_1$-$C_6$ alkyloxy)$C_1$-$C_6$ alkyloxy, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkyloxy, ($C_3$-$C_7$ cycloalkyloxy)$C_2$-$C_4$ alkenyl, ($C_3$-$C_7$ cycloalkyloxy)$C_2$-$C_4$ alkynyl and ($C_3$-$C_7$ cycloalkyloxy)$C_1$-$C_3$ alkyloxy;

wherein alkyl, alkenyl, alkynyl, cycloalkyl and cycloalkenyl groups are optionally partly or completely fluorinated or mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by $NR^b$, O, S, CO, SO or $SO_2$, and in N-heterocycloalkyl groups a methylene group is optionally replaced by CO or $SO_2$;

$R^4$ is a member selected from the group consisting of hydrogen, halo, hydroxy, cyano, nitro, $C_1$-$C_3$ alkyl, $C_3$-$C_{10}$ cycloalkyl, $C_1$-$C_3$ alkoxy, and methyl or methoxy substituted by 1 to 3 fluorine atoms, and in cycloalkyl groups one or two methylene groups are optionally replaced independently of one another by $NR^b$, O, S, CO, SO or $SO_2$; and optionally if $R^3$ and $R^4$ are bound to two adjacent vertices of the phenyl ring, $R^3$ and $R^4$ are optionally joined together to form a $C_3$-$C_5$ alkylene or $C_3$-$C_5$ alkenylene bridge, which is optionally partly or completely fluorinated or mono- or disubstituted by identical or different substituents selected from chlorine, hydroxy, $C_1$-$C_3$ alkoxy and $C_1$-$C_3$ alkyl, and wherein one or two methylene groups of the bridge are optionally replaced independently of one another by O, S, CO, SO, $SO_2$ or $NR^b$, and wherein one or two methyne groups are optionally replaced by an N atom;

$R^5$ is a member selected from the group consisting of hydrogen, halo, hydroxy, cyano, nitro, $C_1$-$C_3$ alkyl, $C_3$-$C_{10}$ cycloalkyl, $C_1$-$C_3$ alkoxy and methyl or methoxy substituted by 1 to 3 fluorine atoms, wherein in cycloalkyl groups one or two methylene groups are optionally replaced independently of one another by $NR^b$, O, S, CO, SO or $SO_2$;

$R^6$, $R^7$, $R^8$ and $R^9$ are each independently selected from the group consisting of hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, hydrogen, halo, $C_1$-$C_6$ alkyl, $C_2$-$C_6$ alkenyl, $C_2$-$C_6$ alkynyl, ($C_3$-$C_{10}$)cycloalkyl-($C_1$-$C_3$)alkyl, ($C_5$-$C_7$)cycloalkenyl-($C_1$-$C_3$)alkyl, aryl-($C_1$-$C_3$)alkyl, heteroaryl-($C_1$-$C_3$)alkyl, $C_1$-$C_6$ alkyloxy, $C_2$-$C_6$ alkenyloxy, $C_2$-$C_6$ alkynyloxy, ($C_3$-$C_7$)cycloalkyloxy, $C_5$-$C_7$ cycloalkenyloxy, aryloxy, heteroaryloxy, ($C_3$-$C_7$)cycloalkyl-($C_1$-$C_3$)alkyloxy, ($C_5$-$C_7$)cycloalkenyl-($C_1$-$C_3$)alkyloxy, aryl-($C_1$-$C_3$)alkyloxy, heteroaryl-($C_1$-$C_3$)alkyloxy, aminocarbonyl, hydroxycarbonyl, ($C_1$-$C_4$ alkyl)alkylaminocarbonyl, di-($C_1$-$C_3$ alkyl)aminocarbonyl, ($C_1$-$C_4$ alkyloxy)carbonyl, aminocarbonyl-($C_1$-$C_3$)alkyl, ($C_1$-$C_4$)alkylaminocarbonyl-($C_1$-$C_3$)alkyl, di-($C_1$-$C_3$ alkyl)aminocarbonyl-($C_1$-$C_3$)alkyl, hydroxycarbonyl-($C_1$-$C_3$)alkyl, ($C_1$-$C_4$ alkyloxy)carbonyl-($C_1$-$C_3$)alkyl, ($C_3$-$C_7$)cycloalkyloxy-($C_1$-$C_3$)alkyl, ($C_5$-$C_7$) cycloalkenyloxy-($C_1$-$C_3$)alkyl, aryloxy-($C_1$-$C_3$)alkyl, heteroaryloxy-($C_1$-$C_3$)alkyl, $C_1$-$C_4$ alkylsulfonyloxy, arylsulfonyloxy, aryl-($C_1$-$C_3$)alkyl-sulfonyloxy, trimethylsilyloxy, t-butyldimethylsilyloxy and cyano;

wherein alkyl, alkenyl, alkynyl, cycloalkyl and cycloalkenyl groups are optionally partly or completely fluorinated or mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by $NR^b$, O, S, CO, SO or $SO_2$;

each $R^b$ is independently selected from the group consisting of H, $C_1$-$C_6$ alkyl, $C_3$-$C_6$ cycloalkyl and ($C_1$-$C_4$ alkyl)carbonyl, wherein the alkyl groups are optionally partly or completely fluorinated;

$R^d$ is a member selected from the group consisting of H, $C_1$-$C_6$ alkyl, ($C_1$-$C_4$ alkyl)carbonyl, $CHR^eR^f$, $SO_2R^e$, C(O)

OR$^e$ and C(O)NR$^e$R$^f$, wherein the alkyl groups are optionally partly or completely fluorinated; and R$^e$ and R$^f$ are each independently selected from the group consisting of H and C$_1$-C$_6$ alkyl, wherein the alkyl groups are optionally partly or completely fluorinated;

and pharmaceutically acceptable salts thereof.

When the following abbreviations and acronyms are used throughout the disclosure, they have the following meanings: 9-BBN, 9-Borabicyclo[3.3.1]nonane; calcd, calculated; CD$_3$OD, methanol-d$_4$; CDCl$_3$, chloroform-d; CH$_2$Cl$_2$, methylene chloride; $^{13}$C NMR, carbon nuclear magnetic resonance; DCE, dichloroethane; DCM, dichloromethane; DEAD, diethyl azodicarboxylate; DIBAL-H, diisobutylaluminum hydride; DMAP, 4-dimethylaminopyridine; DMF, N,N-Dimethylformamide; DMSO, dimethylsulfoxide; ELSD, evaportive light scattering detection; ESI-MS, electrospray ionization mass spectroscopy; EtOAc, ethyl acetate; EtOH, ethanol; h, hour(s); H$_2$, hydrogen gas; HATU, 2-(7-aza-1H-benzotriazole-1-yl)-1,1,3,3-tetramethyluronium hexafluorophosphate; HCl, hydrochloric acid; $^1$H NMR, proton nuclear magnetic resonance; KOH, potassium hydroxide; LC/MS, liquid chromatography/mass spectroscopy; m-CPBA, meta-chloroperoxybenzoic acid; Me, methyl; MeOH, methanol; MHz, megahertz; min, minute(s); mL, milliliter(s); NaH, sodium hydride; NaHCO$_3$, sodium bicarbonate; NaOH, sodium hydroxide; Na$_2$SO$_4$, sodium sulfate; NEt$_3$, triethylamine; Pd/C, palladium on carbon; rt, room temperature; THF, tetrahydrofuran; TLC, thin layer chromatography; TMS, trimethylsilyl.

In the General Synthesis schemes provided below various R groups (e.g., R$^1$ through R$^5$) are shown at fixed positions of the aromatic rings to which each is attached. This illustration is merely provided to simplify the schemes, as one of skill in the art will appreciate that alternative positions are contemplated in the present invention, depending on the starting materials. Additionally, for embodiments of formula I wherein the subscripts s and w are 0, R$^1$ and R$^2$ (as shown below) are hydrogen. Still further, the saccharide portion of the compounds can be modified according to well-known methods (e.g., replacement of hydroxyl groups shown, esterification/etherification of the hydroxyl groups, and the like) and the invention and schemes are not meant to be limited to the illustrated sugar portions.

General Synthesis Method of Scheme I

Inventive compounds of formula 14a can be conveniently prepared according to the reaction sequences as shown in Scheme I (see FIG. 1).

As shown in Scheme I, methoxyaryl 1a can be coupled with benzoyl chloride 2a, either commercially available or prepared in situ from the corresponding benzoic acid, using a Lewis acid, typically AlCl$_3$ or the like, to give benzophenone product 3a. Reduction of 3a can be accomplished by triethylsilane and an appropriate protic or Lewis acid, typically trifluoroacitic acid or borontrifluoroetherate, followed by methyl ether cleavage, typically done using borontribromide, to give phenol 4a.

Suitably protected gluconolactone 5a (typically alkyl or silyl ether protection, preferably benzyl) is treated with the methyltriphenylphosphonium bromide and a suitable alkyl or aryl lithium base to give olefin 6a. Protection of the alcohol with P' gives olefin 7a (preferably by a protecting group orthogonal to P). Epoxidation of the olefin, typically by a peroxyacid, gives epoxide 8a. Base initiated opening of the epoxide with phenol 4a gives phenol ether 9a. Oxidation of the free hydroxyl to the ketone gives 10a. Selective deprotection of P' gives the hemi-acetal 11a. Acid catalyzed methyl glycoside formation, typically with a sulfonic acid or sulfonic acid resin and trimethylorthoformate in methanol, gives 12a. Cyclization initiated by a Lewis acid, typically borontrifluoroetherate, gives 13a. Deprotection of the remaining hydroxyls gives 14a.

General Synthesis Method of Scheme II

Figure 2:
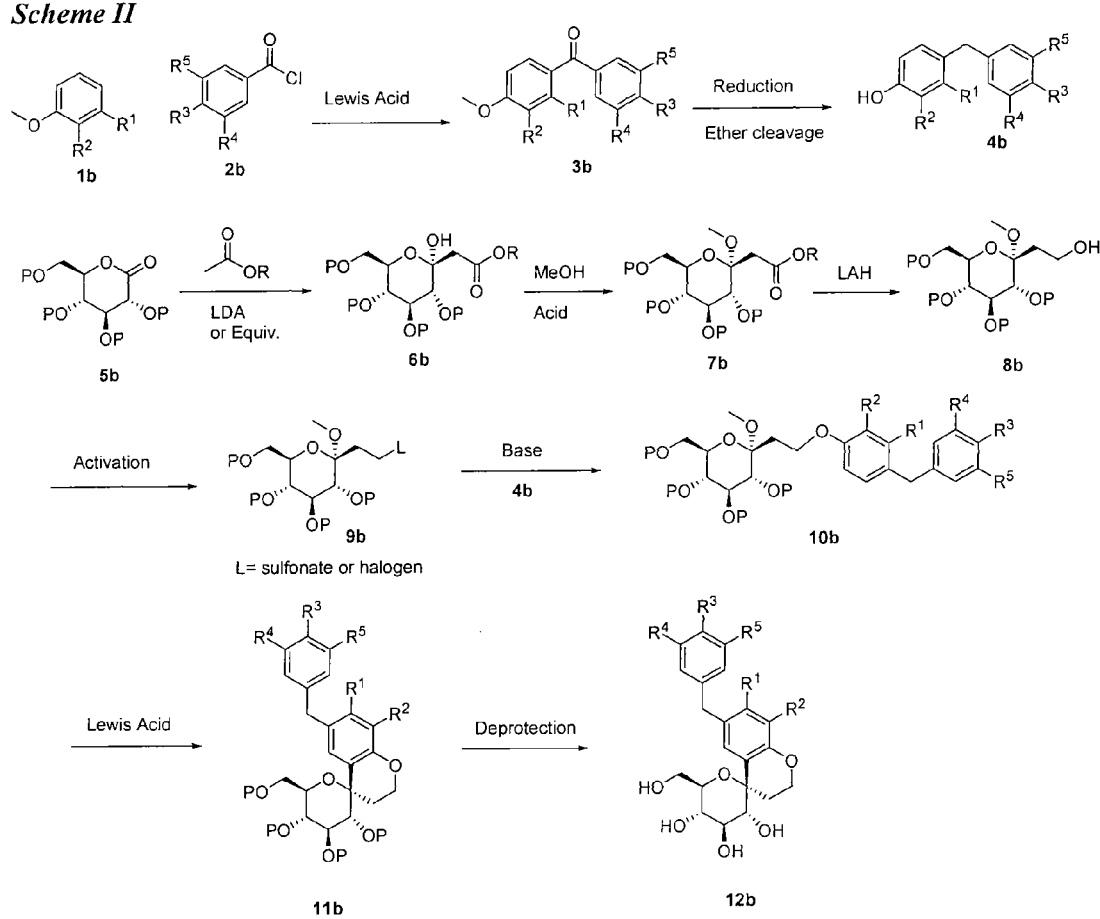

Inventive compounds of formula 12b can be conveniently prepared according to a reaction sequence as shown in Scheme II (see FIG. 2).

As shown in Scheme II, methoxyaryl 1b can be coupled with benzoyl chloride 2b, either commercially available or prepared in situ from the corresponding benzoic acid, using a Lewis acid, typically AlCl$_3$ or the like, to give benzophenone product 3b. Reduction of 3b can be accomplished by triethylsilane and an appropriate protic or Lewis acid, typically trifluoroacitic acid or borontrifluoroetherate, followed by methyl ether cleavage, typically done using borontribromide, to give phenol 4b.

Suitably protected gluconolactone 5b (typically alkyl or silyl ether protection, preferably benzyl) is treated with the lithium anion of an alkyl acetate, typically methyl acetate, generated from an appropriate lithium base, typically lithium diisopropylamide, to generate lactol 6b. Acid catalyzed methyl glycoside formation, typically with a sulfonic acid or sulfonic acid resin and trimethylorthoformate in methanol, gives 7b. Reduction of the ester to the primary hydroxyl by an aluminum hydride or similar reducing agent, preferably lithium aluminum hydride, gives the alcohol 8b. Conversion of the primary hydroxyl to a suitable leaving group L, typically a sulfonate ester, by treatment with the corresponding sulfonyl chloride, or a halogen, by treatment with the corresponding phosphorusoxyhalogen or similar, gives 9b. At this juncture protecting group P maybe changed to an ester protecting group, if desired, by standard de-protection conditions, typically a palladium catalyst and hydrogen for benzyl ether protection, followed by esterification under standard conditions, preferably acetic anhydride and pyridine for acetate protection. Displacement of leaving group L with the phenol 4b under basic conditions gives ether 10b. Cyclization initiated by a Lewis acid, typically borontrifluoroetherate, gives 11b. Deprotection of the remaining hydroxyls under standard conditions, preferably sodium methoxide in methanol for acetate protection or palladium catalyst and hydrogen for benzyl protection, gives 12b.

General Synthesis Method of Scheme III

Figure 3:
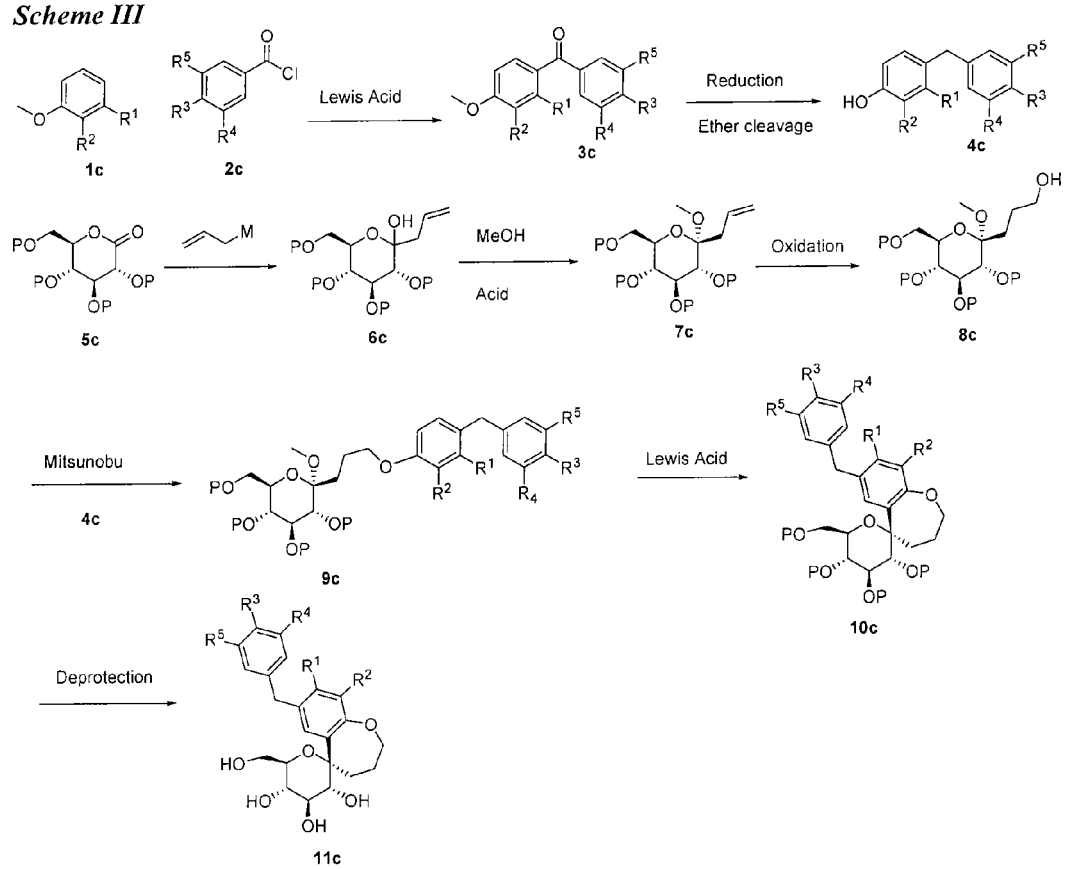

Inventive compounds of formula 11c can be conveniently prepared according to a reaction sequence as shown in Scheme III (see FIG. 3).

As shown in Scheme III, methoxyaryl 1c can be coupled with benzoyl chloride 2c, either commercially available or prepared in situ from the corresponding benzoic acid, using a Lewis acid, typically AlCl$_3$ or the like, to give benzophenone product 3c. Reduction of 3c can be accomplished by triethylsilane and an appropriate protic or Lewis acid, typically trifluoroacitic acid or borontrifluoroetherate, followed by methyl ether cleavage, typically done using borontribromide, to give phenol 4c.

Suitably protected gluconolactone 5c (typically alkyl or silyl ether protection, preferably benzyl) is treated with a metalated allyl, typically magnesium bromide or chloride, or alternatively allyl lithium, to give lactol 6c. Acid catalyzed methyl glycoside formation, typically with a sulfonic acid or sulfonic acid resin and trimethylorthoformate in methanol, gives 7c. Oxidation of the terminal olefine to give the primary hydroxyl, typically with a borane, preferably diborane or 9-BBN, followed by treatment with a peroxide, typically hydrogen peroxide, gives primary alcohol 8c. Treatment of 8c with phenol 4c under standard Mitsunobu coupling conditions, preferably DEAD, or equivalent, and triphenylphosphine, gives ether 9c. Cyclization initiated by a Lewis acid, typically borontrifluoroetherate, gives 10c. Deprotection of the remaining hydroxyls gives 11c.

General Synthesis Method of Scheme IV

Figure 4:
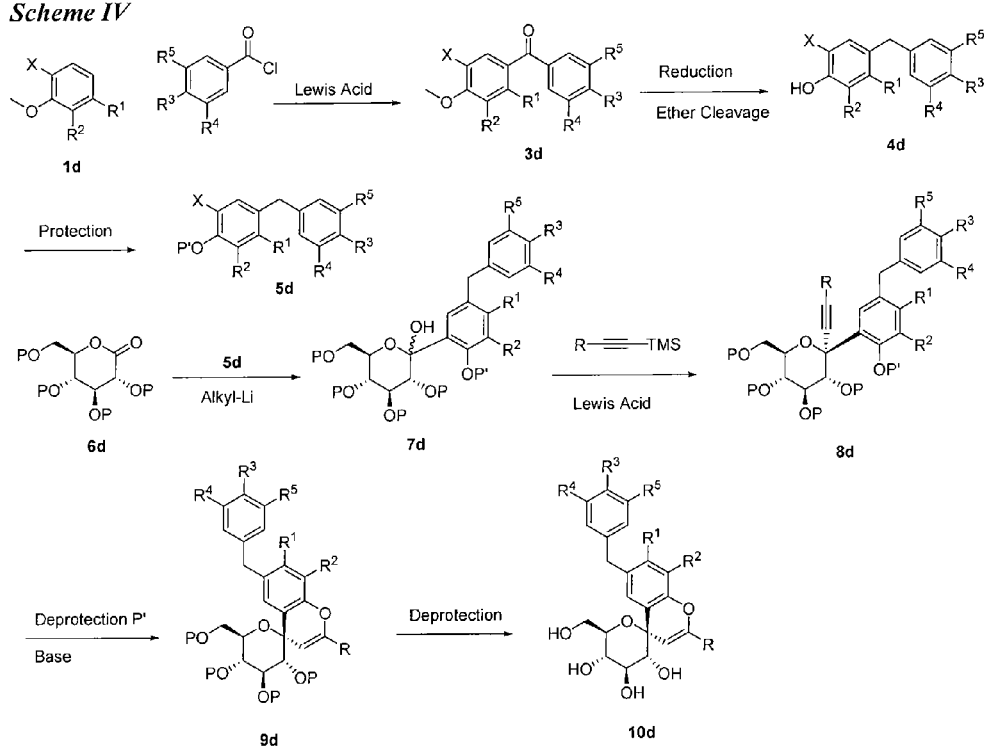

Inventive compounds of formula 10d can be conveniently prepared according to a reaction sequence as shown in Scheme IV (see FIG. 4).

As shown in Scheme IV, methoxyaryl 1d, where X is bromine, iodine or chlorine, preferably bromine, can be coupled with benzoyl chloride 2d, either commercially available or prepared in situ from the corresponding benzoic acid, using a Lewis acid, typically $AlCl_3$ or the like, to give benzophenone product 3d. Reduction of 3d can be accomplished by triethylsilane and an appropriate protic or Lewis acid, typically trifluoroacitic acid or borontrifluoroetherate, followed by methyl ether cleavage, typically done using borontribromide, to give phenol 4d. Suitable protection of the phenol by P', typically an ether or silyl ether, preferably orthogonal to P, gives aryl halide 5d.

Suitably protected gluconolactone 6d (typically alkyl or silyl ether protection, preferably benzyl) is treated with aryl halide 5d, previously converted to any aryl lithiate using an alkyl lithiate, preferably n-butyl lithium, to give 7d. At this point the protecting group P maybe changed to an ester protecting group, preferably acetate. Treatment of 7d with a Lewis acid, preferably borontrifluoroetherate, and a trimethylsilylethyne gives 8d (R denotes halo, $C_1$-$C_6$ alkyl, $C_1$-$C_6$ alkoxy, $C_3$-$C_6$ cycloalkyl, $C_3$-$C_6$ cycloalkyloxy, or ($C_1$-$C_6$ alkoxy)$C_1$-$C_6$ alkyl). Deprotection of P', followed by base treatment produces spirocycle 9d. Global deprotection gives 10d.

General Synthesis Method of Scheme V

Figure 5:
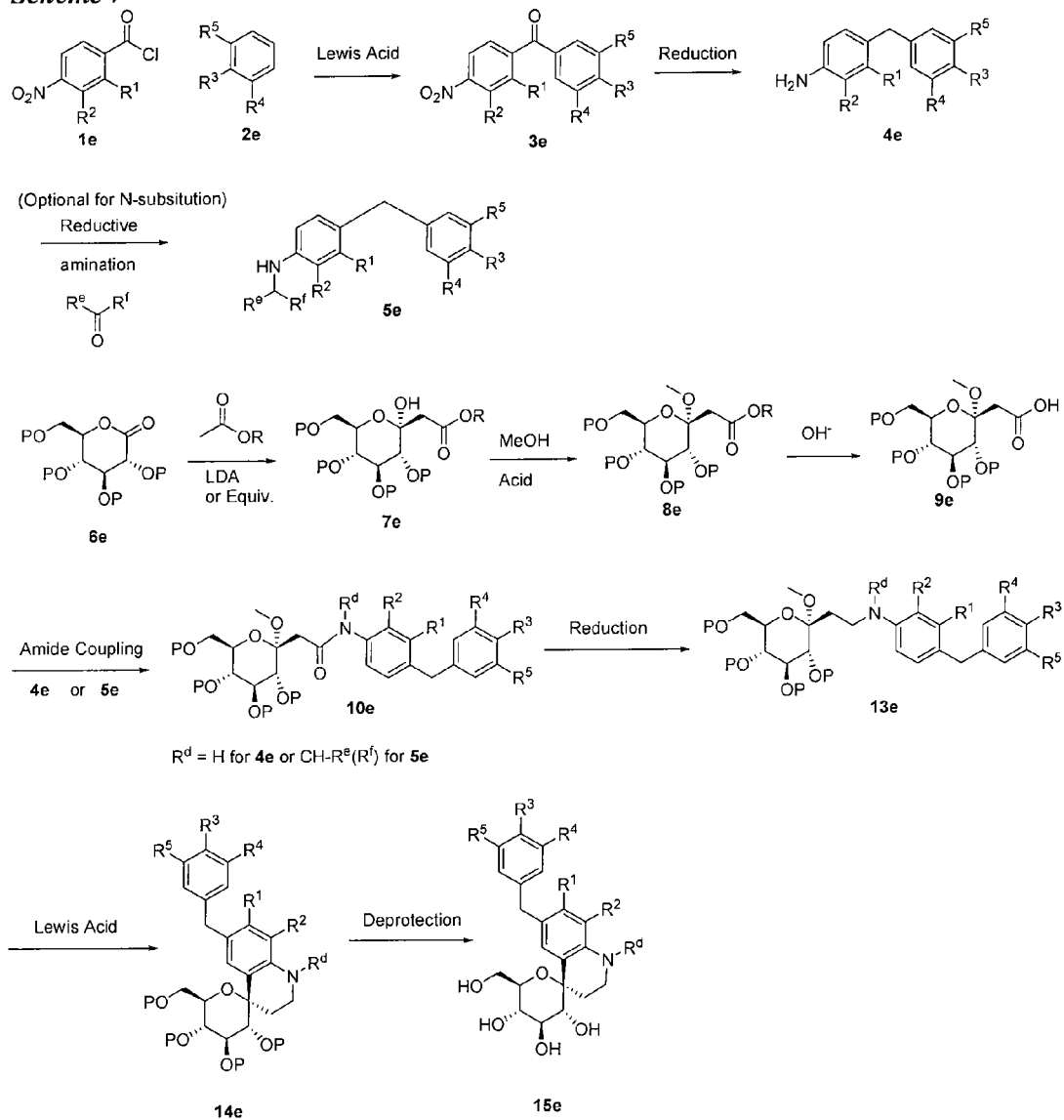

Inventive compounds of formula 15e can be conveniently prepared according to a reaction sequence as shown in Scheme V (see FIG. 5).

As shown in Scheme V, nitrobenzoyl chloride 1e is coupled with aryl 2e using a Lewis acid, typically $AlCl_3$ or the like, to give benzophenone product 3e. Reduction of the ketone of 3e can be accomplished by triethylsilane and an appropriate protic or Lewis acid, typically trifluoroacitic acid or borontrifluoroetherate, followed by nitro reduction, typically done using tin chloride, to give aniline 4e. At this point reductive amination may be done to alkylate the aniline using standard conditions, preferably sodium triacetoxyborohydrie with catalytic acetic acid or titanium tetraisopropoxide, to give aniline 5e. Suitably protected gluconolactone 6e (typically ether or silyl ether protection) is treated with the lithium anion of an alkyl acetate (R denotes alkyl), typically methyl acetate, generated from an appropriate lithium base, typically lithium diisopropylamide, to generate lactol 7e. Acid catalyzed methyl glycoside formation, typically with a sulfonic acid or sulfonic acid resin and trimethylorthoformate in methanol, gives 8e. Hydrolysis of the ester using a metal hydroxide, typically lithium hydroxide, gives carboxylic acid 9e. Amide coupling of acid 9e with either 4e or 5e, using standard coupling reagents, preferably HATU, gives amide 10e. Reduction of the amide to an amine using an aluminum hydride, preferably lithium aluminum hydride, gives 13e. Cyclization initiated by a Lewis acid, typically borontrifluoroetherate, gives 14e. Deprotection of the remaining hydroxyls under standard conditions, preferably palladium catalyst and hydrogen for benzyl protection or tetrabutylammonium fluoride for silyl ethers, gives 15e.

When $R^d$ is H, 15e may be further elaborated by bond forming reactions at the nitrogen. These include, but are not limited to: reductive alkylation (using standard conditions, preferably sodium triacetoxyborohydrie with catalytic acetic acid or titanium tetraisopropoxide) wherein $R^d$ is converted to $C_1$-$C_6$ alkyl, amide bond formation (using standard conditions, preferably HATU and a carboxylic acid, or an acid chloride and suitable base, preferably triethylamine) wherein $R^d$ is converted to ($C_1$-$C_4$ alkyl)carbonyl, sulfonamide formation (typically from a sulfonyl chloride and a base, preferably triethylamine) wherein $R^d$ is converted to $SO_2R^e$, carbamate formation (typically with a alkyl chloroformate and base such as triethylamine) wherein $R^d$ is converted to $C(O)OR^e$, or urea formation (typically with an isocyanate and base such as triethylamine) wherein $R^d$ is converted to $C(O)NR^eR^f$.

General Synthesis Method of Scheme VI

Figure 6:
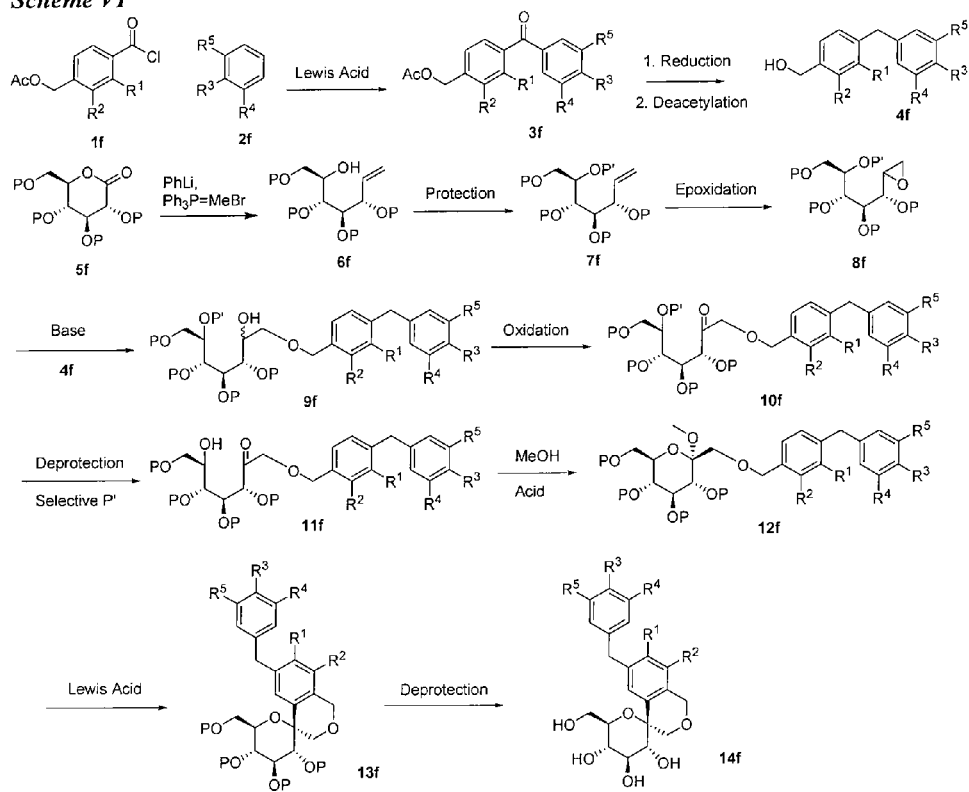

Inventive compounds of formula 14f can be conveniently prepared according to a reaction sequence as shown in Scheme VI (see FIG. 6).

As shown in Scheme VI, benzoyl chloride 1f, either commercially available or prepared in situ from the corresponding benzoic acid, can be coupled with aryl 2f using a Lewis acid, typically $AlCl_3$ or the like, to give benzophenone product 3f. Reduction of 3f can be accomplished by triethylsilane and an appropriate protic or Lewis acid, typically trifluoroacetic acid or borontrifluoroetherate, followed by acetate cleavage, typically done using sodium methoxide, to give benzyl alcohol 4f.

Suitably protected gluconolactone 5f (typically alkyl or silyl ether protection, preferably benzyl) is treated with the methyltriphenylphosphonium bromide and a suitable alkyl or aryl lithium base to give olefin 6f. Protection of the alcohol with P' gives olefin 7f (preferably by a protecting group orthogonal to P). Epoxidation of the olefin, typically by a peroxyacid, give epoxide 8f. At this point protecting group P can be changed to an alternative protecting group if desired. Base initiated opening of the epoxide with benzyl alcohol 4f gives ether 9f. Oxidation of the free hydroxyl to the ketone gives 10f. Selective deprotection of P' gives the hemi-acetal 11f. Acid catalyzed methyl glycoside formation, typically with a sulfonic acid or sulfonic acid resin and trimethylorthoformate in methanol, gives 12f. Cyclization initiated by a Lewis acid, typically borontrifluoroetherate, gives 13f. Deprotection of the remaining hydroxyls gives 14f.

General Synthesis Method of Scheme VII

Figure 7:
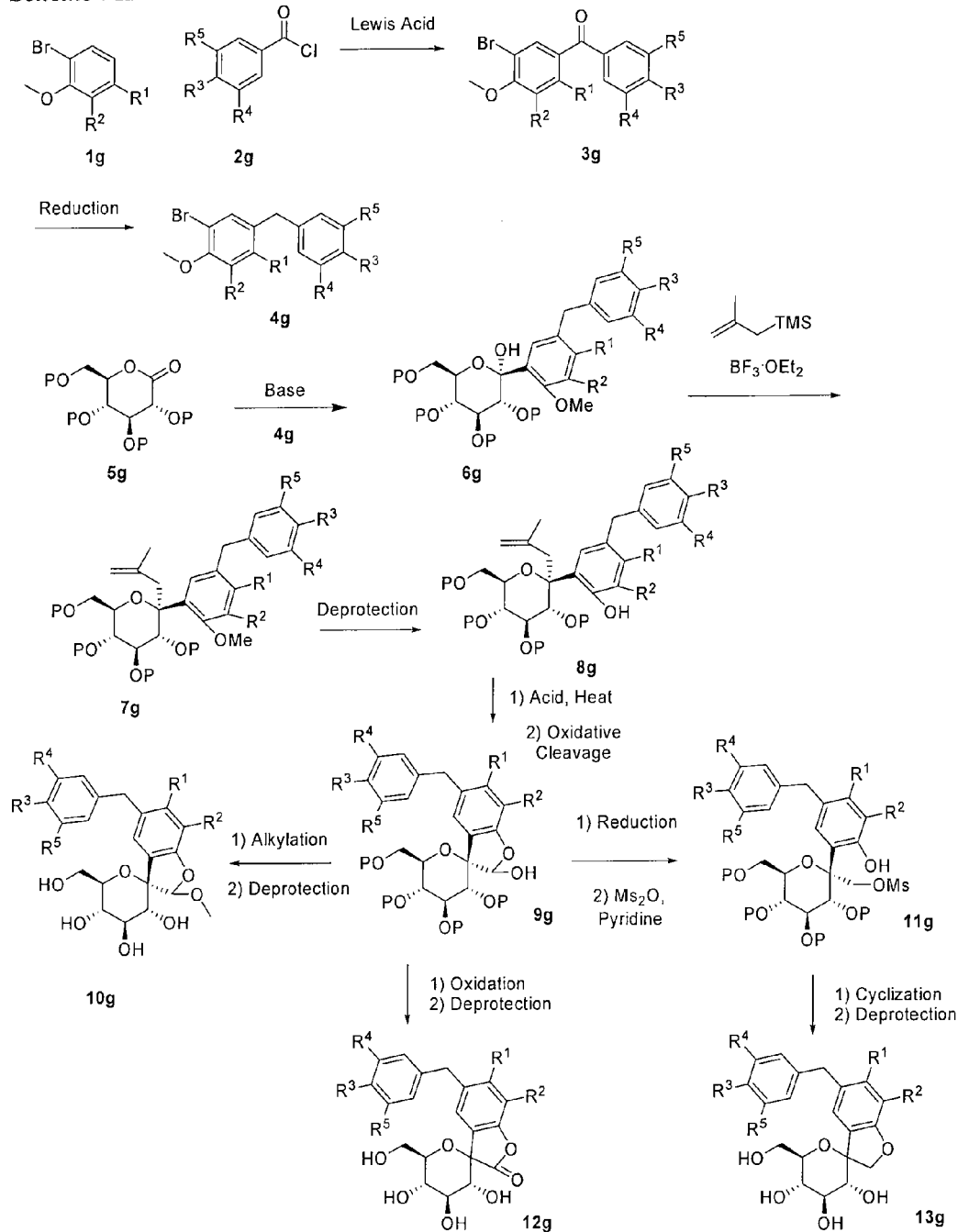

Inventive compounds of formula 12g and 13g can be conveniently prepared according to the reaction sequences as shown in Scheme VII (see FIG. 7).

Methoxyaryl 1g can be coupled with benzoyl chloride 2g, either commercially available or prepared in situ from the corresponding benzoic acid, using a Lewis acid, typically $AlCl_3$ or the like, to give benzophenone product 3g. Reduction of 3g can be accomplished by triethylsilane and an appropriate protic or Lewis acid, typically trifluoroacetic acid or borontrifluoroetherate, to give arylbenzyl 4g.

Suitably protected gluconolactone 5g (typically alkyl or silyl ether protection, preferably benzyl) is treated with 4g and a suitable alkyl or aryl lithium base to give 6g. Reaction of the alcohol with a trimethylsilyl modified alkyl group, typically allyl methyl trimethylsilane, and a Lewis acid, typically boron trifluoroetherate, gives 7g. Methyl ether cleavage, typically by sodium ethane thiol, gives 8g. Migration of the double bond, typically by acid, followed by oxidative cleavage, typically with ozone and triphenyl phosphine, gives 9g. Alkylation of the free hydroxyl, typically by trimethylorthoformate, followed by deprotection, gives 10g. Reduction of the spirofuran, typically with sodium borohydride, followed by mesylation of the primary alcohol, typically with methanesulfonic anhydride, gives 10g. Oxidation of 9g, typically with pyridium chlorochromate, followed by deprotection gives 12g. Cyclization of 11g initiated by a base, typically dimethylaminopyridine, followed by deprotection of the remaining hydroxyls gives 13g.

General Synthesis Method of Scheme VIII

Figure 8:
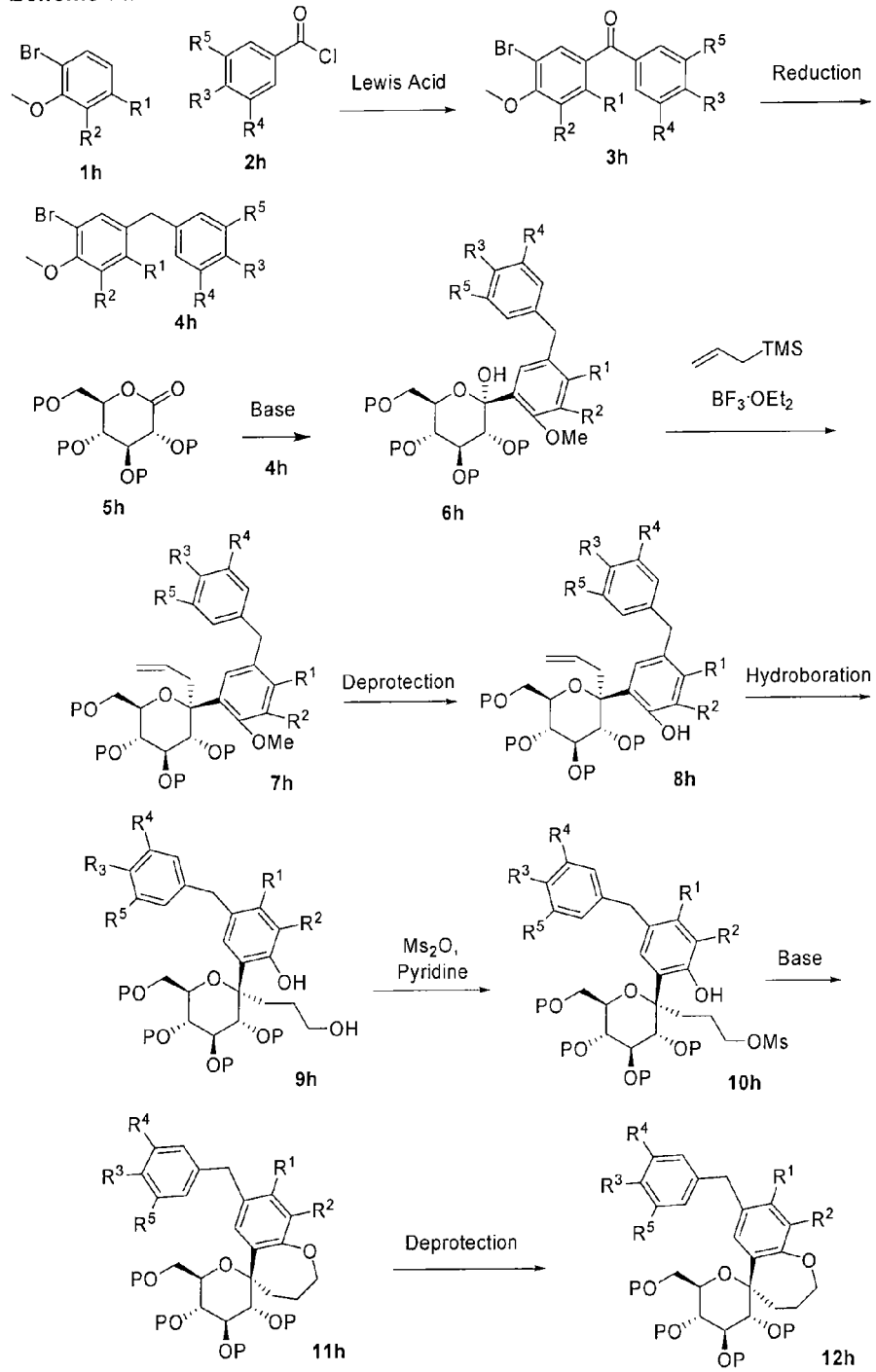

Inventive compounds of formula 12h can be conveniently prepared according to a reaction sequence as shown in Scheme VIII (see FIG. 8).

Methoxyaryl 1h can be coupled with benzoyl chloride 2h, either commercially available or prepared in situ from the corresponding benzoic acid, using a Lewis acid, typically $AlCl_3$ or the like, to give benzophenone product 3h. Reduction of 3h can be accomplished by triethylsilane and an appropriate protic or Lewis acid, typically trifluoroacetic acid or borontrifluoroetherate, to give arylbenzyl 4h. Suitably protected gluconolactone 5h (typically alkyl or silyl ether protection, preferably benzyl) is treated with 4h and a suitable alkyl or aryl lithium base to give 6h. Reaction of the alcohol with a trimethylsilyl modified alkyl group, typically allyl trimethylsilane, and a Lewis acid, typically boron trifluoroetherate, gives 7h. Methyl ether cleavage, typically by sodium ethane thiol, gives 8h. Hydroboration, typically with 9-BBN and hydrogen peroxide, gives 9h. Mesylation of the primary alcohol, typically with methanesulfonic anhydride, gives 10h. Cyclization initiated by a base, typically dimethylaminopyridine, gives 11h. Deprotection of the remaining hydroxyls gives 12h.

General Synthesis Method of Scheme IX

Figure 9:
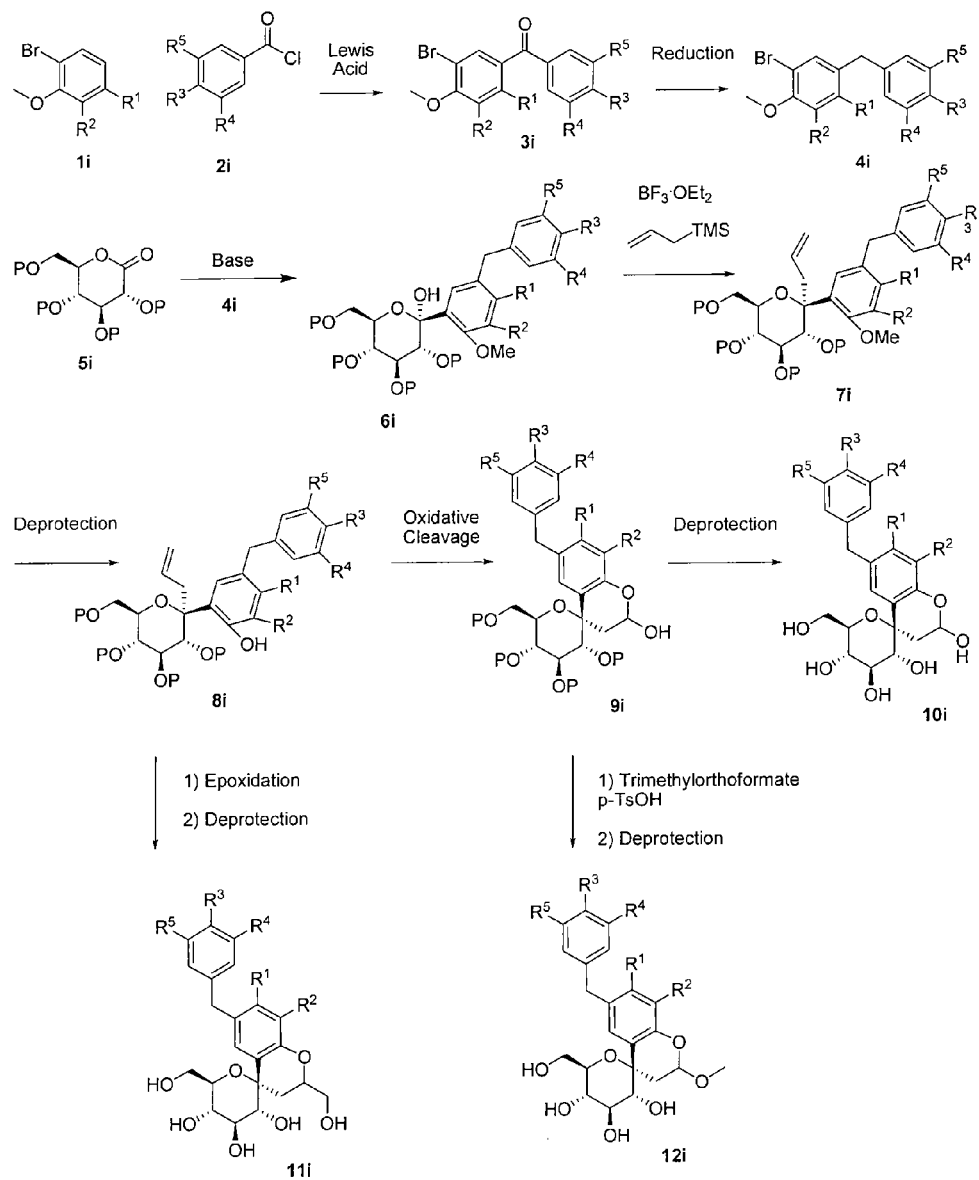

Inventive compounds of formula 11i and 12i can be conveniently prepared according to a reaction sequence as shown in Scheme IX (see FIG. 9).

Methoxyaryl 1i can be coupled with benzoyl chloride 2i, either commercially available or prepared in situ from the corresponding benzoic acid, using a Lewis acid, typically $AlCl_3$ or the like, to give benzophenone product 3i. Reduction of 3i can be accomplished by triethylsilane and an appropriate protic or Lewis acid, typically trifluoroacetic acid or borontrifluoroetherate, to give arylbenzyl 4i. Suitably protected gluconolactone 5i (typically alkyl or silyl ether protection, preferably benzyl) is treated with 4i and a suitable alkyl or aryl lithium base to give 6i. Reaction of the alcohol 6i with a trimethylsilyl modified alkyl derivative, typically allyl trimethylsilane, and a Lewis acid, typically boron trifluoroetherate, gives 7i. Methyl ether cleavage, typically by sodium ethane thiol, gives 8i. Oxidative cleavage of the alkene, typicallyl with ozone and triphenylphosphine, gives 9i. Deprotection of the resulting tetrahydrospirochromane gives 10i. Epoxidation of 8i, preferably with m-CPBA, followed by deprotection gives 11i. Reaction of 9i with trimethylorthoformate and p-toluenesulfonic acid followed by deprotection gives 12i.

General Synthesis Method of Scheme X

Figure 10:
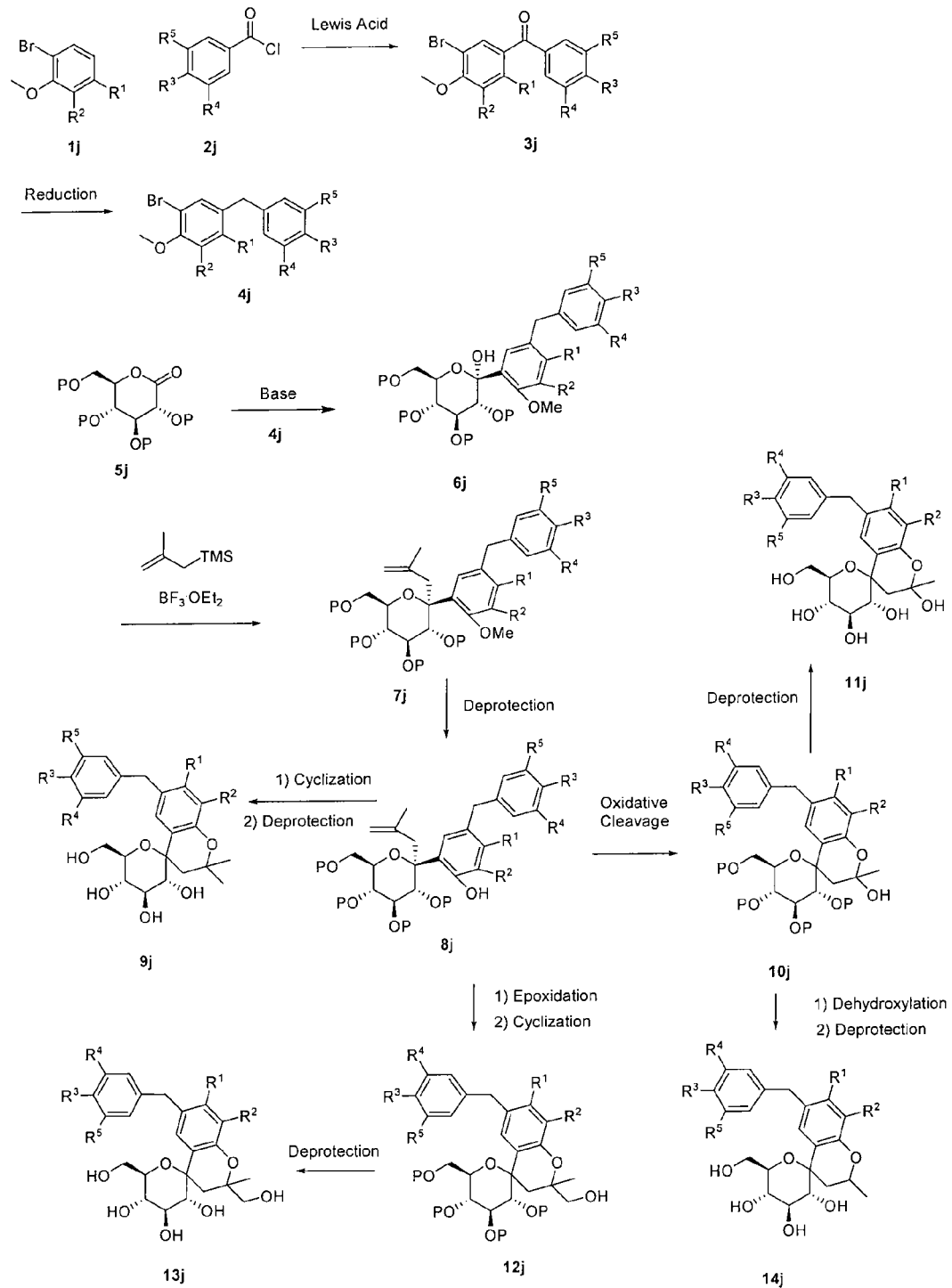

Inventive compounds of formula 13j and 14j can be conveniently prepared according to a reaction sequence as shown in Scheme X (see FIG. 10).

Methoxyaryl 1j can be coupled with benzoyl chloride 2j, either commercially available or prepared in situ from the corresponding benzoic acid, using a Lewis acid, typically $AlCl_3$ or the like, to give benzophenone product 3j. Reduction of 3j can be accomplished by triethylsilane and an appropriate protic or Lewis acid, typically trifluoroacetic acid or borontrifluoroetherate, to give arylbenzyl 4j. Suitably protected gluconolactone 5j (typically alkyl or silyl ether protection, preferably benzyl) is treated with 4j and a suitable alkyl or aryl lithium base to give 6j. Reaction of the alcohol 6j with a trimethylsilyl modified alkyl derivative, typically methylallyl (trimethyl)silane, and a Lewis acid, typically boron trifluoroetherate, gives 7j. Methyl ether cleavage, typically by sodium ethane thiol, gives 8j. Cyclization, typically with silver triflate, followed by deprotection gives 9j. Oxidative cleavage of the alkene, typically with ozone and triphenylphosphine, gives 10j. Deprotection of the resulting spirochromane gives 11j. Epoxidation of 8j, preferably with m-CPBA, followed by cyclization and deprotection gives 13j. Dehydroxylation of 10j, typically with n-butylsilane and tris (pentafluorophenyl)borane, followed by deprotection gives 14j.

Pharmaceutical Compositions and Methods of Use

The present invention further provides a pharmaceutical composition comprising an effective amount of a compound or mixture of compounds of Formula I, or a pharmaceutically acceptable salt or prodrug thereof, in a pharmaceutically acceptable carrier.

A compound of this invention can be incorporated into a variety of formulations for therapeutic administration. More particularly, a compound of the present invention can be formulated into pharmaceutical compositions, together or separately, by formulation with appropriate pharmaceutically acceptable carriers or diluents, and can be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of a compound of the present invention can be achieved in various ways, including oral, buccal, parenteral, intravenous, intradermal (e.g., subcutaneous, intramuscular), transdermal, etc., administration. Moreover, the compound can be administered in a local rather than systemic manner, for example, in a depot or sustained release formulation.

Suitable formulations for use in the present invention are found in *Remington: The Science and Practice of Pharmacy*, 21$^{st}$ Ed., Gennaro, Ed., Lippencott Williams & Wilkins (2003), which is hereby incorporated herein by reference. The pharmaceutical compositions described herein can be manufactured in a manner that is known to those of skill in the art, i.e., by means of conventional mixing, dissolving, granulating, dragee-making, levigating, emulsifying, encapsulating, entrapping or lyophilizing processes. The following methods and excipients are merely exemplary and are in no way limiting.

In one preferred embodiment, a compound of the present invention is prepared for delivery in a sustained-release, controlled release, extended-release, timed-release or delayed-release formulation, for example, in semipermeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the compounds over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

The sustained or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering a compound of the present invention include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080 and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817 and 5,296,483, each of which is hereby incorporated herein by reference. Those skilled in the art will readily recognize other applicable sustained release formulations.

For oral administration, a compound of the present invention can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. For injection, the compound can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, a compound of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

Systemic administration can also be by transmucosal or transdermal means. For transmucosal or transdermal administration, penetrants appropriate to the barrier to be permeated are used in the formulation. For topical administration, the agents are formulated into ointments, creams, salves, powders and gels. In one embodiment, the transdermal delivery agent can be DMSO. Transdermal delivery systems can include, e.g., patches. For transmucosal administration, penetrants appropriate to the barrier to be permeated are used in the formulation. Such penetrants are generally known in the art. Exemplified transdermal delivery formulations that can find use in the present invention include those described in U.S. Pat. Nos. 6,589,549; 6,544,548; 6,517,864; 6,512,010; 6,465,006; 6,379,696; 6,312,717 and 6,310,177, each of which are hereby incorporated herein by reference.

For buccal administration, the compositions can take the form of tablets or lozenges formulated in conventional manner.

In addition to the formulations described previously, a compound of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The present invention also contemplates pharmaceutical compositions comprising the compounds of Formula I in admixture with an effective amount of other therapeutic agents as combination partners, particularly those used for treating diseases and conditions which can be affected by SGLT inhibition, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. An effective amount of the compound and/or combination partner will, of course, be dependent on the subject being treated, the severity of the affliction and the manner of administration. Determination of an effective amount is well within the capability of those skilled in the art, especially in light of the detailed disclosure provided herein. Generally, an efficacious or effective amount of a compound is determined by first administering a low dose or small amount, and then incrementally increasing the administered dose or dosages until a desired therapeutic effect is observed in the treated subject, with minimal or no toxic side effects. Applicable methods for determining an appropriate dose and dosing schedule for administration of the present invention are described, for example, in *Goodman and Gilman's The Pharmacological Basis of Therapeutics*, 11$^{th}$ Ed., Brunton, Lazo and Parker, Eds., McGraw-Hill (2006), and in *Remington: The Science and Practice of Pharmacy*, 21$^{st}$ Ed., Gennaro, Ed., Lippencott Williams & Wilkins (2003), both of which are hereby incorporated herein by reference.

The present invention further provides methods of using the compounds of Formula I for the prevention and treatment of disease. In one embodiment the invention provides a method of treating type 1 and type 2 diabetes mellitus, hyperglycemia, diabetic complications (such as retinopathy, nephropathy, neuropathy, ulcers, micro- and macroangiopathies, gout and diabetic foot disease), insulin resistance, metabolic syndrome (Syndrome X), hyperinsulinemia, hypertension, hyperuricemia, obesity, edema, dyslipidemia, chronic heart failure, atherosclerosis and related diseases, which comprises administering an effective amount of a compound or mixture of compounds of Formula I, or a pharmaceutically acceptable salt or prodrug thereof, to a subject in need thereof. In another embodiment the invention provides a method of using a compound or mixture of compounds of Formula I, or a pharmaceutically acceptable salt or prodrug thereof, for the preparation of a medicament for treating type 1 and type 2 diabetes mellitus, hyperglycemia, diabetic complications, insulin resistance, metabolic syndrome, hyperinsulinemia, hypertension, hyperuricemia, obesity, edema, dyslipidemia, chronic heart failure, atherosclerosis and related diseases.

The present invention also contemplates the use of the compounds of Formula I, or pharmaceutically acceptable salts or prodrugs thereof, in combination with other therapeutic agents, particularly those used for treating the above-mentioned diseases and conditions, such as antidiabetic agents, lipid-lowering/lipid-modulating agents, agents for treating diabetic complications, anti-obesity agents, antihypertensive agents, antihyperuricemic agents, and agents for treating chronic heart failure, atherosclerosis or related disorders. Those skilled in the art will appreciate that other therapeutic agents discussed below can have multiple therapeutic uses and the listing of an agent in one particular category should not be construed to limit in any way its usefulness in combination therapy with compounds of the present invention.

Examples of antidiabetic agents suitable for use in combination with compounds of the present invention include insulin and insulin mimetics, sulfonylureas (such as acetohexamide, carbutamide, chlorpropamide, glibenclamide, glibomuride, gliclazide, glimepiride, glipizide, gliquidone, glisoxepide, glyburide, glyclopyramide, tolazamide, tolcyclamide, tolbutamide and the like), insulin secretion enhancers (such as JTT-608, glybuzole and the like), biguanides (such as metformin, buformin, phenformin and the like), sulfonylurea/biguanide combinations (such as glyburide/metformin and the like), meglitinides (such as repaglinide, nateglinide, mitiglinide and the like), thiazolidinediones (such as rosiglitazone, pioglitazone, isaglitazone, netoglitazone, rivoglitazone, balaglitazone, darglitazone, CLX-0921 and the like), thiazolidinedione/biguanide combinations (such as pioglitazone/metformin and the like), oxadiazolidinediones (such as YM440 and the like), peroxisome proliferator-activated receptor (PPAR)-gamma agonists (such as farglitazar, metaglidasen, MBX-2044, GI 262570, GW1929, GW7845 and the like), PPAR-alpha/gamma dual agonists (such as muraglitazar, naveglitazar, tesaglitazar, peliglitazar, JTT-501, GW-409544, GW-501516 and the like), PPAR-alpha/gamma/delta pan agonists (such as PLX204, GlaxoSmithKline 625019, GlaxoSmithKline 677954 and the like), retinoid X receptor agonists (such as ALRT-268, AGN-4204, MX-6054, AGN-194204, LG-100754, bexarotene and the like), alpha-glucosidase inhibitors (such as acarbose, miglitol and the like), stimulants of insulin receptor tyrosine kinase (such as TER-17411, L-783281, KRX-613 and the like), tripeptidyl peptidase II inhibitors (such as UCL-1397 and the like), dipeptidyl peptidase IV inhibitors (such as sitagliptin, vildagliptin, denagliptin, saxagliptin, NVP-DPP728, P93/01, P32/98, FE 99901, TS-021, TSL-225, GRC8200, compounds described in U.S. Pat. Nos. 6,869,947; 6,727,261; 6,710,040; 6,432,969; 6,172,081; 6,011,155 and the like), protein tyrosine phosphatase-1B inhibitors (such as KR61639, IDD-3, PTP-3848, PTP-112, OC-86839, PNU-177496, compounds described in Vats, R. K., et al., *Current Science, Vol.* 88, No. 2, 25 Jan. 2005, pp. 241-249, and the like), glycogen phosphorylase inhibitors (such as N,N-4201, CP-368296 and the like), glucose-6-phosphatase inhibitors, fructose 1,6-bisphosphatase inhibitors (such as CS-917, MB05032 and the like), pyruvate dehydrogenase inhibitors (such as AZD-7545 and the like), imidazoline derivatives (such as BL11282 and the like), hepatic gluconeogenesis inhibitors (such as FR-225659 and the like), D-chiroinositol, glycogen synthase kinase-3 inhibitors (such as compounds described in Vats, R. K., et al., *Current Science, Vol.* 88, No. 2, 25 Jan. 2005, pp. 241-249, and the like), incretin mimetics (such as exenatide and the like), glucagon receptor antagonists (such as BAY-27-9955, N,N-2501, NNC-92-1687 and the like), glucagon-like peptide-1 (GLP-1), GLP-1 analogs (such as liraglutide, CJC-1131, AVE-0100 and the like), GLP-1 receptor agonists (such as AZM-134, LY-315902, GlaxoSmithKline 716155 and the like), amylin, amylin analogs and agonists (such as pramlintide and the like), fatty acid binding protein (aP2) inhibitors (such as compounds described in U.S. Pat. Nos. 6,984,645; 6,919,323; 6,670,380; 6,649,622; 6,548,529 and the like), beta-3 adrenergic receptor agonists (such as solabegron, CL-316243, L-771047, FR-149175 and the like), and other insulin sensitivity enhancers (such as reglixane, ONO-5816, MBX-102, CRE-1625, FK-614, CLX-0901, CRE-1633, N,N-2344, BM-13125, BM-501050, HQL-975, CLX-0900, MBX-668, MBX-675, S-15261, GW-544, AZ-242, LY-510929, AR-H049020, GW-501516 and the like).

Examples of agents for treating diabetic complications suitable for use in combination with compounds of the present invention include aldose reductase inhibitors (such as epalrestat, imirestat, tolrestat, minalrestat, ponalrestat, zopolrestat, fidarestat, ascorbyl gamolenate, ADN-138, BAL-AR18, ZD-5522, ADN-311, GP-1447, IDD-598, risarestat, zenarestat, methosorbinil, AL-1567, M-16209, TAT, AD-5467, AS-3201, NZ-314, SG-210, JTT-811, lindolrestat, sorbinil and the like), inhibitors of advanced glycation endproducts (AGE) formation (such as pyridoxamine, OPB-9195, ALT-946, ALT-711, pimagedine and the like), AGE breakers (such as ALT-711 and the like), sulodexide, 5-hydroxy-1-methylhydantoin, insulin-like growth factor-I, platelet-derived growth factor, platelet-derived growth factor analogs, epidermal growth factor, nerve growth factor, uridine, protein kinase C inhibitors (such as ruboxistaurin, midostaurin and the like), sodium channel antagonists (such as mexiletine, oxcarbazepine and the like), nuclear factor-kappaB (NF-kappaB) inhibitors (such as dexlipotam and the like), lipid peroxidase inhibitors (such as tirilazad mesylate and the like), N-acetylated-alpha-linked-acid-dipeptidase inhibitors (such as GPI-5232, GPI-5693 and the like), and carnitine derivatives (such as carnitine, levacecamine, levocarnitine, ST-261 and the like).

Examples of antihyperuricemic agents suitable for use in combination with compounds of the present invention include uric acid synthesis inhibitors (such as allopurinol, oxypurinol and the like), uricosuric agents (such as probenecid, sulfinpyrazone, benzbromarone and the like) and urinary alkalinizers (such as sodium hydrogen carbonate, potassium citrate, sodium citrate and the like).

Examples of lipid-lowering/lipid-modulating agents suitable for use in combination with compounds of the present invention include hydroxymethylglutaryl coenzyme A reductase inhibitors (such as acitemate, atorvastatin, bervastatin, carvastatin, cerivastatin, colestolone, crilvastatin, dalvastatin, fluvastatin, glenvastatin, lovastatin, mevastatin, nisvastatin, pitavastatin, pravastatin, ritonavir, rosuvastatin, saquinavir, simvastatin, visastatin, SC-45355, SQ-33600, CP-83101, BB-476, L-669262, S-2468, DMP-565, U-20685, BMS-180431, BMY-21950, compounds described in U.S. Pat. Nos. 5,753,675; 5,691,322; 5,506,219; 4,686,237; 4,647,576; 4,613,610; 4,499,289 and the like), fibric acid derivatives (such as gemfibrozil, fenofibrate, bezafibrate, beclobrate, binifibrate, ciprofibrate, clinofibrate, clofibrate, etofibrate, nicofibrate, pirifibrate, ronifibrate, simfibrate, theofibrate, AHL-157 and the like), PPAR-alpha agonists (such as GlaxoSmithKline 590735 and the like), PPAR-delta agonists (such as GlaxoSmithKline 501516 and the like), acyl-coenzyme A:cholesterol acyltransferase inhibitors (such as avasimibe, eflucimibe, eldacimibe, lecimibide, NTE-122, MCC-147, PD-132301-2, CI-1011, DUP-129, U-73482, U-76807, TS-962, RP-70676, P-06139, CP-113818, RP-73163, FR-129169, FY-038, EAB-309, KY-455, LS-3115, FR-145237, T-2591, J-104127, R-755, FCE-27677, FCE-28654, YIC-C8-434, CI-976, RP-64477, F-1394, CS-505, CL-283546, YM-17E, 447C88, YM-750, E-5324, KW-3033, HL-004 and the like), probucol, thyroid hormone receptor agonists (such as liothyronine, levothyroxine, KB-2611, GC-1 and the like), cholesterol absorption inhibitors (such as ezetimibe, SCH48461 and the like), lipoprotein-associated phospholipase A2 inhibitors (such as rilapladib, darapladib and the like), microsomal triglyceride transfer protein inhibitors (such as CP-346086, BMS-201038, compounds described in U.S. Pat. Nos. 5,595,872; 5,739,135; 5,712,279; 5,760,246; 5,827,875; 5,885,983; 5,962,440; 6,197,798; 6,617,325; 6,821,967; 6,878,707 and the like), low density lipoprotein receptor activators (such as LY295427, MD-700 and the like), lipoxygenase inhibitors (such as compounds described in WO 97/12615, WO 97/12613, WO 96/38144 and the like), carnitine palmitoyl-transferase inhibitors (such as etomoxir and the like), squalene synthase inhibitors (such as YM-53601, TAK-475, SDZ-268-198, BMS-188494, A-87049, RPR-101821, ZD-9720, RPR-107393, ER-27856, compounds described in U.S. Pat. Nos. 5,712,396; 4,924,024; 4,871,721 and the like), nicotinic acid derivatives (such as acipimox, nicotinic acid, ricotinamide, nicomol, niceritrol, nicorandil and the like), bile acid sequestrants (such as colestipol, cholestyramine, colestilan, colesevelam, GT-102-279 and the like), sodium/bile acid cotransporter inhibitors (such as 264W94, S-8921, SD-5613 and the like), and cholesterol ester transfer protein inhibitors (such as torcetrapib, JTT-705, PNU-107368E, SC-795, CP-529414 and the like).

Examples of anti-obesity agents suitable for use in combination with compounds of the present invention include serotonin-norepinephrine reuptake inhibitors (such as sibutramine, milnacipran, mirtazapine, venlafaxine, duloxetine, desvenlafaxine and the like), norepinephrine-dopamine reuptake inhibitors (such as radafaxine, bupropion, amineptine and the like), selective serotonin reuptake inhibitors (such as citalopram, escitalopram, fluoxetine, fluvoxamine, paroxetine, sertraline and the like), selective norepinephrine reuptake inhibitors (such as reboxetine, atomoxetine and the like), norepinephrine releasing stimulants (such as rolipram, YM-992 and the like), anorexiants (such as amphetamine, methamphetamine, dextroamphetamine, phentermine, benzphetamine, phendimetrazine, phenmetrazine, diethylpropion, mazindol, fenfluramine, dexfenfluramine, phenylpropanolamine and the like), dopamine agonists (such as ER-230, doprexin, bromocriptine mesylate and the like), $H_3$-histamine antagonists (such as impentamine, thioperamide, ciproxifan, clobenpropit, GT-2331, GT-2394, A-331440, and the like), 5-HT2c receptor agonists (such as 1-(m-chlorophenyl)piperazine (m-CPP), mirtazapine, APD-356 (lorcaserin), SCA-136 (vabicaserin), ORG-12962, ORG-37684, ORG-36262, ORG-8484, Ro-60-175, Ro-60-0332, VER-3323, VER-5593, VER-5384, VER-8775, LY-448100, WAY-161503, WAY-470, WAY-163909, BVT.933, YM-348, IL-639, IK-264, ATH-88651, ATHX-105 and the like (see, e.g., Nilsson B M, *J. Med. Chem.* 2006, 49:4023-4034)), beta-3 adrenergic receptor agonists (such as L-796568, CGP 12177, BRL-28410, SR-58611A, 1CI-198157, ZD-2079, BMS-194449, BRL-37344, CP-331679, CP-331648, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like), cholecystokinin agonists (such as SR-146131, SSR-125180, BP-3.200, A-71623, FPL-15849, GI-248573, GW-7178, GI-181771, GW-7854, A-71378 and the like), antidepressant/acetylcholinesterase inhibitor combinations (such as venlafaxine/rivastigmine, sertraline/galanthamine and the like), lipase inhibitors (such as orlistat, ATL-962 and the like), anti-epileptic agents (such as topiramate, zonisamide and the like), leptin, leptin analogs and leptin receptor agonists (such as LY-355101 and the like), neuropeptide Y (NPY) receptor antagonists and modulators (such as SR-120819-A, PD-160170, NGD-95-1, BIBP-3226, 1229-U-91, CGP-71683, BIBO-3304, CP-671906-01, J-115814 and the like), ciliary neurotrophic factor (such as Axokine and the like), thyroid hormone receptor-beta agonists (such as KB-141, GC-1, GC-24, GB98/284425 and the like), cannabinoid CB1 receptor antagonists (such as rimonabant, SR147778, SLV 319 and the like (see, e.g., Antel J et al., *J. Med. Chem.* 2006, 49:4008-4016)), melanin-concentrating hormone receptor antagonists (including GlaxoSmithKline 803430X, GlaxoSmithKline 856464, SNAP-7941, T-226296 and the like (see, e.g., Handlon A L and Zhou H, *J. Med. Chem.* 2006, 49:4017-4022)), melanocortin-4 receptor agonists (including PT-15, Ro27-3225, THIQ, NBI 55886, NBI 56297, NBI 56453, NBI 58702, NBI 58704, MB243 and the like (see, e.g., Nargund R P et al., *J. Med. Chem.* 2006, 49:4035-4043)), selective muscarinic receptor $M_1$ antagonists (such as telenzepine, pirenzepine and the like), and combinations thereof.

Examples of antihypertensive agents and agents for treating chronic heart failure, atherosclerosis or related diseases suitable for use in combination with compounds of the present invention include bimoclomol, angiotensin-converting enzyme inhibitors (such as captopril, enalapril, fosinopril, lisinopril, perindopril, quinapril, ramipril and the like), neutral endopeptidase inhibitors (such as thiorphan, omapatrilat, MDL-100240, fasidotril, sampatrilat, GW-660511, mixanpril, SA-7060, E-4030, SLV-306, ecadotril and the like), angiotensin II receptor antagonists (such as candesartan cilexetil, eprosartan, irbesartan, losartan, olmesartan medoxomil, telmisartan, valsartan, tasosartan, enoltasosartan and the like), endothelin-converting enzyme inhibitors (such as CGS 35066, CGS 26303, CGS-31447, SM-19712 and the like), endothelin receptor antagonists (such as tracleer, sitaxsentan, ambrisentan, L-749805, TBC-3214, BMS-182874, BQ-610, TA-0201, SB-215355, PD-180988, BMS-193884, darusentan, TBC-3711, bosentan, tezosentan, J-104132, YM-598, S-0139, SB-234551, RPR-118031A, ATZ-1993, RO-61-1790, ABT-546, enlasentan, BMS-207940 and the like), diuretic agents (such as hydrochlorothiazide, bendroflumethiazide, trichlormethiazide, indapamide, metolazone, furosemide, bumetanide, torsemide, chlorthalidone, metolazone, cyclopenthiazide, hydroflumethiazide, tripamide, mefruside, benzylhydrochlorothiazide, penflutizide, methyclothiazide, azosemide, etacrynic acid, torasemide, piretanide, meticrane, potassium canrenoate, spironolactone, triamterene, aminophylline, cicletanine, LLU-alpha, PNU-80873A, isosorbide, D-mannitol, D-sorbitol, fructose, glycerin, acetazolamide, methazolamide, FR-179544, OPC-31260, lixivaptan, conivaptan and the like), calcium channel antagonists (such as amlodipine, bepridil, diltiazem, felodipine, isradipine, nicardipen, nimodipine, verapamil, S-verapamil, aranidipine, efonidipine, bamidipine, benidipine, manidipine, cilnidipine, nisoldipine, nitrendipine, nifedipine, nilvadipine, felodipine, pranidipine, lercanidipine, isradipine, elgodipine, azelnidipine, lacidipine, vatanidipine, lemildipine, diltiazem, clentiazem, fasudil, bepridil, gallopamil and the like), vasodilating antihypertensive agents (such as indapamide, todralazine, hydralazine, cadralazine, budralazine and the like), beta blockers (such as acebutolol, bisoprolol, esmolol, propanolol, atenolol, labetalol, carvedilol, metoprolol and the like), sympathetic blocking agents (such as amosulalol, terazosin, bunazosin, prazosin, doxazosin, propranolol, atenolol, metoprolol, carvedilol, nipradilol, celiprolol, nebivolol, betaxolol, pindolol, tertatolol, bevantolol, timolol, carteolol, bisoprolol, bopindolol, nipradilol, penbutolol, acebutolol, tilisolol, nadolol, urapidil, indoramin and the like), alpha-2-adrenoceptor agonists (such as clonidine, methyldopa, CHF-1035, guanabenz acetate, guanfacine, moxonidine, lofexidine, talipexole and the like), centrally acting antihypertensive agents (such as reserpine and the like), thrombocyte aggregation inhibitors (such as warfarin, dicumarol, phenprocoumon, acenocoumarol, anisindione, phenindione, ximelagatran and the like), and anti-platelets agents (such as aspirin, clopidogrel, ticlopidine, dipyridamole, cilostazol, ethyl icosapentate, sarpogrelate, dilazep, trapidil, beraprost and the like).

Furthermore, in another aspect, the invention provides for a pharmaceutical composition comprising effective amounts of a compound or mixture of compounds of Formula I, or a pharmaceutically acceptable salt or prodrug thereof, and at least one member selected from the group of therapeutic agents listed above as combination partners, in a pharmaceutically acceptable carrier.

The treatment of the present invention can be administered prophylactically to prevent or delay the onset or progression of a disease or condition (such as hyperglycemia), or therapeutically to achieve a desired effect (such as a desired level of serum glucose) for a sustained period of time.

The compounds of the present invention can be administered to a subject, e.g., a human patient, a domestic animal such as a cat or a dog, independently or together with a combination partner, in the form of their pharmaceutically acceptable salts or prodrugs, or in the form of a pharmaceutical composition where the compounds and/or combination partners are mixed with suitable carriers or excipient(s) in a therapeutically effective amount. Consequently, a compound or mixture of compounds of Formula I, or a pharmaceutically acceptable salt or prodrug thereof, and an additional active agent to be combined therewith, can be present in a single formulation, for example a capsule or tablet, or in two separate formulations, which can be the same or different, for example, in the form of a kit comprising selected numbers of doses of each agent.

The appropriate dosage of compound will vary according to the chosen route of administration and formulation of the composition, among other factors, such as patient response. The dosage can be increased or decreased over time, as required by an individual patient. A patient initially may be given a low dose, which is then increased to an efficacious dosage tolerable to the patient. Typically, a useful dosage for adults may be from 1 to 2000 mg, preferably 1 to 200 mg, when administered by oral route, and from 0.1 to 100 mg, preferably 1 to 30 mg, when administered by intravenous route, in each case administered from 1 to 4 times per day. When a compound of the invention is administered in combination with another therapeutic agent, a useful dosage of the combination partner may be from 20% to 100% of the normally recommended dose.

Dosage amount and interval can be adjusted individually to provide plasma levels of the active compounds which are sufficient to maintain therapeutic effect. Preferably, therapeutically effective serum levels will be achieved by administering single daily doses, but efficacious multiple daily dose schedules are included in the invention. In cases of local administration or selective uptake, the effective local concentration of the drug may not be related to plasma concentration. One having skill in the art will be able to optimize therapeutically effective local dosages without undue experimentation.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims. The invention will be described in greater detail by way of specific examples.

The following examples are offered for illustrative purposes, and are not intended to limit the invention in any manner. Those of skill in the art will readily recognize a variety of noncritical parameters which can be changed or modified to yield essentially the same results.

EXAMPLES

The names of compounds shown in the following examples were derived from the structures shown using the Cambridge-Soft Struct=Name algorithm as implemented in ChemDraw Ultra version 10.0. The structures of compounds synthesized in the examples below were confirmed using the following procedures: LCMS data for intermediates and the final products were obtained using a Phenomenex Gemini 5 μm C18 column (50×4.6 mm). Mobile phase A: 0.05% aqueous formic acid; mobile phase B: 0.05% formic acid in MeCN. Gradient 5% B to 100% B over 3 min; flow rate 2 mL/min, ambient temperature. 1HNMR data were acquired on a Varian Mercury 300 spectrometer at 300 MHz, with chemical shifts referenced to internal TMS.

Example 1

Synthesis of (2'S,3'R,4'S,5'S,6'R)-6-(4-ethylbenzyl)-6'-(hydroxymethyl)-3',4',5',6'-tetrahydrospiro[chroman-4,2'-pyran]-3',4',5'-triol (Compound 12)

Figure 11:
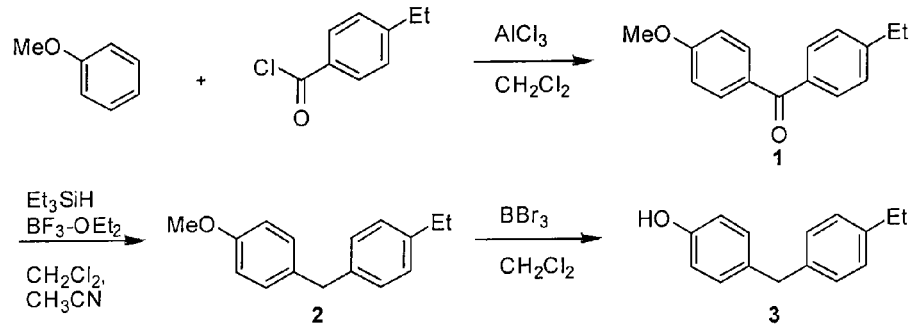
FIGS. 11-18 provide synthesis schemes for compounds provided in the Examples.
Figure 11:
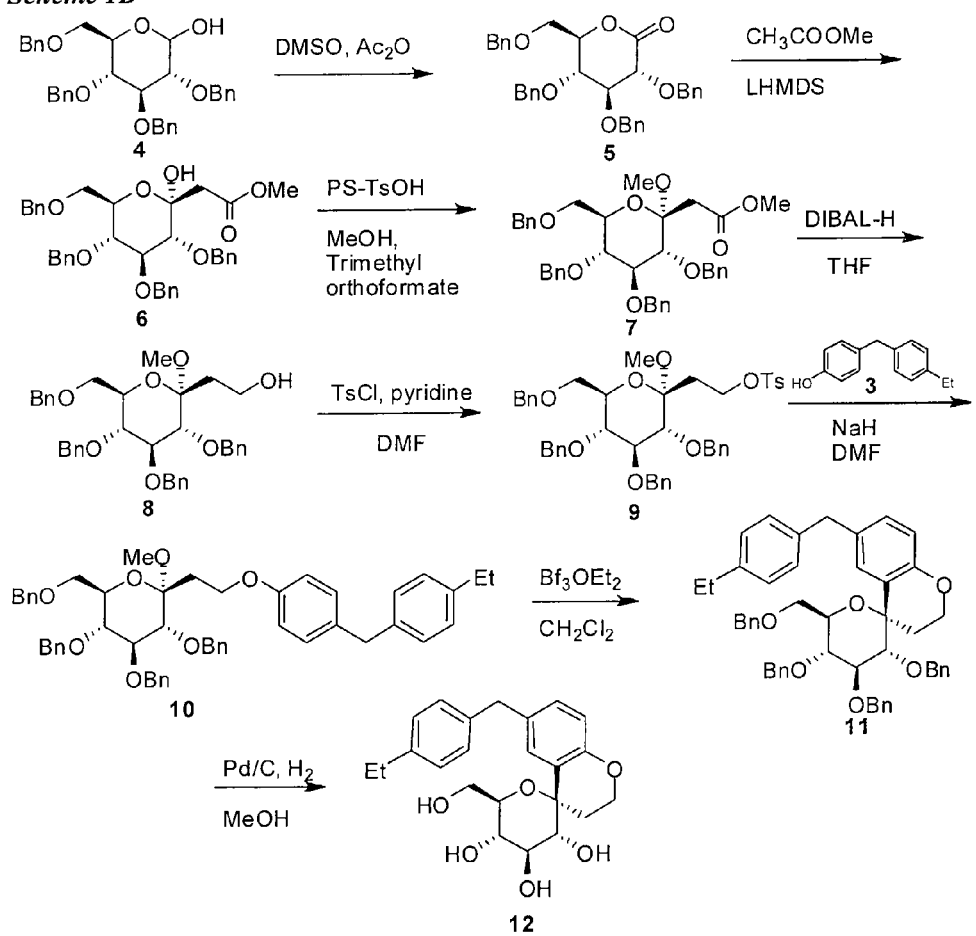

Part A: Synthesis of 4-(4-ethylbenzyl)phenol (3). The overall synthetic scheme for phenol 3 is depicted in Scheme 1A (see FIG. 11).

Synthesis of (4-ethylphenyl)(4-methoxyphenyl)methanone (1)

To a solution of 4-ethylbenzoyl chloride (8.6 g, 51.0 mmol) in anhydrous DCM (200 mL) at −5 to 0° C., was added anisole (5.46 g, 50.5 mmol), followed by addition of aluminum chloride (7.0 g, 52.5 mmol) over 5 minutes. The resulting yellow reaction mixture was stirred at 0° C. for 1 h and then at rt for 2 h. The reaction mixture was poured into ice water (300 mL), extracted with DCM (300 mL×2). Combined DCM solution was washed with 1M aqueous HCl (300 mL×1), 2 N aqueous NaOH (200 ml×1), brine (400 mL×2), dried over $MgSO_4$ and evaporated to give the product, 12.2 g, yield 100%. $^1$H NMR (300 MHz, $CDCl_3$) δ 7.80 (d, J=8.7 Hz, 2H), 7.68 (d, J=8.1 Hz, 2H), 7.27 (d, J=8.1 Hz, 2H), 6.93 (d, J=8.7 Hz, 2H), 3.87 (s, 3H), 2.71 (q, J=7.5 Hz, 2H), 1.28 (t, J=7.5 Hz, 3H). ESI-MS m/z 240.9 (M+H)$^+$.

Synthesis of 1-ethyl-4-(4-methoxybenzyl)benzene (2)

To a solution of (4-ethylphenyl)(4-methoxyphenyl)methanone (1) (6.0 g, 25 mmol) in acetonitrile (50 mL) and DCM (50 mL) at 0° C., was added triethylsilane (6.7 g, 57.5 mmol), followed by addition of boron trifluoride etherate (5.3 g, 37.5 mmol). The reaction mixture was stirred at 0° C. for 2 h, then at 50° C. for 3 h. After cooling to rt, the reaction mixture was diluted with DCM (500 mL) and washed with 2N aqueous NaOH (200 mL×2), brine (200 mL×3), dried over $MgSO_4$ and evaporated to give product as a colorless oil, 5.3 g, yield 93.7% $^1$H NMR (300 MHz, $CDCl_3$) δ 7.06-7.09 (m, 6H), 6.79 (d, J=8.7 Hz, 2H), 3.87 (s, 2H), 3.76 (s, 3H), 2.60 (q, J=7.5 Hz, 2H), 1.21 (t, J=7.5 Hz, 3H).

Synthesis of 4-(4-ethylbenzyl)phenol (3)

To a solution of 1-ethyl-4-(4-methoxybenzyl)benzene (2) (1.39 g, 5.74 mmol) in dry DCM (15 mL) at −40° C. under nitrogen, was added boron tribromide (0.6 mL, 1.56 g, 6.23 mmol). The resulting reaction mixture was stirred at 40° C. to rt over 2 h, then poured into ice water (50 mL), extracted with DCM (50 mL×3). The combined DCM solution was washed with water (50 mL×2), brine (50 ml×1), dried over $MgSO_4$ and evaporated to afford an oil product which crystallized on standing, 1.34 g, yield 100%. $^1$H NMR (300 MHz, $CDCl_3$) δ 7.07 (m, 4H), 7.03 (d, J=8.7 Hz, 2H), 6.72 (d, J=8.7 Hz, 2H), 3.86 (s, 2H), 2.60 (q, J=7.5 Hz, 2H), 1.21 (t, J=7.5 Hz, 3H).

Part B: Synthesis of (2'S,3'R,4'S,5'S,6'R)-6-(4-ethylbenzyl)-6'-(hydroxymethyl)-3',4',5',6'-tetrahydrospiro[chroman-4,2'-pyran]-3',4',5'-triol (12). The overall synthetic scheme for compound 12 is depicted in Scheme 1B (see FIG. 11).

Synthesis of (3R,4S,5R,6R)-3,4,5-tris(benzyloxy)-6-(benzyloxymethyl)tetrahydro-2H-pyran-2-one (5)

(3R,4S,5R,6R)-3,4,5-Tris(benzyloxy)-6-(benzyloxymethyl)tetrahydro-2H-pyran-2-ol (4) (2.00 g, 3.7 mmol, Senn Chemicals) was dissolved in solution of 12.0 mL DMSO and 8.0 mL $Ac_2O$. After stirring for 12 h, the reaction was diluted with EtOAc, washed with $H_2O$ (1×), sat. $NaHCO_3$ (1×), then dried ($Na_2SO_4$) and concentrated using high-vacuum to provide a syrup (1.89 g, 95%). LC/MS 100% (ELSD) $t_R$=3.10 min, calcd for $C_{34}H_{34}O_6$: 538.24, found 539.4 (M+H)$^+$.

Synthesis of methyl 2-((2S,3R,4S,5R,6R)-3,4,5-tris(benzyloxy)-6-(benzyloxymethyl)-2-hydroxytetrahydro-2H-pyran-2-yl)acetate (6)

Methyl acetate (0.25 mL, 3.2 mmol) was dissolved in THF (3 mL) under an atmosphere of Ar and cooled to −78° C. (acetone/dry ice). A solution of LHMDS (3.13 mL, 1M/THF) was added dropwise. After 15 minutes, a solution of (3R,4S,5R,6R)-3,4,5-tris(benzyloxy)-6-(benzyloxymethyl)tetrahydro-2H-pyran-2-one (5, 1.35 g, 2.5 mmol) in THF (7 mL) was added dropwise. After 3 hr, the reaction mixture was quenched with $NH_4Cl$ (aq), warmed to room temperature and extracted with EtOAc (1×). The organic layer was washed with brine (1×), dried ($Na_2SO_4$), and concentrated to a syrup (1.4 g, 92%). $^1$H NMR (300 MHz, $CDCl_3$) δ ppm: 7.15-7.31 (m, 20H), 2.26 (d, J=1.5 Hz, 1H), 4.81-4.97 (m, 4H), 4.45-4.66 (m, 4H), 3.98 (m, 1H), 3.58-3.75 (m, 7H), 3.31 (dd, J=9.6, 1.5 Hz, 1H), 2.73 (d, J=15.6 Hz, 1H), 2.30 (d, J=15.6 Hz, 1H). LC/MS $t_R$=3.16 min, calcd for $C_{37}H_{40}O_8$: 612.27, found 635.6 (M+Na)$^+$.

Synthesis of methyl 2-((2S,3R,4S,5R,6R)-3,4,5-tris(benzyloxy)-6-(benzyloxymethyl)-2-methoxytetrahydro-2H-pyran-2-yl)acetate (7)

Methyl 2-((2S,3R,4S,5R,6R)-3,4,5-tris(benzyloxy)-6-(benzyloxymethyl)-2-hydroxytetrahydro-2H-pyran-2-yl)acetate (6) (1.4 g, 2.28 mmol) was dissolved in a solution of MeOH (6 mL) and trimethyl orthoformate (4 mL). PL-$SO_3H$ resin (Polymer Laboratories, 0.25 g, 3.75 mmol/g loading) was added and the reaction mixture was heated to 60° C. for 4.75 h. The mixture was filtered through cotton, rinsing with MeOH and $CH_2Cl_2$, then concentrated to a syrup (1.4 g, 99%). LC/MS $t_R$=3.27 min, calcd for $C_{38}H_{42}O_8$: 626.29, found 649.6 (M+Na)$^+$.

Synthesis of 2-((2S,3R,4S,5R,6R)-3,4,5-tris(benzyloxy)-6-(benzyloxymethyl)-2-methoxytetrahydro-2H-pyran-2-yl)ethanol (8)

Methyl 2-((2S,3R,4S,5R,6R)-3,4,5-tris(benzyloxy)-6-(benzyloxymethyl)-2-methoxytetrahydro-2H-pyran-2-yl)acetate (7) (0.48 g, 0.77 mmol) was dissolved in THF (8 mL)

under an atmosphere of Ar and cooled to 0° C. DIBAL-H (2 mL of a 20% solution in toluene) was added dropwise. The reaction mixture was stirred at room temperature for 0.75 h, then cooled again to 0° C. and stirred with Rochelle's salt for 2 hours. The mixture was extracted with $Et_2O$ (3×). The organic layers were combined, washed with $H_2O$ (1×), dried ($Na_2SO_4$) and concentrated to a syrup (0.46 g, 100%). LC/MS 98.5% (ELSD) $t_R$=3.10 min, calcd for $C_{37}H_{42}O_7$: 598.29, found 621.3 $(M+Na)^+$.

Synthesis of 2-((2S,3R,4S,5R,6R)-3,4,5-tris(benzyloxy)-6-(benzyloxymethyl)-2-methoxytetrahydro-2H-pyran-2-yl)ethyl 4-methylbenzenesulfonate (9)

2-((2S,3R,4S,5R,6R)-3,4,5-Tris(benzyloxy)-6-(benzyloxymethyl)-2-methoxytetrahydro-2H-pyran-2-yl)ethanol (8) (0.46 g, 0.77 mmol) was dissolved in $CH_2Cl_2$ (2 mL). Pyridine (0.31 mL, 3.85 mmol) and TsCl (0.29 g, 1.54 mmol) were added and the reaction mixture was heated at 50° C. for 18 h. Additional TsCl (0.05 g, 0.26 mmol) was then added and the reaction mixture was heated at 50° C. for another 4 hours. The mixture was concentrated onto celite and chromatographed over $SiO_2$, (ISCO system, 0-40% EtOAc/hexanes) to provide an oil (0.317 g, 55%). $^1$H NMR (300 MHz, $CDCl_3$) δ ppm: 7.66 (d, J=8.4 Hz, 2H), 7.14-7.32 (m, 22H), 4.77-4.89 (m, 4H), 4.46-4.57 (m, 4H), 3.86-4.07 (m, 1H), 3.48-3.64 (m, 4H), 3.31 (d, J=9.3 Hz, 1H), 3.17 (s, 3H), 2.36 (s, 3H), 2.13 (t, J=8.1 Hz, 1H). LC/MS $t_R$=3.37 min, calcd for $C_{44}H_{48}O_9S$: 752.3, found 775.2 $(M+Na)^+$.

Synthesis of (2S,3R,4S,5R,6R)-3,4,5-tris(benzyloxy)-6-(benzyloxymethyl)-2-(2-(4-(4-ethylbenzyl)phenoxy)ethyl)-2-methoxytetrahydro-2H-pyran (10)

4-(4-Ethylbenzyl)phenol (3) (28 mg, 0.13 mmol) was dissolved in DMF (200 μL). NaH (5 mg, 60%/mineral oil, 0.13 mmol) was added. After 5 min, a solution of 2-((2S,3R,4S,5R,6R)-3,4,5-tris(benzyloxy)-6-(benzyloxymethyl)-2-methoxytetrahydro-2H-pyran-2-yl)ethyl 4-methylbenzenesulfonate (9) (50 mg in 200 μL DMF) was added to the phenoxide solution. After 2 h, the reaction was heated to 60° C. for 2 h, then stirred overnight at room temperature (15h). The reaction mixture was diluted with EtOAc and washed with $NaHCO_3$ (2×). The aqueous layers were combined and back-extracted with EtOAc (2×). The organic layers were combined, dried, and concentrated provide 72 mg. $^1$HNMR indicated that the product was present, but with extraneous phenol contamination. The sample was purified by preparative thin-layer chromatography ($SiO_2$, eluting with 40% EtOAc/hexanes) to provide a film (26.1 mg, approx 50%) that still had contaminating phenol present. The material was carried forward to the next step. $^1$H NMR (300 MHz, $CDCl_3$) δ ppm: 6.99-7.32 (m, 25H), 6.69 (m, 3H), 4.48-4.97 (m, 8H), 4.13 (t, J=9 Hz, 1H), 3.94 (m, 1H), 3.86 (s, 2H), 3.55-3.80 (m, 6H), 3.26 (s, 3H), 2.60 (q, J=15.3, 7.8 Hz, 2H), 2.27 (m, 2H), 1.21 (t, J=8.1 Hz). LC/MS $t_R$=6.47 min, calcd for $C_{52}H_{56}O_7$: 792.4, found 815.4 $(M+Na)^+$.

Synthesis of (2'S,3'R,4'S,5'R,6'R)-3',4',5'-tris(benzyloxy)-6'-(benzyloxymethyl)-6-(4-ethylbenzyl)-3',4',5',6'-tetrahydrospiro[chroman-4,2'-pyran] (11)

(2S,3R,4S,5R,6R)-3,4,5-Tris(benzyloxy)-6-(benzyloxymethyl)-2-(2-(4-(4-ethylbenzyl)phenoxy)ethyl)-2-methoxytetrahydro-2H-pyran (10) (26 mg, 0.033 mmol) was dissolved in $CH_2Cl_2$ and cooled to −78° C. $BF_3$—$OEt_2$ (approx 2 drops) was added and the reaction mixture was removed from the ice bath. After 30 minutes, the reaction mixture was diluted with $CH_2Cl_2$, washed with water, dried ($Na_2SO_4$) and concentrated. The crude mixture was purified by preparative thin-layer chromatography ($SiO_2$, 40% EtOAc/hexanes) using a TLC plate that had been pre-rinsed (pre-development with the same eluent), providing a film (13.4 mg, 54%). $^1$H NMR (300 MHz, $CDCl_3$) δ ppm: 7.07-7.36 (m, 20H), 7.00 (m, 4H), 6.86 (m, 2H), 6.77 (d, J=8.4 Hz, 1H), 4.31-4.88 (m, 8H), 4.32 (m, 2H), 4.08 (m, 1H), 3.65-3.92 (m, 7H), 2.44-2.61 (m, 3H), 2.16 (m, 1H), 1.14 (t, 7.8 Hz, 3H). LC/MS: No final LC/MS was performed as initial LC/MS attempts could not identify any product peaks, most likely because of prolonged retention times of the compound.

Synthesis of (2'S,3'R,4'S,5'S,6'R)-6-(4-ethylbenzyl)-6'-(hydroxymethyl)-3',4',5',6'-tetrahydrospiro[chroman-4,2'-pyran]-3',4',5'-triol (12)

(2'S,3'R,4'S,5'R,6'R)-3',4',5'-Tris(benzyloxy)-6'-(benzyloxymethyl)-6-(4-ethylbenzyl)-3',4',5',6'-tetrahydrospiro[chroman-4,2'-pyran] (11) (13.4 mg (0.018 mmol) was dissolved in MeOH (1 mL). Pd/C (5 mg, 10% Pd/C) was added, the reaction vessel was flushed with $H_2$, (3×, alternating with high vacuum), then stirred under an atmosphere of $H_2$. After 3 h, additional Pd/C (5 mg) was added and the vessel flushed again with $H_2$ (3×, alternating with high vacuum), and the reaction mixture was stirred for an additional 16 h. The crude mixture was concentrated onto celite and chromatographed over $SiO_2$ (ISCO system, 0-20% MeOH/$CH_2Cl_2$) to provide two fractions, with 1.7 and 6.3 mg respectively. (8 mg total, >100%). The smaller fraction was of the highest purity and was submitted for biological analysis. (The second fraction had slightly dark color, indicating some Pd contamination.) For the pure fraction: $^1$H NMR (300 MHz, $CDCl_3$) δ ppm: 7.22 (m, 2H), 6.99-7.11 (m, 5H), 6.77 (d, J=8.1 Hz, 1H), 4.27-4.33 (m, 1H), 4.04-4.11 (m, 1H), 3.59-3.97 (m, 6H), 2.60 (q, J=15, 7.5 Hz, 2H), 2.37-2.46 (m, 1H), 2.12 (m, 1H), 1.21 (t, J=7.5 Hz, 3H). LC/MS 98.4% (ELSD) $t_R$=1.80 min, calcd for $C_{23}H_{28}O_6$: 400.19, found 423.0 $(M+Na)^+$.

Example 2

Synthesis of (2'S,3'R,4'S,5'S,6'R)-7-chloro-6-(4-ethylbenzyl)-6'-(hydroxymethyl)-3',4',5',6'-tetrahydrospiro[chroman-4,2'-pyran]-3',4',5'-triol (Compound 20)

Figure 12:
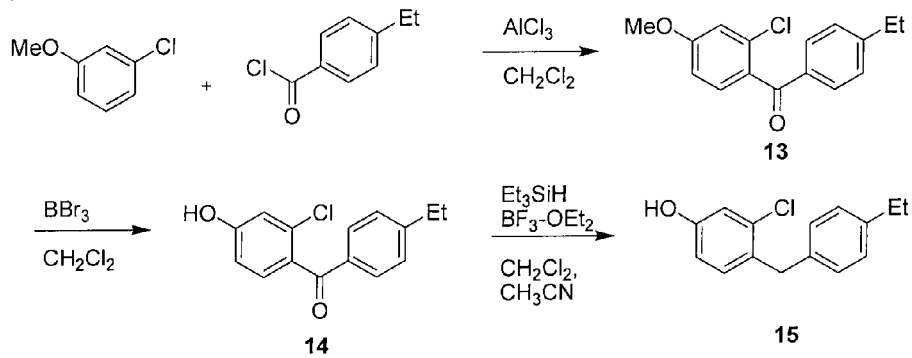
Figure 12:
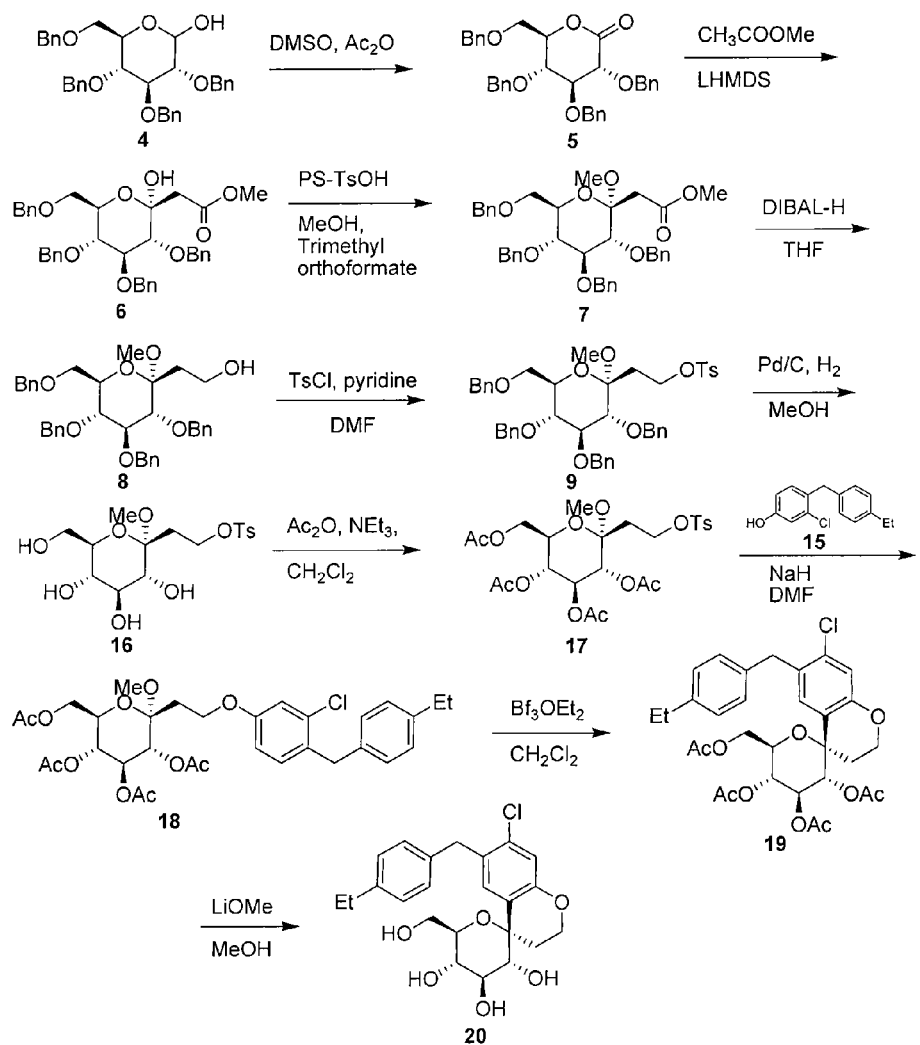

Part A: Synthesis of 3-chloro-4-(4-ethylbenzyl)phenol (15). The overall synthetic scheme for phenol 15 is depicted in Scheme 2A (see FIG. 12).

3-Chloroanisole (2.62 mL, 21 mmol) was dissolved in $CH_2Cl_2$ (20 mL) along with 4-ethylbenzoylchloride (3 mL, 20 mmol) and cooled to 0° C. Then aluminumtrichloride (2.72 g, 20 mmol) was added slowly. The reaction is stirred and let warm to room temperature and stirring continued for 2 h. Saturated sodium bicarbonate solution is added slowly with ethylacetate until no more gas evolution is observed. The organic layer is then dried with sodium sulfate and evaporated. The crude reaction products are then subjected to silica gel chromatography (hexanes/ethylacetate) to give a mixture of products. The second major peak eluted containing 13 was taken into the next step as a mixture of compounds. Approximately 300 mg of this material was taken into ~5 mL $CH_2Cl_2$ and ~150 μL of $BBr_3$ is added and stirred at rt until all of the starting material was consumed (TLC analysis). Water is then added and the organic layer is dried with sodium sulfate and evaporated to give crude product 14. This crude material is then taken into 3 mL of CH$_2$Cl$_2$ and 2 mL of acetonitrile are added, followed by triethylsilane (400 µL) and BF$_3$OEt$_2$ (200 µL). The reaction is stirred at 40° C. for 12 h, then evaporated and ethylacetate and water are added. The organic layer is dried with sodium sulfate, evaporated, and then preparative TLC purification of this crude material gives the title compound 15. $^1$H NMR (300 MHz, CDCl$_3$) δ ppm: 7.08 (q, J=8.4 Hz, 4H), 6.98 (d, J=8.1 Hz, 1H), 6.85 (d, J=2.7, 1H), 6.73 (dd, J=8.1, 2.7 Hz, 1H), 3.97 (s, 2H), 2.60 (q, J=7.5 Hz, 2H), 1.21 (t, J=7.5 Hz, 3H); $^{13}$C NMR (CDCl$_3$) δ ppm: 154.21, 141.91, 136.97, 134.37, 131.51, 131.05, 128.60, 127.81, 116.30, 114.02, 37.93, 28.49, 15.68; LC/MS: (ELSD) t$_R$=3.17 min, calcd for C$_{15}$H$_{15}$ClO: 246.1, found 245.2 (M–H)$^-$.

Part B: Synthesis of (2'S,3'R,4'S,5'S,6'R)-7-chloro-6-(4-ethylbenzyl)-6'-(hydroxymethyl)-3',4',5',6'-tetrahydrospiro[chroman-4,2'-pyran]-3',4',5'-triol (20). The overall synthetic scheme for compound 20 is depicted in Scheme 2B (see FIG. 12).

Synthesis of 2-((2S,3R,4S,5S,6R)-3,4,5-trihydroxy-6-(hydroxymethyl)-2-methoxytetrahydro-2H-pyran-2-yl)ethyl 4-methylbenzenesulfonate (16)

2-((2S,3R,4S,5R,6R)-3,4,5-Tris(benzyloxy)-6-(benzyloxymethyl)-2-methoxytetrahydro-2H-pyran-2-yl)ethyl 4-methylbenzenesulfonate (9) (0.32 g, 0.42 mmol) was dissolved in MeOH (3 mL). Pd/C (60 mg, 10% Pd/C) was added and the reaction flask was flushed with H$_2$ (3×), and then allowed to stir under a balloon of H$_2$. After 15 h, the reaction was filtered through a celite plug, rinsing with MeOH and CH$_2$Cl$_2$ and concentrated to provide an oil (165 mg, 100%). LC/MS: t$_R$=1.36 min, calcd for C$_{16}$H$_{24}$O$_9$S: 392.11, found 415.2 (M+Na)$^+$.

Synthesis of (2S,3R,4S,5R,6R)-6-(acetoxymethyl)-2-methoxy-2-(2-(tosyloxy)ethyl)tetrahydro-2H-pyran-3,4,5-triyl triacetate (17)

2-((2S,3R,4S,5S,6R)-3,4,5-Trihydroxy-6-(hydroxymethyl)-2-methoxytetrahydro-2H-pyran-2-yl)ethyl 4-methylbenzenesulfonate (16) (39 mg, 0.1 mmol) was dissolved in CH$_2$Cl$_2$ (0.5 mL). Ac$_2$O (56 µL, 0.6 mmol) and NEt$_3$ (84 µL, 0.6 mmol) were added. After 2 h, additional Ac$_2$O (40 mL, 0.4 mmol) and NEt$_3$ (40 mL, 0.28 mmol) were added. After 16 h, the reaction mixture was diluted with CH$_2$Cl$_2$, washed with sat. NaHCO$_3$ (1×), brine (1×), then dried (Na$_2$SO$_4$) and concentrated an oil (55 mg, 100%). $^1$H NMR (300 MHz, CDCl$_3$) δ ppm: 7.79 (d, J=8.1 Hz, 2H), 7.36 (d, J=8.7 Hz, 2H), 5.41 (t, J=9.6 Hz, 1H), 4.94 (t, J=9.9 Hz, 1H), 4.87 (d, J=9.6 Hz, 1H), 4.03-4.17 (m, 5H), 3.80 (dq, J=10.5, 5, 3 Hz, 1H), 3.25 (s, 3H), 3.04 (q, J=15, 6.9 Hz, 2H), 2.22 (s, 3H), 2.07 (s, 3H), 2.05 (s, 3H), 2.01 (s, 3H), 1.96 (s, 3H), 1.28 (t, J=7.2 Hz, 3H). LC/MS: 89% (ELSD) t$_R$=2.30 min, calcd for C$_{24}$H$_{32}$O$_{13}$S: 560.1, found 582.9 (M+Na)$^+$.

Synthesis of (2S,3R,4S,5R,6R)-6-(acetoxymethyl)-2-(2-(3-chloro-4-(4-ethylbenzyl)phenoxy)ethyl)-2-methoxytetrahydro-2H-pyran-3,4,5-triyl triacetate (18)

3-Chloro-4-(4-ethylbenzyl)phenol (15) (55 mg, 0.22 mmol) was dissolved in DMF (0.30 mL) and NaH (9 mg, 0.22 mmol) was added to the solution. After stirring for 5 min, a solution of (2S,3R,4S,5R,6R)-6-(acetoxymethyl)-2-methoxy-2-(2-(tosyloxy)ethyl)tetrahydro-2H-pyran-3,4,5-triyl triacetate (17) (102 mg, 0.18 mmol in 200 µL DMF) was added to the phenoxide solution. After 2 h, the reaction was heated to 70° C. and stirred for 18 h. The reaction mixture was then diluted with EtOAc and washed with NaHCO$_3$ (1×). The aqueous layer was back-extracted with EtOAc (2×). The organic layers were combined, dried (Na$_2$SO$_4$), concentrated onto celite and chromatographed over SiO$_2$ (ISCO system, 0-60% EtOAc/hexanes) to provide an oil (19 mg, 17%). $^1$H NMR (300 MHz, CDCl$_3$) δ ppm: 7.07 (m, 5H), 6.88 (d, J=2.4 Hz, 1H), 6.69 (dd, J=8.9, 2.6 Hz, 1H), 5.47 (t, J=9.6 Hz, 1H), 5.00-5.15 (m, 3H), 3.85-4.17 9 m, 6H), 3.32 (s, 3H), 2.61 (q, J=15, 7.5 Hz, 2H), 2.06 (s, 3H), 2.05 (s, 3H), 2.03 (s, 3H), 1.98 (s, 3H), 1.21 (t, J=7.5 Hz, 3H). LC/MS: t$_R$=3.07 min, calcd for C$_{32}$H$_{39}$ClO$_{11}$: 634.22, found 657.4 (M+Na)$^+$.

Synthesis of (2'S,3'R,4'S,5'R,6'R)-6'-(acetoxymethyl)-7-chloro-6-(4-ethylbenzyl)-3',4',5',6'-tetrahydrospiro[chroman-4,2'-pyran]-3',4',5'-triyl triacetate (19)

(2S,3R,4S,5R,6R)-6-(Acetoxymethyl)-2-(2-(3-chloro-4-(4-ethylbenzyl)phenoxy)ethyl)-2-methoxytetrahydro-2H-pyran-3,4,5-triyl triacetate (18) (19 mg, 0.03 mmol) was azeotropically dried (3×) with toluene, then dissolved in CH$_2$Cl$_2$ (0.4 mL), cooled to 0° C., and treated with BF$_3$—OEt$_2$ (approx 8 drops of a 48% solution). After 24 h, the reaction was concentrated onto celite and chromatographed over SiO$_2$ (ISCO system, 0-40% EtOAc/hexanes) to provide a film (9.6 mg, 53%). $^1$H NMR (300 MHz, CDCl$_3$) δ ppm: 7.35 (s, 1H), 7.09 (s, 4H), 6.83 (s, 1H), 5.63 (d, J=9.9 Hz, 1H), 5.40 (t, J=9.6 Hz, 1H), 5.18 (t, J=10.2 Hz, 1H), 4.26-4.33 (m, 1H), 4.05-4.20 (m, 4H), 3.95 (s, 2H), 3.93 (m, 2H), 2.60 (q, J=15, 7.5 Hz, 2H), 2.04 (s, 3H), 2.04 (s, 3H), 2.01 (s, 3H), 1.83 (s, 3H), 1.21 (t, J=7.8 Hz, 3H). LC/MS 99.7% (ELSD) t$_R$=2.93 min, calcd for C$_{31}$H$_{35}$ClO$_{10}$: 602.19, found 620.4 (M+H$_2$O)$^+$.

Synthesis of (2'S,3'R,4'S,5'S,6'R)-7-chloro-6-(4-ethylbenzyl)-6'-(hydroxymethyl)-3',4',5',6'-tetrahydrospiro[chroman-4,2'-pyran]-3',4',5'-triol (20)

(2'S,3'R,4'S,5'R,6'R)-6'-(Acetoxymethyl)-7-chloro-6-(4-ethylbenzyl)-3',4',5',6'-tetrahydrospiro[chroman-4,2'-pyran]-3',4',5'-triyl triacetate (19) (9.6 mg, 0.02 mmol) was dissolved in MeOH (0.2 mL) and treated with LiOMe (20 µL of a 1M solution in MeOH). After 24 h, the reaction mixture was filtered through a syringe filter and concentrated, then passed through a small SiO$_2$ column, eluting with 5% MeOH/CH$_2$Cl$_2$ to provide a film (5.8 mg, 83%). $^1$H NMR (300 MHz, CD$_3$OD) δ ppm: 7.37 (s, 1H), 7.05 (s, 4H), 6.79 (s, 1H), 4.33 (m, 1H), 4.13 (m, 1H), 3.97 (s, 2H), 3.78 (m, 2H), 3.48-3.62 (m, 3H), 3.33 (m, 2H), 2.57 (q, J=15, 7.8 Hz, 2H), 2.33-2.42 (m, 1H), 2.13-2.21 (m, 1H), 1.19 (t, J=7.5 Hz, 3H). LC/MS 100% (ELSD) t$_R$=1.99 min, calcd for C$_{23}$H$_{27}$ClO$_6$: 434.15, found 434.15 (M+Na)$^+$.

Example 3

Synthesis of (2'R,3'R,4'S,5'S,6'R)-6-chloro-5-(4-ethylbenzyl)-6'-(hydroxymethyl)-3',4',5',6'-tetrahydro-2H-spiro[benzofuran-3,2'-pyran]-3',4',5'-triol (Compound 30)

Figure 13:
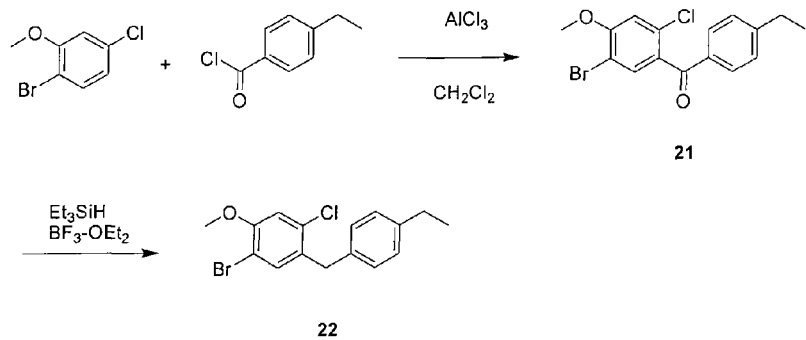
Figure 13:
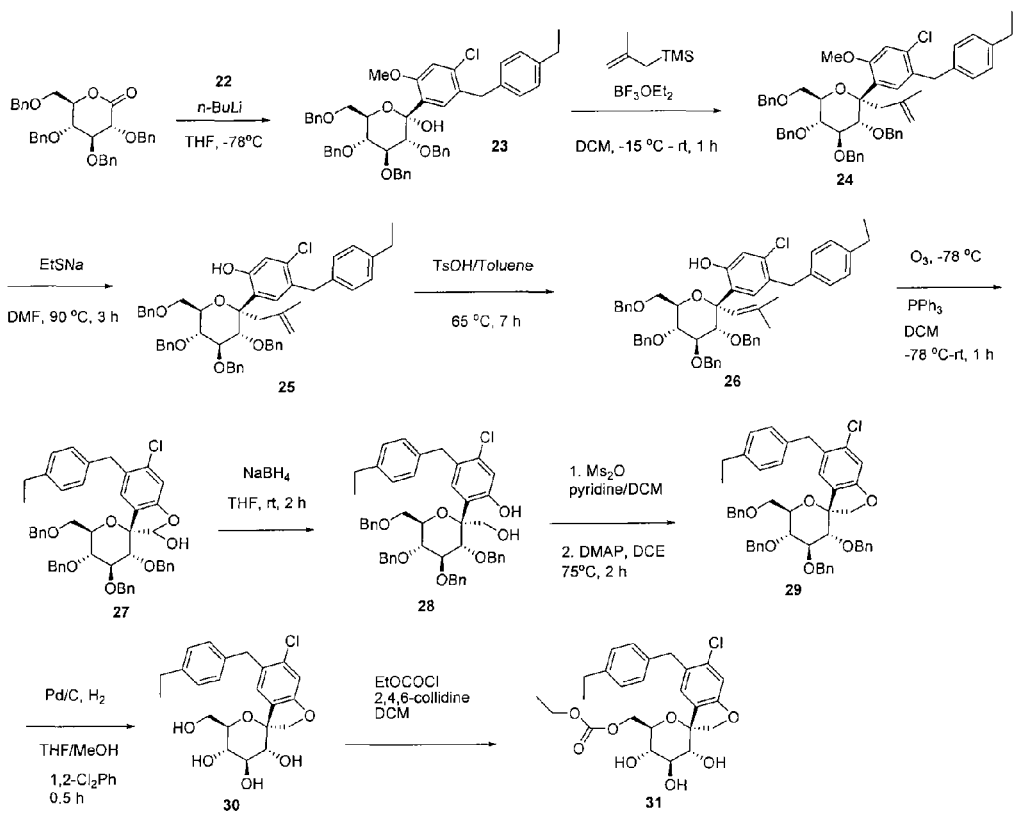

Part A: Synthesis of 1-bromo-4-chloro-5-(4-ethylbenzyl)-2-methoxybenzene (22). The overall synthetic scheme for 22 is depicted in Scheme 3A (see FIG. 13).

Synthesis of (5-bromo-2-chloro-4-methoxyphenyl) (4-ethylphenyl)methanone (21)

To a solution of 1-bromo-4-chloro-2-methoxybenzene (5.1 g, 23 mmol) and 4-ethylbenzoyl chloride (4.1 g, 24 mmol) in 15 mL of anhydrous dichloromethane (DCM) was added aluminum trichloride (3.2 g, 24 mmol). The mixture was stirred at room temperature for 1 hour, followed by heating at reflux for 18 hours. The mixture was poured into 100 mL of ice-cold water and the organic layer was isolated. The aqueous solution was extracted with 25 mL DCM. The combined organic extracts were washed with brine (25 mL), dried ($Na_2SO_4$), filtered, and evaporated. Recrystallization from petroleum ether gave the intermediate (5-bromo-2-chloro-4-methoxyphenyl)(4-ethylphenyl)methanone 21 (5.6 g, 69%).

Synthesis of 1-bromo-4-chloro-5-(4-ethylbenzyl)-2-methoxybenzene (22)

(5-bromo-2-chloro-4-methoxyphenyl)(4-ethylphenyl) methanone (21) (5.6 g, 69%) was dissolved in trifluoroacetic acid (40 mL). To this mixture was added triethylsilane (6.3 mL, 40 mmol) and methanesulfonic acid (0.40 mL, 6.0 mmol). The resulting solution was stirred at room temperature for 2.5 hours, after which it was partitioned between water and ethyl acetate. The organic layer was washed with water (1×25 mL), followed by saturated $NaHCO_3$ (2×25 mL) and brine (25 mL). The organic layer was dried ($Na_2SO_4$), filtered, and evaporated. Silica gel chromatography with 0-10% ethyl acetate in hexane gave the title compound (4.7 g, 88%) as a white solid. $^1$H NMR (300 MHz, $CDCl_3$) δ 7.29 (s, 1H), 7.09-7.04 (m, 4H), 6.88 (s, 1H), 3.95 (s, 2H), 3.84 (s, 3H), 2.61 (q, J=7.5 Hz, 2H), 1.21 (t, J=7.5 Hz, 3H).

Part B: Synthesis of (2'R,3'R,4'S,5'S,6'R)-6-chloro-5-(4-ethylbenzyl)-6'-(hydroxymethyl)-3',4',5',6'-tetrahydro-2H-spiro[benzofuran-3,2'-pyran]-3',4',5'-triol (Compound 30). The overall synthetic scheme for compound 30 is depicted in Scheme 3B (see FIG. 13).

Synthesis of (2S,3R,4S,5R,6R)-3,4,5-tris(benzyloxy)-6-(benzyloxymethyl)-2-(4-chloro-5-(4-ethylbenzyl)-2-methoxyphenyl)tetrahydro-2H-pyran-2-ol (23)

To a solution of (3R,4S,5R,6R)-3,4,5-tris(benzyloxy)-6-(benzyloxymethyl)tetrahydro-2H-pyran-2-one 5 (1.10 g, 2.04 mmol) and 1-bromo-4-chloro-5-(4-ethylbenzyl)-2-methoxybenzene 22 (0.60 g, 1.77 mmol) in anhydrous THF (20 mL) at −78° C. was added a solution of n-BuLi (0.78 mL, 1.94 mmol, 2.5 M). The mixture was stirred for 1 h, warmed to ambient temperature, quenched with 10% sodium carbonate (100 mL), and extracted with ethyl acetate (2×50 mL). The organic phase was dried with anhydrous $MgSO_4$, filtered, and evaporated to dryness. The residue was purified by silica gel column chromatography using 15-25% ethyl acetate in petroleum ether to give 23 (0.91 g, 64%). LC/MS m/z 822 (M+Na), 782 (M−OH).

Synthesis of (2S,3R,4S,5R,6R)-3,4,5-tris(benzyloxy)-6-(benzyloxymethyl)-2-(4-chloro-5-(4-ethylbenzyl)-2-methoxyphenyl)-2-(2-methylallyl)tetrahydro-2H-pyran (24)

To a mixture of methallyltrimethylsilane (185 μL, 1.05 mmol) and 23 (0.28 g, 0.35 mmol) in anhydrous methylene chloride (10 mL) at −20° C. was added $BF_3 \cdot OEt_2$ (88 μL, 0.70 mmol) in a drop-wise manner. The resulting light orange mixture was stirred for 1 hour, during which the temperature was allowed to rise to 0° C. The reaction mixture was quenched with 10% $NaHCO_3$ and extracted with DCM. The organic layer was separated, dried ($Na_2SO_4$), filtered, and evaporated to yield a residue which was purified by column chromatography eluting with 0-15% EtOAc in petroleum ether to give 24 (153 mg, 52%). $^1$H NMR (300 MHz, $CDCl_3$) δ 7.18-7.30 (m, 20H), 7.00-7.05 (m, 1H), 6.98 (s, 4H), 6.69 (s, 1H), 4.67 (t, J=10.8 Hz, 1H), 4.49-4.60 (m, 8H), 4.24 (d, J=11.4 Hz, 1H), 4.12 (d, J=6.0 Hz, 1H), 3.67-4.00 (m, 7H), 3.54 (s, 3H), 3.07 (d, J=16.2 Hz, 1H), 2.79 (d, J=15.9 Hz, 1H), 2.55 (q, J=7.5 Hz, 2H), 1.54 (s, 3H), 1.17 (t, J=7.5 Hz, 3H). LC/MS m/z 860 (M+Na).

Synthesis of 5-chloro-4-(4-ethylbenzyl)-2-((2S,3R,4S,5R,6R)-3,4,5-tris(benzyloxy)-6-(benzyloxymethyl)-2-(2-methylallyl)tetrahydro-2H-pyran-2-yl) phenol (25)

A mixture of sodium ethanethiolate (151 mg, 1.79 mmol) and 24 (150 mg, 0.179 mmol) in DMF (3 mL) was flushed with argon and heated at 90° C. for 3 h. The reaction mixture was cooled to 0° C. A mixture of acetic acid and water (1:1, 2 mL) was added. The resulting mixture was stirred for 10 min and then concentrated to dryness. The residue was partitioned between water and dichloromethane. The organic layer was separated, dried ($Na_2SO_4$), and evaporated. The residue was purified by preparatory TLC eluting with 10% EtOAc in petroleum ether to give 25 (135 mg, 92%). LC/MS m/z 846 (M+Na).

Synthesis of 5-chloro-4-(4-ethylbenzyl)-2-((2S,3R,4S,5R,6R)-3,4,5-tris(benzyloxy)-6-(benzyloxymethyl)-2-(2-methylprop-1-enyl)tetrahydro-2H-pyran-2-yl)phenol (26)

A mixture of p-toluenesulfonic acid (0.136 mg, 0.789 mmol) and 25 (0.65 g, 0.789 mmol) was heated at 65° C. for 7 hours. The reaction mixture was cooled to ambient temperature, after which it was partitioned between 10% $NaHCO_3$ and EtOAc. The organic layer was dried ($Na_2SO_4$), filtered, and evaporated. The residue was purified by silica gel column chromatography eluting with 5% EtOAc in petroleum ether to give 26 (490 mg, 75%). $^1$H NMR (300 MHz, $CDCl_3$) δ 8.83 (s, 1H), 7.20-7.34 (m, 18H), 7.03-7.10 (m, 2H), 6.92-7.00 (m, 7H), 6.85 (s, 1H), 5.59 (s, 1H), 4.77-4.89 (m, 3H), 4.63 (d, J=12.0 Hz, 1H), 4.36-4.44 (m, 3H), 4.00 (d, J=15.6 Hz, 1H), 3.95 (dd, J=5.1, 10.2 Hz, 1H), 3.65-3.80 (m, 6H), 3.52 (dd, J=2.1, 10.5 Hz, 1H), 2.56 (q, J=7.8 Hz, 2H), 1.70 (s, 3H), 1.42 (s, 3H), 1.19 (t, J=7.5 Hz, 3H). LC/MS m/z 846 (M+Na).

Synthesis of (2R,2'S,3'R,4'S,5'R,6'R)-3',4',5'-tris (benzyloxy)-6'-(benzyloxymethyl)-6-chloro-5-(4-ethylbenzyl)-3',4',5',6'-tetrahydro-2H-spiro[benzofuran-3,2'-pyran]-2-ol (27)

Ozonized oxygen was bubbled for 10 minutes into anhydrous dichloromethane (100 mL) at −78° C. A solution of 26 (300 mg, 0.364 mmol) in dichloromethane (2 mL) and MeOH (4 mL) was added with stirring at −78° C. with continued flow of ozone. Two minutes after addition of 26, the ozone bubbler was removed. After stirring the resulting mixture for five minutes at −78° C., triphenylphosphine (287 mg, 1.09 mmol) was added. The reaction mixture was allowed to warm up to ambient temperature and stirred for 1 hour, after which it was evaporated in vacuo. The residue was purified by preparatory TLC eluting with 15% EtOAc in petroleum ether to give 27 (128 mg, 44% yield). A portion of the starting material 26 (63 mg) was also recovered. LC/MS m/z 780 (M–OH).

Synthesis of 5-chloro-4-(4-ethylbenzyl)-2-((2R,3R,4S,5R,6R)-3,4,5-tris(benzyloxy)-6-(benzyloxymethyl)-2-(hydroxymethyl)tetrahydro-2H-pyran-2-yl)phenol (28)

To a solution of 27 (100 mg, 0.125 mmol) in anhydrous THF (2 mL) under an argon blanket was added sodium borohydride (23.7 mg, 0.627 mmol). The resulting mixture was stirred for 2 hours, after which it was quenched with MeOH (1 mL) and AcOH (0.5 mL), followed by partitioning between water and EtOAc. The organic phase was dried over $Na_2SO_4$, filtered, and evaporated. The residue was loaded onto a preparatory TLC plate and eluted with 15% EtOAc in petroleum ether to give 28 (92 mg, 92% yield). $^1$H NMR (300 MHz, $CDCl_3$) δ 8.64 (s, 1H), 7.15-7.35 (m, 16H), 7.07-7.14 (m, 3H), 6.91-6.99 (m, 7H), 4.78-4.82 (m, 3H), 4.62 (d, J=12.0 Hz, 1H), 4.31-4.48 (m, 4H), 4.15 (dd, J=4.2, 13.2 Hz, 1H), 3.81-4.03 (m, 7H), 3.74 (d, J=10.2 Hz, 1H), 3.63 (dd, J=2.3, 10.2 Hz, 1H), 2.53 (q, J=7.5 Hz), 1.66 (t, broad, J=5.4 Hz, 1H, OH?), 1.16 (t, J=7.5 Hz, 3H). LC/MS m/z 822 (M+Na).

Synthesis of (2'R,3'R,4'S,5'R,6'R)-3',4',5'-tris(benzyloxy)-6'-(benzyloxymethyl)-6-chloro-5-(4-ethylbenzyl)-3',4',5',6'-tetrahydro-2H-spiro[benzofuran-3,2'-pyran] (29)

To a solution of 28 (92 mg, 0.115 mmol), pyridine (90 μL) and DMAP (8 mg) in DCM was added methanesulfonic anhydride (36 mg, 0.207 mmol, 1.8 equiv). The resulting mixture was stirred for 1 hour. LC/MS analysis indicated complete conversion of 28 to its mono-mesic ester. The mixture was partitioned between 10% sodium bicarbonate and DCM. The organic phase was dried over anhydrous sodium sulfate, filtered, and evaporated to a crude residue. The residue was heated in DCE (1.5 mL) containing DMAP (40 mg) at 75° C. for 2 h. The mixture was cooled to ambient temperature, directly loaded onto a preparatory TLC plate, and eluted with 15% ethyl acetate in petroleum ether to give 29 (66 mg, 73% yield). $^1$H NMR (300 MHz, $CDCl_3$) δ 7.12-7.30 (m, 19H), 7.06 (s, 1H), 6.98 (s, 4H), 6.89 (s, 1H), 6.81-6.84 (m, 2H), 4.74-4.90 (m, 4H), 4.42-4.60 (m, 5H), 3.90-4.06 (m, 5H), 3.44-3.80 (m, 6H), 2.54 (q, J=7.5 Hz, 2H), 1.16 (t, J=7.5 Hz, 3H). LCMS m/z 804 (M+Na).

Synthesis of (2'R,3'R,4'S,5'S,6'R)-6-chloro-5-(4-ethylbenzyl)-6'-(hydroxymethyl)-3',4',5',6'-tetrahydro-2H-spiro[benzofuran-3,2'-pyran]-3',4',5'-triol (30)

To a solution of 29 (60 mg, 0.77 mmol) in a mixture of MeOH (2.4 mL) and THF (0.8 mL) were added $Pd(OH)_2$/C (25 mg) and 1,2-dichlorobenzene (60 μL). A balloon of hydrogen gas was attached for 0.5 hours with vigorous stirring. LC/MS indicated that de-protection was complete. The reaction mixture was filtered through Celite, concentrated to a residue, and purified by preparatory TLC (5% MeOH in DCM) to give 30 (23 mg, 71.2%). $^1$H NMR (300 MHz, $CD_3OD$) δ 7.18 (s, 1H), 7.07 (s, 4H), 6.82 (s, 1H), 4.68 (d, J=10.2 Hz, 1H), 4.59 (d, J=9.9 Hz, 1H), 3.99 (m, 2H), 3.59-3.80 (m, 3H), 3.28-3.37 (m, 3H), 2.58 (q, J=7.5 Hz, 2H), 1.19 (t, J=7.5 Hz, 3H).

Synthesis of ((2'R,3'R,4'S,5'S,6'R)-6-chloro-5-(4-ethylbenzyl)-3',4',5'-trihydroxy-3',4',5',6'-tetrahydro-2H-spiro[benzofuran-3,2'-pyran]-6'-yl)methyl ethyl carbonate (31)

To a solution of 30 (12 mg, 28.5 μmol) in 2,4,6-collidine (100 μL) at −30° C. was added a solution of ethyl chloroformate (4 μL, 41.8 umol, 1.5 eq.) in DCM (100 μL). The mixture was kept at −30° C. for 1.5 hours, warmed to ambient temperature, and stirred overnight, after which additional ethylchloroformate (4 μL) was added. The reaction mixture was quenched with methanol, evaporated, and purified via HPLC to give 31 (7.5 mg, 53% yield). $^1$H NMR (300 MHz, $CD_3OD$) δ 7.14 (s, 1H), 7.07 (s, 4H), 6.83 (s, 1H), 4.68 (d, J=10.2 Hz, 1H), 4.57 (d, J=10.5 Hz, 1H), 4.36 (dd, J=2.1, 11.4 Hz, 1H), 4.21 (dd, J=5.1, 11.4 Hz, 1H), 4.08 (q, J=7.2 Hz, 2H), 3.99 (s, 2H), 3.71 (d, J=9.6 Hz, 1H), 3.53-3.59 (m, 1H), 3.39 (t, J=8.7 Hz, 1H), 3.27-3.34 (m, 1H), 2.58 (q, J=7.5 Hz, 2H), 1.17-1.23 (m, 6H).

Synthesis of ((3'R,4'S,5'S,6'R)-7-chloro-6-(4-ethylbenzyl)-3',4',5'-trihydroxy-3',4',5',6'-tetrahydrospiro[chroman-4,2'-pyran]-6'-yl)methyl ethyl carbonate (32)

Following a similar procedure to that used for making 31, compound 32 (9.0 mg, 51% yield) was prepared from 20 (15 mg, 34.5 μmol). $^1$H NMR (300 MHz, $CD_3OD$) δ 7.31 (s, 1H), 7.05 (s, 4H), 6.80 (s, 1H), 4.30-4.39 (m, 2H), 4.19 (dd, J=5.7, 11.4 Hz), 4.03-4.12 (m, 3H), 3.97 (s, 2H), 3.77 (d, J=9.3 Hz, 1H), 3.66-3.72 (m, 1H), 3.59 (t, J=9.6 Hz, 1H), 3.39 (t, J=9.9 Hz, 1H), 2.57 (q, J=7.5 Hz, 2H), 2.33-2.43 (m, 1H), 2.10-2.18 (m, 1H), 1.16-1.22 (m, 6H). LC/MS m/z 507 (M+H).

Example 4

Figure 14:
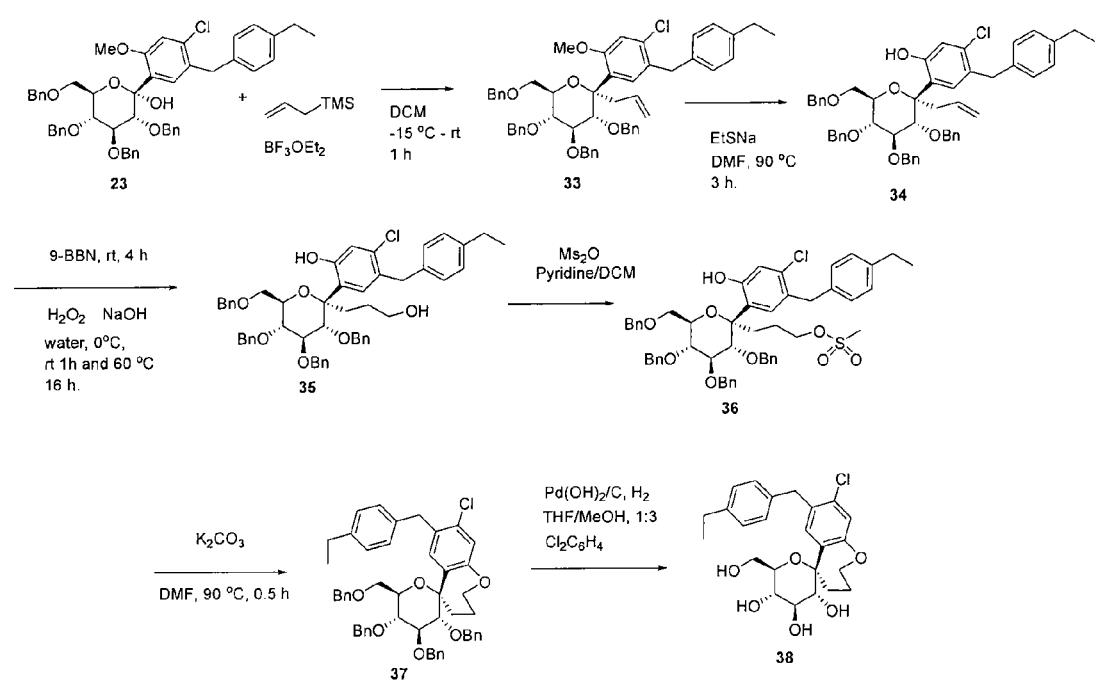

Synthesis of (2'S,3'R,4'S,5'S,6'R)-8-chloro-7-(4-ethylbenzyl)-6'-(hydroxymethyl)-3,3',4,4',5',6'-hexahydro-2H-spiro[benzo[b]oxepine-5,2'-pyran]-3',4',5'-triol (Compound 38). The overall synthetic scheme for compound 38 is depicted in Scheme 4 (see FIG. 14).

Synthesis of (2S,3R,4S,5R,6R)-2-allyl-3,4,5-tris(benzyloxy)-6-(benzyloxymethyl)-2-(4-chloro-5-(4-ethylbenzyl)-2-methoxyphenyl)tetrahydro-2H-pyran (33)

The title compound (230 mg, 80%) was prepared from 23 (280 mg) and allyltrimethylsilane (167 μL, 120 mg, 3.0 eq.) using the method described for preparing 24.
$^1$H NMR (300 MHz, $CDCl_3$) δ 7.50 (s, 1H), 7.07-7.31 (m, 20H, inaccurate due to the solvent), 7.00 (s, 4H), 6.75 (s, 1H), 5.56-5.70 (m, 1H), 4.90-5.00 (m, 2H), 4.78 (d, J=10.8 Hz, 1H), 4.48-4.66 (m, 6H), 4.03-4.11 (m, 2H), 3.68-3.97 (m, 7H), 3.56 (s, 3H), 3.27 (dd, J=6.6, 15.9 Hz, 1H), 2.86 (dd, J=6.6, 15.9 Hz, 1H), 2.56 (q, J=7.5 Hz, 2H), 1.18 (t, J=7.5 Hz, 3H).

Synthesis of 2-((2S,3R,4S,5R,6R)-2-allyl-3,4,5-tris(benzyloxy)-6-(benzyloxymethyl)tetrahydro-2H-pyran-2-yl)-5-chloro-4-(4-ethylbenzyl)phenol (34)

34 (500 mg, 98% yield) was prepared from 33 (520 mg) using the same procedure used to prepare 25. $^1$H NMR (300 MHz, $CDCl_3$) δ 8.95 (s, 1H), 7.20-7.39 (m, 18H), 6.87-7.14 (m, 10H), 5.48-5.62 (m, 1H), 4.75-4.99 (m, 5H), 4.65 (d, J=12 Hz, 1H), 4.38-4.49 (m, 3H), 3.69-4.02 (m, 9H), 3.52-3.58 (m, 1H), 3.03 (dd, J=6.3, 16.2 Hz, 1H), 2.75 (dd, J=6.3, 16.2 Hz, 1H), 2.55 (q, J=7.5 Hz, 2H), 1.17 (t, J=7.5 Hz, 3H). LC/MS m/z 827 (M+H+water), 832 (M+Na).

Synthesis of 5-chloro-4-(4-ethylbenzyl)-2-((2S,3R, 4S,5R,6R)-3,4,5-tris(benzyloxy)-6-(benzyloxymethyl)-2-(3-hydroxypropyl)tetrahydro-2H-pyran-2-yl)phenol (35)

To a stirred solution of 34 (200 mg, 0.247 mmol) in dry THF (4 mL) was added 9-BBN in THF (2.0 mL, 0.5 M, 4.1 equiv). The resulting mixture was stirred at ambient temperature for 4 hours and then cooled 0° C. Water (2.5 mL), 1 M aqueous NaOH (0.8 mL) and 30% $H_2O_2$ (0.25 mL) were added at 0° C. The mixture was stirred for 1 hour at ambient temperature and 16 hours at 60° C. in a sealed vial. After cooling, the mixture was partitioned between water and EtOAc. The organic layer was dried ($MgSO_4$), filtered and evaporated. The residue was purified using preparatory TLC eluting with 18% EtOAc in petroleum ether to give 35 (200 mg, 99% yield). LCMS m/z 828 (M+H), 850 (M+Na).

Synthesis of (2'S,3'R,4'S,5'R,6'R)-3',4',5'-tris(benzyloxy)-6'-(benzyloxymethyl)-8-chloro-7-(4-ethylbenzyl)-3,3',4,4',5',6'-hexahydro-2H-spiro[benzo[b]oxepine-5,2'-pyran] (37)

To a solution of 35 (115 mg, 0.139 mmol) and pyridine (100 μL) in DCM (1 mL) was added methanesulfonic anhydride (44 mg, 0.25 mmol, 1.8 equiv). The resulting mixture was stirred at ambient temperature for 1 hour. LC/MS analysis indicated complete conversion of 35 to mono mesic ester 36. The reaction mixture was partitioned between 10% sodium bicarbonate and DCM, after which the organic phase was dried over anhydrous sodium sulfate, filtered, and evaporated to obtain a residue which was heated in DMF (3 mL) containing potassium carbonate (100 mg) at 90° C. for 0.5 hours. The resulting mixture was extracted with DCM, after which the organic layer was separated, dried ($Na_2SO_4$), filtered, and evaporated. Preparatory TLC of the residue eluting with 12% ethyl acetate in petroleum ether gave 37 (62 mg, 55% yield). $^1$H NMR (300 MHz, $CDCl_3$) δ 7.54 (s, 1H), 7.16-7.28 (m, 21H), 7.08-7.11 (m, 2H), 6.98 (m, 4H), 6.97 (s, 1H), 4.81 (d, J=11.1 Hz, 1H), 4.77 (d, J=10.8 Hz, 1H), 4.73 (d, J=10.8 Hz, 1H), 4.47-4.60 (m, 3H), 4.35 (d, J=10.5 Hz, 1H), 4.16-4.24 (m, 1H), 3.70-4.02 (m, 11H), 2.60-2.71 (m, 1H), 2.54 (q, J=7.5 Hz, 2H), 2.02-2.13 (m, 1H), 1.81-1.93 (m, 2H), 1.16 (t, J=7.5 Hz, 3H). LC/MS m/z 832 (M+Na), 810 (M+H).

Synthesis of (2'S,3'R,4'S,5'S,6'R)-8-chloro-7-(4-ethylbenzyl)-6'-(hydroxymethyl)-3,3',4,4',5',6'-hexahydro-2H-spiro[benzo[b]oxepine-5,2'-pyran]-3',4',5'-triol (38)

Compound 38 (19 mg, 62% yield) was prepared from 37 (55 mg, 67.9 μmol) using the procedure described for synthesizing 30. $^1$H NMR (300 MHz, $CD_3OD$) δ 7.53 (s, 1H), 7.06 (s, 4H), 6.93 (s, 1H), 4.06-4.15 (m, 1H), 3.93-4.01 (m, 3H), 3.82 (dd, J=11.7, 0.9 Hz, 1H), 3.49-3.62 (m, 4H), 3.22-3.33 (m, 2H), 2.56 (q, J=7.5 Hz), 2.14-2.36 (m, 2H), 1.96-2.13 (m, 1H), 1.75-1.84 (m, 1H), 1.19 (t, J=7.5 Hz, 3H). LC/MS m/z 449 (M+H).

Example 5

Figure 15:
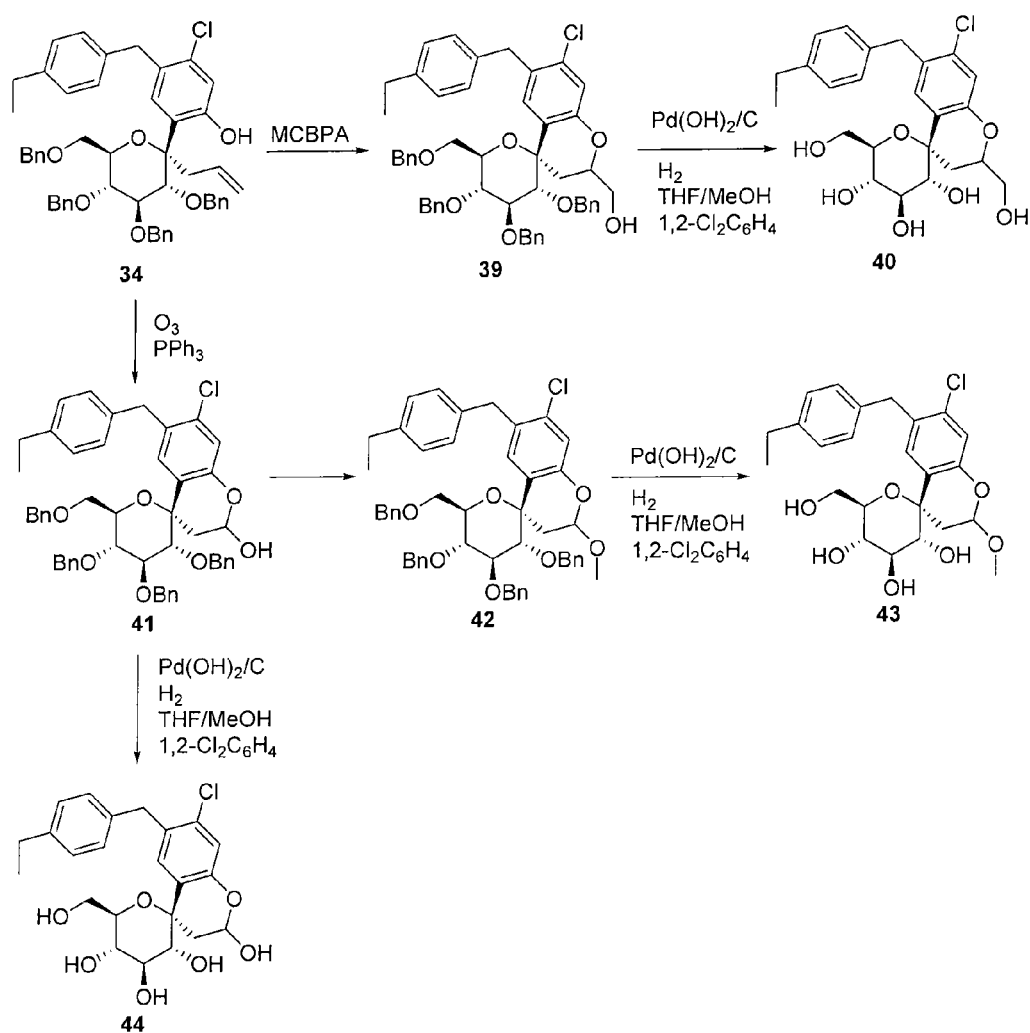

This example illustrates the preparation of compounds 40, 43 and 44 as provided in Scheme 5 (see FIG. 15).

Preparation of ((2'S,3'R,4'S,5'R,6'R)-3',4',5'-tris(benzyloxy)-6'-(benzyloxymethyl)-7-chloro-6-(4-ethylbenzyl)-3',4',5',6'-tetrahydrospiro[chroman-4,2'-pyran]-2-yl)methanol (39)

To a solution of 34 (70 mg, 86 μmol) in anhydrous DCM (1 mL) was added 3-chlorobenzoperoxoic acid (23 mg, 104 μmol, 1.2 equiv). The reaction was stirred overnight, directly loaded onto a preparatory TLC plate, and eluted with 15% EtOAc in petroleum ether to give 39 (17 mg, 24% yield), a single diastereomer. $^1$H NMR (300 MHz, $CDCl_3$) δ 7.14-7.32 (m, 18H), 6.98 (d, J=8.1 Hz, 2H), 6.96 (s, 1H), 6.90 (d, J=8.1 Hz, 2H), 6.79-6.83 (m, 2H), 4.85 (d, J=10.8 Hz, 1H), 4.80 (s, 2H), 4.58 (d, J=10.8 Hz, 1H), 4.57 (d, J=12.0 Hz, 1H), 4.45 (d, J=12.0 Hz, 1H), 4.37 (d, J=10.8 Hz, 1H), 4.07-4.15 (m, 1H), 4.05 (d, J=15.6 Hz, 1H), 3.61-3.91 (m, 10H), 2.49 (q, J=7.5 Hz), 2.08-2.35 (m, 3H), 1.12 (t, J=7.5 Hz, 3H). LCMS m/z 826 (M+H), 848 (M+Na).

Preparation of (2'S,3'R,4'S,5'S,6'R)-7-chloro-6-(4-ethylbenzyl)-2,6'-bis(hydroxymethyl)-3',4',5',6'-tetrahydrospiro[chroman-4,2'-pyran]-3',4',5'-triol (40)

To a solution of 39 (17 mg, 21 μmol) in a mixture of MeOH (1.5 mL) and THF (0.5 mL) were added $Pd(OH)_2$/C (15 mg) and 1,2-dichlorobenzene (30 μL). A balloon of hydrogen gas was attached for 0.5 h with vigorous stirring. LC/MS indicated that de-protection was complete. The reaction mixture was filtered through Celite, concentrated to a residue, and purified by preparatory TLC (5% MeOH in DCM) to give 40 (6.2 mg, 64%). $^1$H NMR (300 MHz, $CD_3OD$) δ 7.37 (s, 1H), 7.06 (s, 4H), 6.88 (s, 1H), 4.16-4.34 (m, 1H), 3.98 (AB pattern, J=12.0 Hz, 2H), 3.88 (d, (d, J=9.6 Hz, 1H), 3.74-3.80 (m, 3H), 3.51-3.61 (m, 3H), 3.30-3.35 (m, 1H, under the solvent), 2.57 (q, J=7.5 Hz, 2H), 2.28 (d, J=13.5 Hz, 1H), 2.11 (dd, J=12.3, 15.0 Hz, 1H), 1.19 (t, J=7.5 Hz, 3H). LC/MS m/z 465 (M+H), 487 (M+Na).

Preparation of (2'S,3'R,4'S,5'R,6'R)-3',4',5'-tris(benzyloxy)-6'-(benzyloxymethyl)-7-chloro-6-(4-ethylbenzyl)-3',4',5',6'-tetrahydrospiro[chroman-4,2'-pyran]-2-ol (41)

Using the same procedure for making 27, compound 41 (150 mg, 75% yield) was prepared as a mixture of two diastereomers from 34 (200 mg, 247 μmol). LC/MS m/z 833 (M+Na).

Preparation of (2'S,3'R,4'S,5'R,6'R)-3',4',5'-tris(benzyloxy)-6'-(benzyloxymethyl)-7-chloro-6-(4-ethylbenzyl)-2-methoxy-3',4',5',6'-tetrahydrospiro[chroman-4,2'-pyran] (42)

To a solution of 41 (85 mg, 105 μmol) in anhydrous MeOH (1 mL) and trimethylorthoformate (0.5 mL) was added 4-toluenesulfonic acid (15 mg). The mixture was heated in a closed vial at 65° C. for 2 h, cooled to rt, evaporated, loaded onto a preparatory TLC plate, and developed using 15% EtOAc in petroleum ether to yield 42 (75 mg, 91% yield) as two diastereomers. LCMS m/z 847 (M+Na).

Preparation of (2'S,3'R,4'S,5'S,6'R)-7-chloro-6-(4-ethylbenzyl)-6'-(hydroxymethyl)-2-methoxy-3',4',5',6'-tetrahydrospiro[chroman-4,2'-pyran]-3',4',5'-triol (43)

Using the same procedure used to prepare 30, compound 43 (18 mg, 80% yield) was prepared as 2:1 mixture of diastereomers from 42 (40 mg, 48.5 umol). LC/MS m/z 487 (M+Na), 447 (M−OH), 433 (M−OMe).

Preparation of (2'S,3'R,4'S,5'S,6'R)-7-chloro-6-(4-ethylbenzyl)-6'-(hydroxymethyl)-3',4',5',6'-tetrahydrospiro[chroman-4,2'-pyran]-2,3',4',5'-tetraol (44)

To a solution of 41 (20 mg, 25 μmol) in a mixture of MeOH (1.5 mL) and THF (0.5 mL) was added $Pd(OH)_2$ on carbon (15 mg). A balloon of hydrogen gas was attached for 0.5 h with vigorous stirring. LC/MS indicated that de-protection was complete. The reaction mixture was filtered through Celite, concentrated to a residue, and purified by preparatory HPLC to give 44 (10 mg, 90%) as a mixture of two diastereomers. LCMS m/z 433 (M−OH).

Example 6

Figure 16:
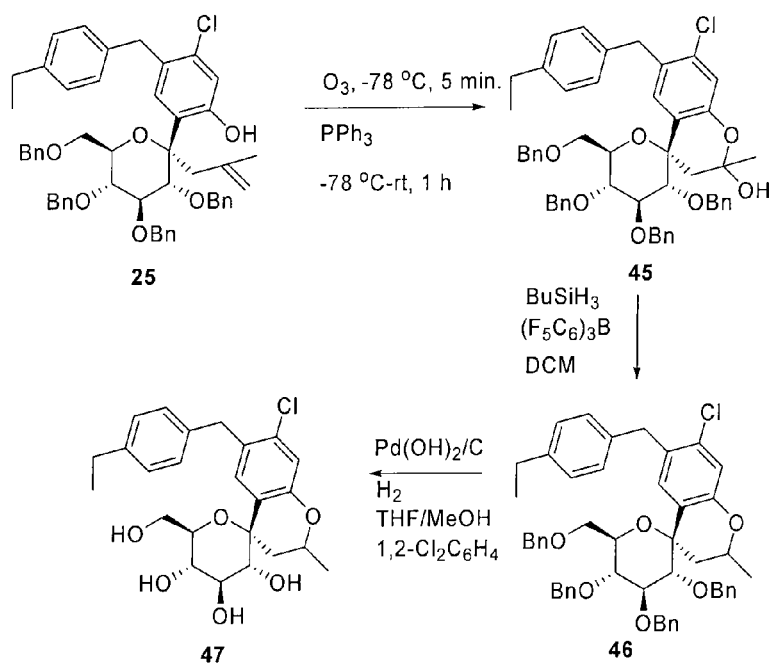
Figure 16:
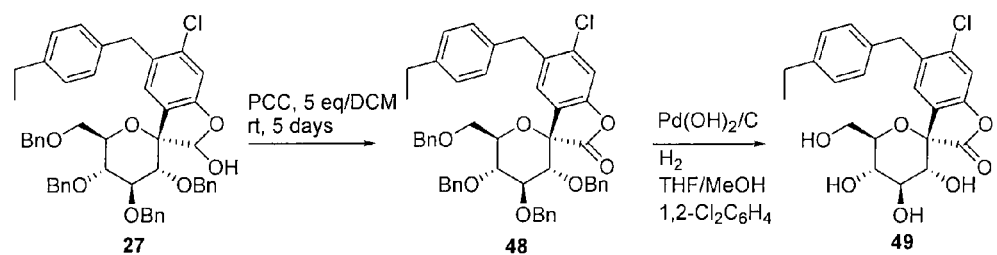

This example illustrates the preparation of compound 47 according to Scheme 6 (see FIG. 16).

Preparation of (2'S,3'R,4'S,5'R,6'R)-3',4',5'-tris(benzyloxy)-6'-(benzyloxymethyl)-7-chloro-6-(4-ethylbenzyl)-2-methyl-3',4',5',6'-tetrahydrospiro[chroman-4,2'-pyran]-2-ol (45)

Using the same procedure for making 27, compound 45 (75 mg, 95% yield) was made as two diastereomers from 25 (79 mg, 96 umol). LC/MS m/z 848 (M+Na), 808 (M−OH).

Preparation of (2'S,3'R,4'S,5'R,6'R)-3',4',5'-tris(benzyloxy)-6'-(benzyloxymethyl)-7-chloro-6-(4-ethylbenzyl)-2-methyl-3',4',5',6'-tetrahydrospiro[chroman-4,2'-pyran] (46)

To a solution of 45 (38 mg, 46 μmol) in dry DCM (1 mL) flushed with argon was added tris(pentafluorophenyl)borane (5 mg, 9.6 μmol). After stirring for 10 min, n-butylsilane (8 μL, ~2 equiv) was added. Stirring was continued for 3 days. The mixture was directly loaded onto a preparatory TLC plate, developed with 15% EtOAc in petroleum ether to give 46 (21 mg, 56% yield) as a single diastereomer. $^1$H NMR (300 MHz, CDCl$_3$) δ 7.14-7.31 (m, 19H), 6.81-6.99 (m, 6H), 4.86 (d, J=10.5 Hz, 1H), 4.81 (s, 2H), 4.58 (d, J=12.0 Hz, 2H), 4.45 (d, J=12.0 Hz, 1H), 4.33 (d, J=10.8 Hz, 1H), 4.07-4.16 (m, 2H), 4.04 (d, J=15.0 Hz, 1H), 3.61-3.89 (m, 8H), 2.49 (q, J=7.5 Hz, 2H), 2.15-2.20 (m, 2H), 1.41 (d, J=6.0 Hz), 1.11 (t, J=7.5 Hz, 3H).LCMS m/z 832 (M+Na), 810 (M+H).

Preparation of (2'S,3'R,4'S,5'S,6'R)-7-chloro-6-(4-ethylbenzyl)-6'-(hydroxymethyl)-2-methyl-3',4',5',6'-tetrahydrospiro[chroman-4,2'-pyran]-3',4',5'-triol (47)

Using the same procedure for making 30, compound 47 (6.5 mg, 56% yield) was made from 46 (21 mg, 26 μmol). For 47, $^1$H NMR (300 MHz, CD$_3$OD) δ 7.36 (s, 1H), 7.05 (s, 4H), 6.81 (s, 1H), 4.14-4.25 (m, 1H), 3.97 (AB pattern, J=15.3 Hz, 2H), 3.74-3.86 (m, 2H), 3.50-3.62 (m, 3H), 3.26-3.33 (m, 1H), 2.55 (q, J=7.5 Hz, 2H), 2.25 (dd, J=1.5, 14.7 Hz, 1H), 1.99 (dd, J=12.3, 15 Hz, 1H), 1.40 (d, J=6.0 Hz, 3H), 1.19 (t, J=7.5 Hz, 3H).

Example 7

This example illustrates the preparation of compound 49 according to the method outlined in Scheme 7 (see FIG. 16).

Preparation of (2'S,3'R,4'S,5'R,6'R)-3',4',5'-tris(benzyloxy)-6'-(benzyloxymethyl)-6-chloro-5-(4-ethylbenzyl)-3',4',5',6'-tetrahydro-2H-spiro[benzofuran-3,2'-pyran]-2-one (48)

To a solution of 27 (8 mg, 10 μmol) in DCM was added pyridinium chlorochromate (9 mg, 42 μmol, 4.2 equiv). The mixture was stirred for 5 days until the reaction was complete. The mixture was directly loaded onto a preparatory TLC plate and developed using 15% EtOAc in petroleum ether to give 48 (5 mg, 62% yield). $^1$H NMR (300 MHz, CDCl$_3$) δ 7.00-7.40 (m, 25H), 6.76 (d, J=6.6 Hz, 2H), 4.80-4.92 (m, 3H), 4.64 (d, J=10.8 Hz, 1H), 4.38-4.57 (m, 5H), 3.92-4.03 (m, 3H), 3.71-3.82 (m, 3H), 3.60 (dd, J=1.8, 11.1 Hz, 1H), 2.57 (q, J=7.5 Hz, 2H), 1.18 (t, J=7.5 Hz, 3H).

Preparation of (2'S,3'R,4'S,5'S,6'R)-6-chloro-5-(4-ethylbenzyl)-3',4',5'-trihydroxy-6'-(hydroxymethyl)-3',4',5',6'-tetrahydro-2H-spiro[benzofuran-3,2'-pyran]-2-one (49)

To a solution of 48 (5 mg, 6.3 μmol) in a mixture of MeOH (1.5 mL) and THF (0.5 mL) were added Pd(OH)$_2$/C (10 mg) and 1,2-dichlorobenzene (12 μL). A balloon of hydrogen gas was attached for 0.5 h with vigorous stirring. LCMS indicated that de-protection was complete. The reaction mixture was filtered through Celite, concentrated to a residue, and purified by passing through silica gel in a pipette (5% MeOH in DCM) to give 49 (2.2 mg, 80%). $^1$H NMR (300 MHz, CD$_3$OD) δ 7.35 (s, 1H), 7.20 (s, 1H), 7.09 (s, 4H), 4.24-4.29 (m, 1H), 4.07 (t, J=10.5 Hz, 1H), 4.06 (s, 2H), 3.81 (dd, J=2.1, 12.0 Hz, 1H), 3.61-3.71 (m, 2H), 3.43 (t, J=9.9 Hz, 1H), 2.59 (q, J=7.5 Hz, 2H), 1.20 (t, J=7.5 Hz, 3H).

Example 8

Figure 17:
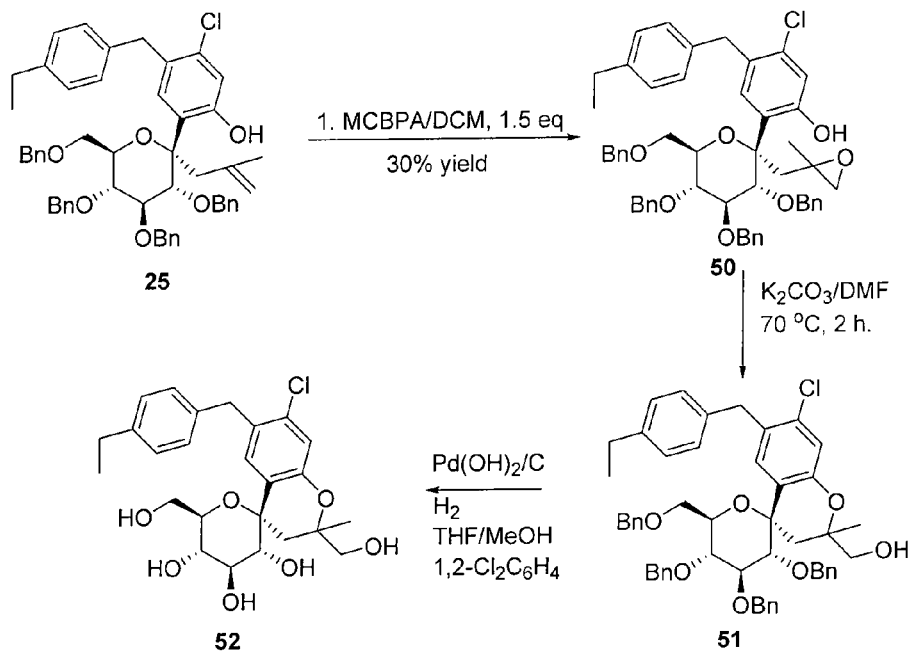
Figure 17:
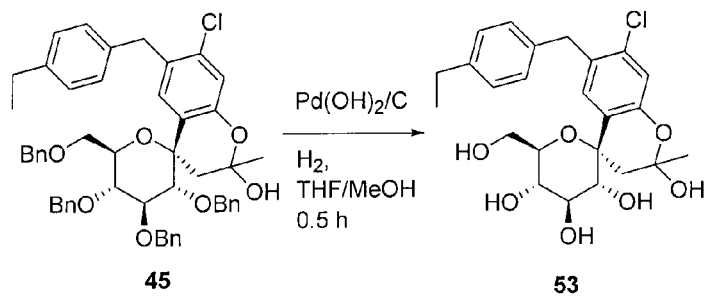

This example illustrates the preparation of 52 according to the method outlined in Scheme 8 (see FIG. 17).

Preparation of 5-chloro-4-(4-ethylbenzyl)-2-((2R,3R,4S,5R,6R)-3,4,5-tris(benzyloxy)-6-(benzyloxymethyl)-2-((2-methyloxiran-2-yl)methyl)tetrahydro-2H-pyran-2-yl)phenol (50)

To a solution of 25 (52 mg, 63 μmol) in anhydrous DCM (1 mL) was added 3-chlorobenzoperoxoic acid (21 mg, 95 μmol, 1.2 equiv). The reaction was stirred overnight, directly loaded onto a preparatory TLC plate, and eluted with 15% EtOAc in petroleum ether to give 50 (41 mg, 77% yield). LC/MS m/z 862 (M+Na).

Preparation of ((2'S,3'R,4'S,5'R,6'R)-3',4',5'-tris(benzyloxy)-6'-(benzyloxymethyl)-7-chloro-6-(4-ethylbenzyl)-2-methyl-3',4',5',6'-tetrahydrospiro[chroman-4,2'-pyran]-2-yl)methanol (51)

A mixture of 50 (19 mg, 22.6 μmol) and potassium carbonate (30 mg, 226 μmol) in DMF (2 mL) was heated to 70° C. for 2 h in a closed vial. LCMS indicated a complete conversion to a less polar product. The mixture was evaporated, and the residue was separated between water and DCM. The organic phase was dried (Na$_2$SO$_4$), filtered, and evaporated. The residue was purified by preparatory TLC, developed with 15% EtOAc in petroleum ether to give 51 (13 mg, 68% yield). $^1$H NMR (300 MHz, CDCl$_3$) δ 7.09-7.31 (m, 19H), 6.93-7.01 (m, 4H), 6.90 (s, 1H), 6.80-6.84 (m, 2H), 4.73-4.86 (m, 3H), 4.29-4.55 (m, 3H), 4.28 (d, J=10.8 Hz, 1H), 4.09 (d, J=15.0 Hz, 1H), 4.02 (d, J=8.7 Hz, 1H), 3.69-3.93 (m, 7H), 3.17-3.38 (m, 3H), 2.49-2.59 (m, 3H), 2.20 (d, J=15.6 Hz, 1H), 1.46 (s, 3H), 1.14 (t, J=7.5 Hz, 3H).

Preparation of (2'S,3'R,4'S,5'S,6'R)-7-chloro-6-(4-ethylbenzyl)-2,6'-bis(hydroxymethyl)-2-methyl-3',4',5',6'-tetrahydrospiro[chroman-4,2'-pyran]-3',4',5'-triol (52)

To a solution of 51 (13 mg, 15.5 μmol) in a mixture of MeOH (1.2 mL) and THF (0.4 mL) was added Pd(OH)$_2$/C (15 mg) and 1,2-dichlorobenzene (20 μL). A balloon of hydrogen gas was attached for 0.5 h with vigorous stirring. LC/MS indicated that de-protection was complete. The reaction mixture was filtered through Celite, concentrated to a residue, and purified via preparatory TLC (5% MeOH in DCM) to give 52 (2.8 mg, 38%). $^1$H NMR (300 MHz, CD$_3$OD) δ 7.34 (s, 1H), 7.07 (s, 4H), 6.81 (s, 1H), 3.97 (s, 2H), 3.85 (dd, J=2.1, 11.1 Hz, 1H), 3.67-3.74 (m, 3H), 3.44-3.56 (m, 3H), 3.23 (t, J=9.3 Hz, 1H), 2.58 (q, J=7.5 Hz, 2H), 2.45 (d, J=15.3 Hz, 1H), 2.16 (d, J=15.6 Hz, 1H), 1.42 (s, 3H), 1.19 (t, J=7.5 Hz, 3H). LCMS m/z 479 (M+H), 501 (M+Na).

Example 9

This example illustrates the preparation of (2'S,3'R,4'S,5'S,6'R)-7-chloro-6-(4-ethylbenzyl)-6'-(hydroxymethyl)-2-methyl-3',4',5',6'-tetrahydrospiro[chroman-4,2'-pyran]-2,3',4',5'-tetraol (53) as shown in Scheme 9 (see FIG. 17).

To a solution of 45 (30 mg, 36.3 μmol) in a mixture of MeOH (3.0 mL) and THF (1 mL) was added Pd(OH)$_2$/C (30 mg). A balloon of hydrogen gas was attached for 0.5 h with vigorous stirring. LC/MS indicated that de-protection was complete. The aromatic chloride was partially cleaved. The reaction mixture was filtered through Celite, concentrated to a residue, and purified by preparatory HPLC to give 53 (5.8 mg, 34%). $^1$H NMR (300 MHz, CD$_3$OD) δ 7.50 (s, 1H), 7.00-7.07 (m, 4H), 6.77 (s, 1H), 3.98 (s, 2H), 3.93 (dd, J=2.1, 11.7 Hz, 1H), 3.65-3.82 (m, 3H), 3.55 (dd, J=8.1, 9.6 Hz, 1H), 3.27 (t, J=9.6 Hz, 1H), 2.80 (d, J=11.1 Hz, 1H), 2.57 (q, J=7.5 Hz, 2H), 1.96 (d, J=11.4 Hz, 1H), 1.68 (s, 3H), 1.19 (t, J=7.5 Hz, 3H). LC/MS m/z 447 (M−OH).

Example 10

Figure 18:
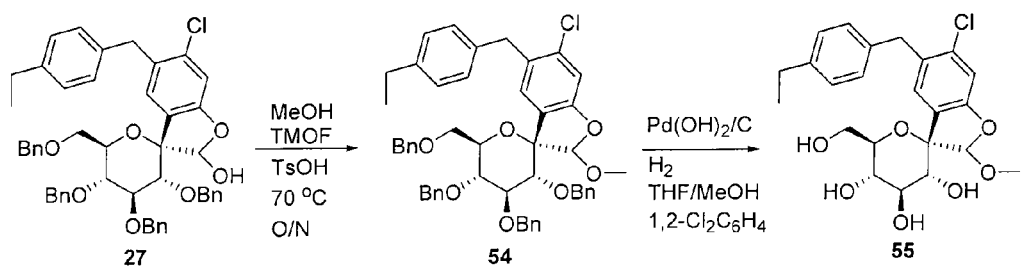
Figure 18:
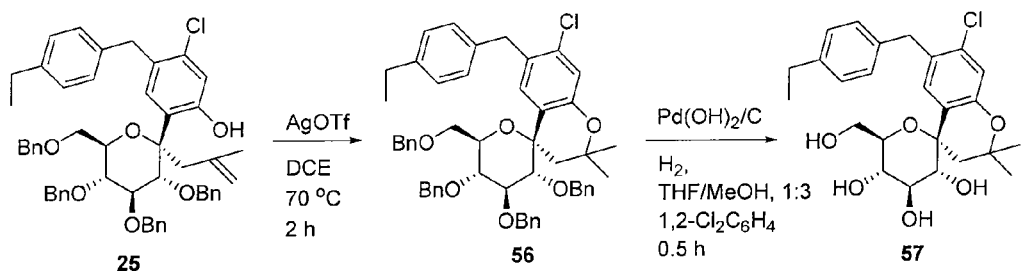

This example illustrates the preparation of compound 55 as shown in Scheme 10 (see FIG. 18).

Preparation of (2R,2'S,3'R,4'S,5'R,6'R)-3',4',5'-tris(benzyloxy)-6'-(benzyloxymethyl)-6-chloro-5-(4-ethylbenzyl)-2-methoxy-3',4',5',6'-tetrahydro-2H-spiro[benzofuran-3,2'-pyran] (54)

To a solution of 27 (35 mg, 44 μmol) in anhydrous MeOH (1 mL) and trimethylorthoformate (0.5 mL) was added 4-toluenesulfonic acid (15 mg). The mixture was heated in a closed vial at 70° C. overnight, cooled to ambient temperature, loaded onto a preparatory TLC plate, and developed using 15% EtOAc in petroleum ether to give 54 (25 mg, 70% yield). LC/MS m/z 834 (M+Na).

Preparation of (2R,2'S,3'R,4'S,5'S,6'R)-6-chloro-5-(4-ethylbenzyl)-6'-(hydroxymethyl)-2-methoxy-3',4',5',6'-tetrahydro-2H-spiro[benzofuran-3,2'-pyran]-3',4',5'-triol (55)

To a solution of 54 (22 mg, 27 μmol) in a mixture of MeOH (1.5 mL) and THF (0.5 mL) were added Pd(OH)$_2$/C (15 mg) and 1,2-dichlorobenzene (20 μL). A balloon of hydrogen gas was attached for 0.5 h with vigorous stirring. LC/MS indicated that de-protection was complete. The reaction mixture was filtered through Celite, concentrated to a residue, and purified by preparatory TLC (5% MeOH in DCM) to give 55 (9.3 mg, 76%). $^1$H NMR (300 MHz, CD$_3$OD) δ 7.20 (s, 1H), 7.06 (s, 4H), 6.82 (s, 1H), 5.61 (s, 1H), 3.99 (s, 2H), 3.63-3.79 (m, 3H), 3.55 (s, 3H), 3.42-3.60 (m, 3H), 2.57 (q, J=7.5 Hz, 2H), 1.19 (t, J=7.5 Hz, 3H). LCMS m/z 451 (M+H), 473 (M+Na).

Example 11

This example illustrates the preparation of compound 57 as outlined in Scheme 11 (see FIG. 18).

Preparation of (2'S,3'R,4'S,5'R,6'R)-3',4',5'-tris(benzyloxy)-6'-(benzyloxymethyl)-7-chloro-6-(4-ethylbenzyl)-2,2-dimethyl-3',4',5',6'-tetrahydrospiro[chroman-4,2'-pyran] (56)

A mixture of 25 (48 mg, 58 μmol) and silver triflate (15 mg, 58 μmol) in dichloroethane (1 mL) was heated to 70° C. for 2 h. LC/MS indicated that the conversion was complete to give a new and less polar component. After cooling, the mixture was loaded onto a TLC plate and developed using 10% EtOAc in petroleum ether to give 56 (19 mg, 40%). LC/MS m/z 846 (M+Na), 824 (M+1).

Preparation of (2'S,3'R,4'S,5'S,6'R)-7-chloro-6-(4-ethylbenzyl)-6'-(hydroxymethyl)-2,2-dimethyl-3',4',5',6'-tetrahydrospiro[chroman-4,2'-pyran]-3',4',5'-triol (57)

Using the same procedure for preparing 55, compound 57 (8.2 mg, 73% yield) was prepared from 56 (19 mg, 24 μmol). For 57, $^1$H NMR (300 MHz, CD$_3$OD) δ 7.37 (s, 1H), 7.07 (s, 4H), 6.76 (s, 1H), 3.97 (s, 2H), 3.76 (dd, J=1.5, 11.1 Hz, 1H), 3.53-3.67 (m, 3H), 3.47 (t, J=11.1 Hz, 1H), 3.35 (d, J=9.0 Hz, 1H), 2.58 (q, J=7.5 Hz, 2H), 2.23 (AB pattern, J=14.4 Hz, 2H), 1.43 (s, 3H), 1.31 (s, 3H), 1.19 (t, J=7.5 Hz).

Biological Example 1

The SGLT inhibitory effects of the compounds of the present invention were demonstrated by the following procedures.

Preparation of Human SGLT2 Expression Vector

A full-length cDNA clone expressing human SGLT2 (GenScript Corporation) was subcloned into Hind III and Not I sites of pEAK15 expression vector. Clones harboring the cDNA inserts were identified by restriction analysis.

Preparation of a Cell Line Stably Expressing Human SGLT2

Plasmid containing human SGLT2 was linearized with Nsi I and purified by agarose gel electrophoresis. Using Lipofectamine 2000 Transfection Reagent (Invitrogen Corporation), DNA was transfected into HEK293.ETN cells and cultured in Dulbecco's Modified Eagle Medium (DMEM) containing 10% fetal bovine serum (FBS) at 37° C. under 5% CO$_2$ for 24 h. Transfectants were selected in the same growth medium supplemented with puromycin (Invitrogen Corporation) for two weeks. Puromycin-resistant cells were recovered and seeded on a fresh 96-well plate (single cell per well) and cultured in the presence of puromycin until cells became confluent. Puromycin-resistant clones were evaluated for SGLT2 activity in the methyl-α-D-[U-$^{14}$C]glucopyranoside uptake assay described below. The clone that exhibited the highest signal-to-background ratio was used for the methyl-α-D-[U-$^{14}$C]glucopyranoside uptake assay.

Preparation of Human SGLT1 Expressing Cells

Full-length human SGLT1 cDNA on pDream2.1 expression vector was obtained from GenScript Corporation and propagated in *Escherichia coli* strain DH$_5$α using Luria-Bertani (LB) medium containing ampicillin. Plasmid DNA was isolated using the QIAGEN Plasmid Midi Kit (QIAGEN Inc.). Human SGLT1 expression plasmid DNA was transfected into COS-7 cells (American Type Culture Collection) using Lipofectamine 2000 Transfection Reagent according to a manufacturer suggested protocol. Transfected cells were stored in DMEM containing 10% dimethyl sulfoxide (DMSO) at −80° C.

Methyl-α-D-[U-$^{14}$C]glucopyranoside Uptake Assay

Cells expressing SGLT1 or SGLT2 were seeded on 96-well ScintiPlate scintillating plates (PerkinElmer, Inc.) in DMEM containing 10% FBS (1×10$^5$ cells per well in 100 μl medium) incubated at 37° C. under 5% CO$_2$ for 48 h prior to the assay. Cells were washed twice with 150 μl of either sodium buffer (137 mM NaCl, 5.4 mM KCl, 2.8 mM CaCl$_2$, 1.2 mM MgCl$_2$, 10 mM tris(hydroxymethyl)aminomethane/N-2-hydroxyethylpiperazine-N'-ethanesulfonic acid [Tris/Hepes], pH 7.2) or sodium-free buffer (137 mM N-methyl-glucamine, 5.4 mM KCl, 2.8 mM CaCl$_2$, 1.2 mM MgCl$_2$, 10 mM Tris/Hepes, pH 7.2). Test compound in 50 μl each of sodium or sodium-free buffer containing 40 μCi/ml methyl-α-D-[U-$^{14}$C] glucopyranoside (Amersham Biosciences/GE Healthcare), either with (symbols in parentheses) or without (symbols without parentheses) 25% human serum, was added per well of a 96-well plate and incubated at 37° C. with shaking for either 2 h (SGLT1 assay) or 1.5 h (SGLT2 assay). Cells were washed twice with 150 μl of wash buffer (137 mM N-methylglucamine, 10 mM Tris/Hepes, pH 7.2) and methyl-α-D-[U-$^{14}$C] glucopyranoside uptake was quantitated using a TopCount scintillation counter (PerkinElmer, Inc.). Sodium-dependent glucopyranoside uptake was measured by subtracting the values obtained with sodium-free buffer from those obtained using sodium buffer (average of triplicate determinations).

TABLE 1

| Compound | IC$_{50}$* | |
| --- | --- | --- |
| | SGLT2 | SGLT1 |
| 12 | + | ++++ |
| 20 | + | +++ |
| 30 | (+) | (+++) |
| 38 | (+) | (+++) |
| 43 | + | ++++ |
| 44 | + | ++++ |
| 47 | (+) | (++++) |
| 52 | (+) | (++++) |
| 57 | (+) | (++++) |

*Key:
+ <1 μM
++ 1 μM to <10 μM
+++ 10 μM to 100 μM
++++ >100 μM
( ) indicates incubation with 25% human serum

What is claimed is:

1. A compound having the formula:

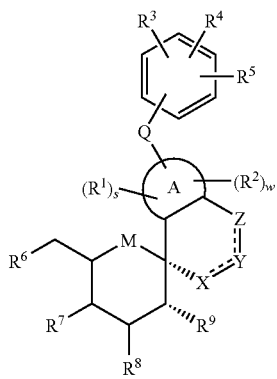

I wherein the bond between X and Y is a single bond or a double bond, and the bond between Y and Z is a single bond or a double bond; or optionally, Y represents a bond which is a single bond or a double bond covalently attaching X to Z;

the subscript s is an integer from 0 to 1;
the subscript w is an integer from 0 to 2;
M is a member selected from the group consisting of oxygen; sulfur; SO; SO$_2$; methylene optionally substituted with one to two substituents independently selected from halo, $C_1$-$C_6$ alkyl, $C_1$-$C_6$ alkoxy, $C_3$-$C_6$ cycloalkyl and $C_3$-$C_6$ cycloalkyloxy; $C_3$-$C_5$ 1,1-cycloalkylene optionally substituted with one to two substituents independently selected from halo, $C_1$-$C_6$ alkyl, $C_1$-$C_6$ alkoxy, $C_3$-$C_6$ cycloalkyl and $C_3$-$C_6$ cycloalkyloxy; and NR$^a$;

wherein in cycloalkyl portions of M, one or two methylene groups are optionally replaced independently of one another by NR$^b$, O, S, CO, SO or SO$_2$;

X is selected from the (a1) and (b1):
(a1) when Y is a single bond or when the bond between X and Y is a single bond, X is a member selected from the group consisting of oxygen; sulfur; SO; SO$_2$; NR$^c$; methylene optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; and $C_3$-$C_5$ 1,1-cycloalkylene optionally substituted with one to two substituents independently selected from halo, $C_1$-$C_6$ alkyl and $C_1$-$C_6$ alkoxy;
(b1) when Y is a double bond or when the bond between X and Y is a double bond, X is a member selected from the group consisting of N and CH, optionally substituted with a substituent selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl;

wherein in cycloalkyl groups one or two methylene groups are optionally replaced independently of one another by NR$^b$, O, S, CO, SO or SO$_2$;

when Y is other than a single bond or a double bond, Y is selected from the group consisting of (a2), (b2), (c2) and (d2):
(a2) when the bond between X and Y is a single bond and the bond between Y and Z is a single bond, Y is a member selected from the group consisting of $(CH_2)_n$; $(CH_2)_kC(O)$; $C(O)(CH_2)_k$; $C(O)NH(CH_2)_p$; $C(O)O(CH_2)_p$; $(CH_2)_mSO_2$; $SO_2(CH_2)_k$; and $(O)C(CH_2)_pC(O)$; wherein n is an integer from 1 to 3, k is an integer from 1 to 2, m is an integer from 0 to 2, p is an integer from 0 to 1, and each CH$_2$ independently may be optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl;
(b2) when the bond between X and Y is a single bond and the bond between Y and Z is a double bond, Y is a member selected from the group consisting of $(CH_2)_kCH$; $C(O)(CH_2)_pCH$; $C(O)NHCH$; $C(O)N$; $C(O)OCH$; or $SO_2(CH_2)_pCH$; wherein k is an integer from 1 to 2, p is an integer from 0 to 1, and each hydrogen independently may be optionally replaced with a substituent independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl;
(c2) when the bond between X and Y is a double bond and the bond between Y and Z is a single bond, Y is a member selected from the group consisting of $CH(CH_2)_m$; $CH(CH_2)_pC(O)$; or $CH(CH_2)_pSO_2$; wherein m is an integer from 0 to 2, p is an integer from 0 to 1, and each hydrogen independently is optionally replaced with a substituent independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; and (d2) when the bond between X and Y is a double bond and the bond, between Y and Z is a double bond, Y represents CH(CH$_2$)$_p$CH; wherein p is an integer from 0 to 1, and each hydrogen independently is optionally replaced with a substituent independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl;

wherein in cycloalkyl groups one or two methylene groups may be optionally replaced independently of one another by $NR^b$, O, S, CO, SO or $SO_2$;

Z is selected from the group consisting of (a3), (b3) and (c3):

(a3) when Y represents other than a bond, Z represents oxygen; sulfur; SO; or $NR^d$;

(b3) when Y represents a single bond, Z represents O(CH$_2$)$_m$; S(CH$_2$)$_m$; SO(CH$_2$)$_m$; or $NR^d$(CH$_2$)$_m$, wherein m is an integer from 0 to 2, and each CH$_2$ independently is optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy) $C_1$-$C_6$ alkyl; and (c3) when Y represents a double bond, Z represents N(CH$_2$)$_m$, wherein m is an integer from 0 to 2, and each CH$_2$ independently is optionally substituted with one to two substituents independently selected from halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy) $C_1$-$C_6$ alkyl;

wherein in cycloalkyl groups one or two methylene groups are optionally replaced independently of one another by $NR^b$, O, S, CO, SO or $SO_2$;

Ring A is selected from the group consisting of (a4), (b4) and (c4):

(a4) a benzene ring;

(b4) a five- or six-membered monocyclic heteroaryl ring having one or two heteroatom(s) independently selected from N, S, and O; and (c4) an eight- to ten-membered bicyclic heteroaryl ring having one to four heteroatom(s) independently selected from N, S, and O;

Q is a member selected from the group consisting of oxygen; sulfur; SO; $SO_2$; 1,1-cyclopropylene; carbonyl; or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy;

wherein in cycloalkyl groups one or two methylene groups are optionally replaced independently of one another by $NR^b$, O, S, CO, SO or $SO_2$;

$R^1$ is a member selected from the group consisting of halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy)$C_1$-$C_3$ alkyl, $C_5$-$C_{10}$ cycloalkenyl, ($C_5$-$C_{10}$ cycloalkenyl)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_1$-$C_4$ alkyl) carbonyl, aryl, heteroaryl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy; (heteroaryl)$C_1$-$C_3$ alkyloxy; $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano and nitro;

wherein alkyl, alkenyl, alkynyl, cycloalkyl and cycloalkenyl groups or portions are optionally partly or completely fluorinated or mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by $NR^b$, O, S, CO, SO or $SO_2$, and in N-heterocycloalkyl groups a methylene group is optionally replaced by CO or $SO_2$;

each $R^2$ is independently selected from the group consisting of halo, hydroxy, $C_1$-$C_4$ alkyl, $C_3$-$C_{10}$ cycloalkyl, $C_1$-$C_4$ alkyloxy, $C_3$-$C_{10}$ cycloalkyloxy, cyano and nitro, wherein alkyl groups or portions are optionally mono- or polysubstituted by fluorine, and in cycloalkyl groups one or two methylene groups are optionally replaced independently of one another by $NR^b$, O, S, CO, SO or $SO_2$;

$R^3$ is a member selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy)$C_1$-$C_3$ alkyl, $C_5$-$C_{10}$ cycloalkenyl, ($C_5$-$C_{10}$ cycloalkenyl)$C_1$-$C_3$ alkyl, ($C_1$-$C_4$ alkyloxy)$C_1$-$C_3$ alkyl, ($C_1$-$C_4$ alkylamino) $C_1$-$C_3$ alkyl, di-($C_1$-$C_3$ alkylamino)$C_1$-$C_3$ alkyl, ($C_1$-$C_4$ alkyl)carbonyl, aryl, heteroaryl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy; (heteroaryl)$C_1$-$C_3$ alkyloxy; $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_5$-$C_{10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano, nitro, ($C_1$-$C_6$ alkyloxy) $C_1$-$C_6$ alkyloxy, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl- $C_2$-$C_6$ alkynyl, tri-($C_1$-$C_4$ alkyloxy), ($C_3$-$C_7$ cycloalkyloxy)$C_2$-$C_4$ alkenyl, ($C_3$-$C_7$ cycloalkyloxy)$C_2$-$C_4$ alkynyl and ($C_3$-$C_7$ cycloalkyloxy)$C_1$-$C_3$ alkyloxy;

wherein alkyl, alkenyl, alkynyl, cycloalkyl and cycloalkenyl groups or portions are optionally partly or completely fluorinated or mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by $NR^b$, O, S, CO, SO or $SO_2$, and in N-heterocycloalkyl groups a methylene group is optionally replaced by CO or $SO_2$;

$R^4$ is a member selected from the group consisting of hydrogen, halo, hydroxy, cyano, nitro, $C_1$-$C_3$ alkyl, $C_3$-$C_{10}$ cycloalkyl, $C_1$-$C_3$ alkoxy, and methyl or methoxy substituted by 1 to 3 fluorine atoms, and in cycloalkyl groups one or two methylene groups are optionally replaced independently of one another by $NR^b$, O, S, CO, SO or $SO_2$; and optionally if $R^3$ and $R^4$ are bound to two adjacent vertices of the phenyl ring, $R^3$ and $R^4$ are optionally joined together to form a $C_3$-$C_5$ alkylene or $C_3$-$C_5$ alkenylene bridge, which is optionally partly or completely fluorinated or mono- or disubstituted by identical or different substituents selected from chlorine, hydroxy, $C_1$-$C_3$ alkoxy and $C_1$-$C_3$ alkyl, and wherein one or two methylene groups of the bridge are optionally replaced independently of one another by O, S, CO, SO, $SO_2$ or $NR^b$, and wherein one or two methyne groups are optionally replaced by an N atom;

$R^5$ is a member selected from the group consisting of hydrogen, halo, hydroxy, cyano, nitro, $C_1$-$C_3$ alkyl, $C_3$-$C_{10}$ cycloalkyl, $C_1$-$C_3$ alkoxy and methyl or methoxy substituted by 1 to 3 fluorine atoms, wherein in cycloalkyl groups one or two methylene groups are optionally replaced independently of one another by $NR^b$, O, S, CO, SO or $SO_2$;

$R^6$, $R^7$, $R^8$ and $R^9$ are each independently selected from the group consisting of hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, hydrogen, halo, $C_1$-$C_6$ alkyl, $C_2$-$C_6$ alkenyl, $C_2$-$C_6$ alkynyl, ($C_3$-$C_{10}$)cycloalkyl-($C_1$-$C_3$)alkyl, ($C_5$-$C_7$)cycloalkenyl-($C_1$-$C_3$)alkyl, aryl-($C_1$-$C_3$)alkyl, heteroaryl-($C_1$-$C_3$)alkyl, $C_1$-$C_6$ alkyloxy, $C_2$-$C_6$ alkenyloxy, $C_2$-$C_6$ alkynyloxy, ($C_3$-$C_7$)cycloalkyloxy, $C_5$-$C_7$ cycloalkenyloxy, aryloxy, heteroaryloxy, ($C_3$-$C_7$)cycloalkyl-($C_1$-$C_3$)alkyloxy, ($C_5$-$C_7$)cycloalkenyl-($C_1$-$C_3$)alkyloxy, aryl-($C_1$-$C_3$) alkyloxy, heteroaryl-($C_1$-$C_3$)alkyloxy, aminocarbonyl, hydroxycarbonyl, ($C_1$-$C_4$ alkyl)aminocarbonyl, alkyl) aminocarbonyl, ($C_1$-$C_4$ alkyloxy)carbonyl, aminocarbonyl-($C_1$-$C_3$)alkyl, ($C_1$-$C_4$)alkylaminocarbonyl-($C_1$-$C_3$)alkyl, alkyl)aminocarbonyl-($C_1$-$C_3$)alkyl, hydroxycarbonyl-($C_1$-$C_3$)alkyl, ($C_1$-$C_4$ alkyloxy)carbonyl-($C_1$-$C_3$)alkyl, ($C_3$-$C_7$)cycloalkyloxy-($C_1$-$C_3$)alkyl, ($C_5$-$C_7$)cycloalkenyloxy-($C_1$-$C_3$)alkyl, aryloxy-($C_1$-$C_3$)alkyl, heteroaryloxy-($C_1$-$C_3$)alkyl, $C_1$-$C_4$ alkylsulfonyloxy, arylsulfonyloxy, aryl-($C_1$-$C_3$)alkyl-sulfonyloxy, trimethylsilyloxy, t-butyldimethylsilyloxy and cyano;

wherein alkyl, alkenyl, alkynyl, cycloalkyl and cycloalkenyl groups or portions are optionally partly or completely fluorinated or mono- or disubstituted by identical or different substituents selected from chlorine, hydroxy, $C_1$-$C_3$ alkoxy and $C_1$-$C_3$ alkyl, and in cycloalkyl and cycloalkenyl groups one or two methylene groups are optionally replaced independently of one another by $NR^b$, O, S, CO, SO or $SO_2$;

each $R^a$, $R^b$ and $R^c$ is independently selected from the group consisting of H, $C_1$-$C_6$ alkyl, $C_3$-$C_6$ cycloalkyl and ($C_1$-$C_4$ alkyl)carbonyl, wherein the alkyl groups are optionally partly or completely fluorinated;

$R^d$ is a member selected from the group consisting of H, $C_1$-$C_6$ alkyl, ($C_1$-$C_4$ alkyl)carbonyl, $CHR^eR^f$, $SO_2R^e$, $C(O)OR^e$ and $C(O)NR^eR^f$, wherein the alkyl groups are optionally partly or completely fluorinated; and $R^e$ and $R^f$ are each independently selected from the group consisting of H and $C_1$-$C_6$ alkyl, wherein the alkyl groups are optionally partly or completely fluorinated; and pharmaceutically acceptable salts thereof.

2. A compound of claim 1, wherein s is 0.

3. A compound of claim 1, wherein w is 0.

4. A compound of claim 1, wherein M is oxygen or sulfur.

5. A compound of claim 1, wherein M is oxygen.

6. A compound of claim 1, wherein X is methylene, optionally substituted with one to two substituents independently selected from the group consisting of halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; Y is a single bond; and Z is a member selected from the group consisting of $O(CH_2)_m$, $S(CH_2)_m$, $SO(CH_2)_m$ and $NR^d(CH_2)_m$.

7. A compound of claim 1, wherein X is methylene optionally substituted with one to two substituents independently selected from the group consisting of halo, hydroxy, $C_1$-$C_6$ alkyl, $C_1$-$C_6$ alkoxy, $C_3$-$C_6$ cycloalkyl, $C_3$-$C_6$ cycloalkyloxy and ($C_1$-$C_6$ alkoxy)$C_1$-$C_6$ alkyl; Y is $(CH_2)_n$; and Z is selected from the group consisting of oxygen, sulfur, SO and $NR^d$.

8. A compound of claim 1, wherein X is methylene; Y is a single bond; and Z is $O(CH_2)_m$.

9. A compound of claim 1, wherein X is methylene; Y is $(CH_2)_n$; and Z is oxygen.

10. A compound of claim 1, wherein ring A is a benzene ring or a five- or six-membered monocyclic heteroaryl ring having one or two heteroatom(s) independently selected from N, S and O.

11. A compound of claim 1, wherein ring A is a benzene ring.

12. A compound of claim 1, wherein Q is selected from the group consisting of oxygen, sulfur, and methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy.

13. A compound of claim 1, wherein Q is methylene.

14. A compound of claim 1, wherein $R^1$ is selected from the group consisting of halo, $C_1$-$C_6$ alkyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano and nitro, wherein alkyl and cycloalkyl groups or portions are optionally partly or completely fluorinated.

15. A compound of claim 1, wherein $R^1$ is selected from the group consisting of halo and $C_1$-$C_6$ alkyl.

16. A compound of claim 1, wherein $R^2$ is selected from the group consisting of halo, $C_1$-$C_4$ alkyl and $C_1$-$C_4$ alkyloxy.

17. A compound of claim 1, wherein $R^2$ is halo.

18. A compound of claim 1, wherein $R^3$ is selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_3$-$C_{10}$ cycloalkyloxy)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, $C_1$-$C_6$ alkyloxy, $C_3$-$C_{10}$ cycloalkyloxy, hydroxy, cyano and nitro, wherein alkyl and cycloalkyl groups or portions are optionally partly or completely fluorinated, and wherein in cycloalkyl groups one or two methylene groups are optionally replaced independently of one another by $NR^b$, O, S, CO, SO or $SO_2$.

19. A compound of claim 1, wherein $R^3$ is selected from the group consisting of hydrogen, halo, $C_1$-$C_6$ alkyl, $C_2$-$C_6$ alkenyl, $C_2$-$C_6$ alkynyl, $C_1$-$C_6$ alkyloxy, $C_3$-$C_{10}$ cycloalkyl and $C_3$-$C_{10}$ cycloalkyloxy, wherein alkyl and cycloalkyl groups or portions are optionally partly or completely fluorinated, and in cycloalkyl groups a methylene group is optionally replaced by $NR^b$, O, S, CO, SO or $SO_2$.

20. A compound of claim 1, wherein $R^4$ and $R^5$ are each independently selected from the group consisting of hydrogen, halo, $C_1$-$C_3$ alkyl, $C_3$-$C_{10}$ cycloalkyl and $C_1$-$C_3$ alkoxy.

21. A compound of claim 1, wherein $R^4$ and $R^5$ are each independently selected from the group consisting of hydrogen and halo.

22. A compound of claim 1, wherein $R^6$, $R^7$, $R^8$ and $R^9$ are each independently selected from the group consisting of hydroxy, halo, $C_1$-$C_6$ alkyl, $C_1$-$C_6$ alkyloxy, ($C_3$-$C_7$)cycloalkyloxy, or ($C_3$-$C_7$)cycloalkyl-($C_1$-$C_3$)alkyloxy, wherein alkyl and cycloalkyl groups or portions are optionally partly or completely fluorinated.

23. A compound of claim 1, wherein $R^6$, $R^7$, $R^8$ and $R^9$ are each hydroxy.

24. A compound of claim 1, selected from the group consisting of:
- (2'S,3'R,4'S,5'S,6'R)-6-(4-ethylbenzyl)-6'-(hydroxymethyl)-3',4',5',6'-tetrahydrospiro[chroman-4,2'-pyran]-3',4',5'-triol (12);
- (2'S,3'R,4'S,5'S,6'R)-7-chloro-6-(4-ethylbenzyl)-6'-(hydroxymethyl)-3',4',5',6'-tetrahydrospiro[chroman-4,2'-pyran]-3',4',5'-triol (20);
- (2'R,3'R,4'S,5'S,6'R)-6-chloro-5-(4-ethylbenzyl)-6'-(hydroxymethyl)-3',4',5',6'-tetrahydro-2H-spiro[benzofuran-3,2'-pyran]-3',4',5'-triol (30);
- (2'S,3'R,4'S,5'S,6'R)-8-chloro-7-(4-ethylbenzyl)-6'-(hydroxymethyl)-3,3',4,4',5',6'-hexahydro-2H-spiro[benzo[b]oxepine-5,2'-pyran]-3',4',5'-triol (38);
- (2'S,3'R,4'S,5'S,6'R)-7-chloro-6-(4-ethylbenzyl)-6'-(hydroxymethyl)-2-methoxy-3',4',5',6'-tetrahydrospiro[chroman-4,2'-pyran]-3',4',5'-triol (43);
- (2'S,3'R,4'S,5'S,6'R)-7-chloro-6-(4-ethylbenzyl)-6'-(hydroxymethyl)-3',4',5',6'-tetrahydrospiro[chroman-4,2'-pyran]-2,3',4',5'-tetraol (44);
- (2'S,3'R,4'S,5'S,6'R)-7-chloro-6-(4-ethylbenzyl)-6'-(hydroxymethyl)-2-methyl-3',4',5',6'-tetrahydrospiro[chroman-4,2'-pyran]-3',4',5'-triol (47);
- (2'S,3'R,4'S,5'S,6'R)-7-chloro-6-(4-ethylbenzyl)-2,6'-bis(hydroxymethyl)-2-methyl-3',4',5',6'-tetrahydrospiro[chroman-4,2'-pyran]-3',4',5'-triol (52);
- (2'S,3'R,4'S,5'S,6'R)-7-chloro-6-(4-ethylbenzyl)-6'-(hydroxymethyl)-2,2-dimethyl-3',4',5',6'-tetrahydrospiro[chroman-4,2'-pyran]-3',4',5'-triol (57).

25. A pharmaceutical composition comprising a pharmaceutically acceptable excipient and a compound of any one of claims 1-3 and 4-24.

26. A method of treating a disease or condition mediated by SGLT, said method comprising administering to a subject having said disease or condition a therapeutically effective amount of a compound of any one of claims 1-3 and 4-24.

27. A method of retarding or reversing the progress of, or alleviating obesity, said method comprising administering to a subject in need thereof a therapeutically effective amount of a compound of claim 1.

28. A method of delaying the onset of, retarding or reversing the progress of, or alleviating diabetes, said method comprising administering to a subject in need thereof a therapeutically effective amount of a compound of claim 1.

29. A method in accordance with claim 28, wherein said diabetes is type 1 diabetes.

30. A method in accordance with claim 28, wherein said diabetes is type 2 diabetes.

31. A method in accordance with claim 28, wherein said compound in administered in combination with a second therapeutic agent.

32. A method in accordance with claim 31, wherein said second therapeutic agent is selected from antidiabetic agents, lipid-lowering/lipid-modulating agents, agents for treating diabetic complications, anti-obesity agents, antihypertensive agents, antihyperuricemic agents, and agents for treating chronic heart failure or atherosclerosis.

33. A method of preparing compounds of claim 1, wherein the portion

is selected from the group consisting of —$CH_2O$—, —$CH_2CH_2O$— and —$CH_2CH_2CH_2O$—, M is oxygen and ring A is benzene, said method comprising:

(i) coupling a phenol intermediate having the formula:

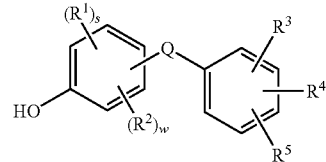

with a suitable sugar derivative to form a framework intermediate having formula IIa:

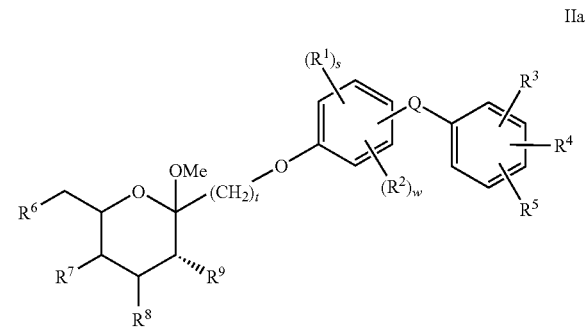

wherein the subscript t is an integer of from 1 to 3; and (ii) cyclizing said framework intermediate to form said compound having the formula:

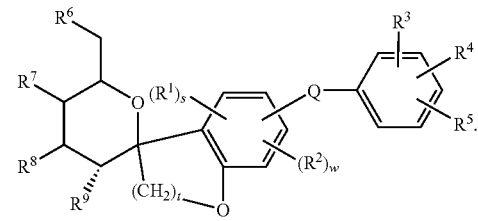

34. A method in accordance with claim 33, wherein said cyclizing is carried out in the presence of a Lewis acid catalyst.

35. A method in accordance with claim 33, wherein the subscript t is 1.

36. A method in accordance with claim 33, wherein the subscript t is 2.

37. A method in accordance with claim 33, wherein the subscript t is 3.

38. A method of preparing compounds of claim 1, wherein the portion

is selected from the group consisting of —CH$_2$O—, —CH$_2$CH$_2$O—, —CH$_2$CH(OH)O—, —CH$_2$CH(CH$_3$)O—, —CH$_2$CH(OCH$_3$)O—, and —CH$_2$CH$_2$CH$_2$O—, M is oxygen and ring A is benzene, said method comprising:

(i) coupling an intermediate having the formula:

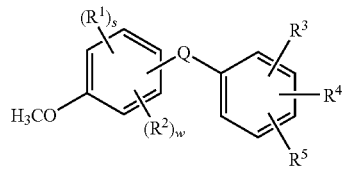

with a suitable sugar derivative to form a framework intermediate having formula:

IId

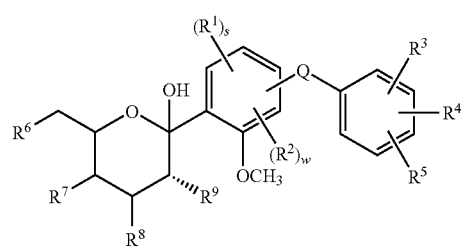

(ii) coupling an allyl or methallyl component to the C1-position of the sugar portion to produce an intermediate having the formula:

IIe

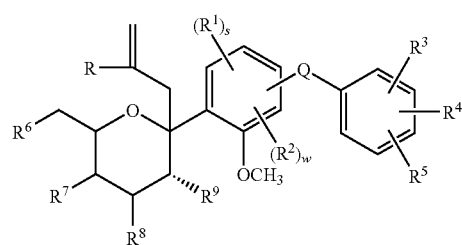

wherein R is H or CH$_3$;

(iii) converting said framework intermediate to said compound having the formula:

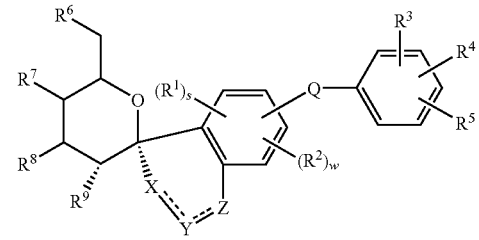

through one or more steps utilizing ether cleavage, ozonolysis, hydroboration or epoxidation.

39. A method in accordance with claim 38, wherein step (iii) utilizes ozonolysis.

40. A method of preparing compounds of claim 1, wherein the portion

is selected from the group consisting of —CH$_2$OCH$_2$—, and —CH$_2$CH$_2$OCH$_2$—, M is oxygen and ring A is benzene, said method comprising:

(i) coupling a benzylic alcohol intermediate having the formula:

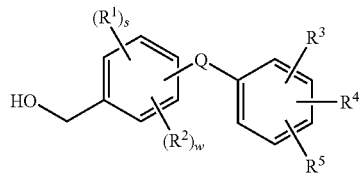

with a suitable sugar derivative to form a framework intermediate having formula IIc:

IIc

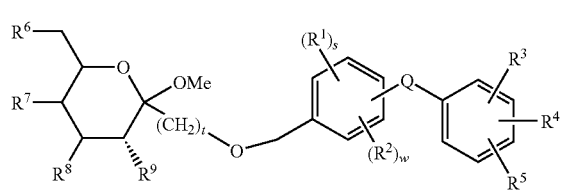

wherein the subscript t is an integer of from 1 to 3; and (ii) cyclizing said framework intermediate to form said compound having the formula:

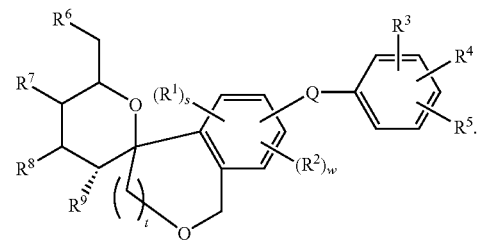

41. An intermediate compound having a formula selected from the group consisting of IIa, IIb and IIc:

IIa

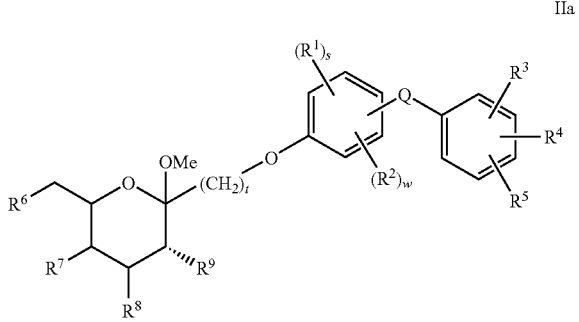

-continued

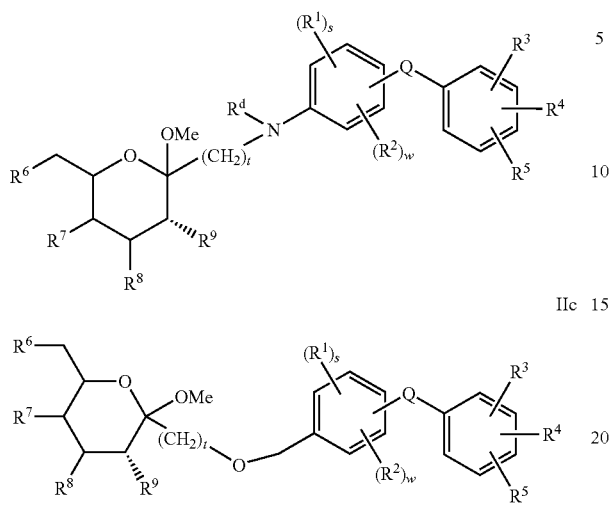

wherein
the subscript t is an integer from 1 to 3 if formula IIa, an integer of from 2 to 3 in formula IIb and an integer of from 1 to 2 in formula IIc;
the subscript s is an integer from 0 to 1;
the subscript w is an integer from 0 to 2;
Q is a member selected from the group consisting of oxygen; sulfur; SO; $SO_2$; 1,1-cyclopropylene; carbonyl; or methylene optionally substituted with one to two substituents independently selected from halo, hydroxy, $C_1$-$C_6$ alkyl, $C_1$-$C_6$ alkoxy, $C_3$-$C_6$ cycloalkyl and $C_3$-$C_6$ cycloalkyloxy;
wherein in cycloalkyl groups or portions one or two methylene groups are optionally replaced independently of one another by $NR^b$, O, S, CO, SO or $SO_2$;
$R^1$ is a member selected from the group consisting of halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy)$C_1$-$C_3$ alkyl, $C_5$-$C_{10}$ cycloalkenyl, ($C_5$-$C_{10}$ cycloalkenyl)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_1$-$C_4$ alkyl)carbonyl, aryl, heteroaryl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy; (heteroaryl)$C_1$-$C_3$ alkyloxy; $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_{5-10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano and nitro;
wherein alkyl, alkenyl, alkynyl, cycloalkyl and cycloalkenyl groups or portions are optionally partly or completely fluorinated or mono- or disubstituted by identical or different substituents selected from chlorine, hydroxy, $C_1$-$C_3$ alkoxy and $C_1$-$C_3$ alkyl, and
in cycloalkyl and cycloalkenyl groups or portions one or two methylene groups are optionally replaced independently of one another by $NR^b$, O, S, CO, SO or $SO_2$, and
in N-heterocycloalkyl groups or portions a methylene group is optionally replaced by CO or $SO_2$;
each $R^2$ is independently selected from the group consisting of halo, hydroxy, $C_1$-$C_4$ alkyl, $C_3$-$C_{10}$ cycloalkyl, $C_1$-$C_4$ alkyloxy, $C_3$-$C_{10}$ cycloalkyloxy, cyano and nitro, wherein alkyl groups are optionally mono- or polysubstituted by fluorine, and in cycloalkyl groups one or two methylene groups are optionally replaced independently of one another by $NR^b$, O, S, CO, SO or $SO_2$;
$R^3$ is a member selected from the group consisting of hydrogen, halo, $C_1$-$C_6$ alkyl, $C_2$-$C_6$ alkenyl, $C_2$-$C_6$ alkynyl, $C_3$-$C_{10}$ cycloalkyl, ($C_3$-$C_{10}$ cycloalkyl)$C_1$-$C_3$ alkyl, ($C_2$-$C_4$ alkenyl)$C_1$-$C_3$ alkyloxy, ($C_2$-$C_4$ alkynyl)$C_1$-$C_3$ alkyloxy, ($C_3$-$C_{10}$ cycloalkyl)$C_2$-$C_4$ alkenyl, $C_3$-$C_6$ cycloalkylidenmethyl, ($C_3$-$C_{10}$ cycloalkyloxy)$C_1$-$C_3$ alkyl, $C_5$-$C_{10}$ cycloalkenyl, ($C_5$-$C_{10}$ cycloalkenyl)$C_1$-$C_3$ alkyl, ($C_1$-$C_4$ alkyloxy)$C_1$-$C_3$ alkyl, ($C_1$-$C_4$ alkylamino)$C_1$-$C_3$ alkyl, di-($C_1$-$C_3$ alkylamino)$C_1$-$C_3$ alkyl, ($C_1$-$C_4$ alkyl)carbonyl, aryl, heteroaryl, arylcarbonyl, heteroarylcarbonyl, aminocarbonyl, ($C_1$-$C_4$ alkyl)aminocarbonyl, di-($C_1$-$C_3$ alkyl)aminocarbonyl, hydroxycarbonyl, pyrrolidin-1-ylcarbonyl, piperidin-1-ylcarbonyl, morpholin-4-ylcarbonyl, piperazin-1-ylcarbonyl, 4-($C_1$-$C_4$ alkyl)piperazin-1-ylcarbonyl, ($C_1$-$C_4$ alkyloxy)carbonyl, amino, $C_1$-$C_4$ alkylamino, di-($C_1$-$C_3$ alkyl)amino, pyrrolidin-1-yl, piperidin-1-yl, morpholin-4-yl, piperazin-1-yl, 4-($C_1$-$C_4$ alkyl)piperazin-1-yl, ($C_1$-$C_4$ alkyl)carbonylamino, arylcarbonylamino, $C_1$-$C_4$ alkylsulfonylamino, arylsulfonylamino, heteroarylcarbonylamino, $C_1$-$C_6$ alkyloxy, $C_3$-$C_{10}$ cycloalkyloxy, $C_5$-$C_7$ cycloalkenyloxy, aryloxy, heteroaryloxy, (aryl)$C_1$-$C_3$ alkyloxy; (heteroaryl)$C_1$-$C_3$ alkyloxy; $C_1$-$C_4$ alkylsulfanyl, $C_1$-$C_4$ alkylsulfinyl, $C_1$-$C_4$ alkylsulfonyl, $C_3$-$C_{10}$ cycloalkylsulfanyl, $C_3$-$C_{10}$ cycloalkylsulfinyl, $C_3$-$C_{10}$ cycloalkylsulfonyl, $C_{5-10}$ cycloalkenylsulfanyl, $C_5$-$C_{10}$ cycloalkenylsulfinyl, $C_5$-$C_{10}$ cycloalkenylsulfonyl, arylsulfanyl, arylsulfinyl, arylsulfonyl, hydroxy, cyano, nitro, ($C_1$-$C_6$ alkyloxy)$C_1$-$C_6$ alkyloxy, tri-($C_1$-$C_4$ alkyl)silyl-$C_1$-$C_6$ alkyl, tri-($C_1$-$C_4$ alkyl)silyl-$C_2$-$C_6$ alkenyl, tri-($C_1$-$C_4$ alkyl)silyl-$C_2$-$C_6$ alkynyl, tri-($C_1$-$C_4$ alkyl)silyl-$C_1$-$C_6$ alkyloxy, ($C_3$-$C_7$ cycloalkyloxy)$C_2$-$C_4$ alkenyl, ($C_3$-$C_7$ cycloalkyloxy)$C_2$-$C_4$ alkynyl and ($C_3$-$C_7$ cycloalkyloxy)$C_1$-$C_3$ alkyloxy;
wherein alkyl, alkenyl, alkynyl, cycloalkyl and cycloalkenyl groups are optionally partly or completely fluorinated or mono- or disubstituted by identical or different substituents selected from chlorine, hydroxy, $C_1$-$C_3$ alkoxy and $C_1$-$C_3$ alkyl, and
in cycloalkyl and cycloalkenyl groups one or two methylene groups are optionally replaced independently of one another by $NR^b$, O, S, CO, SO or $SO_2$, and
in N-heterocycloalkyl groups a methylene group is optionally replaced by CO or $SO_2$;
$R^4$ is a member selected from the group consisting of hydrogen, halo, hydroxy, cyano, nitro, $C_1$-$C_3$ alkyl, $C_3$-$C_{10}$ cycloalkyl, $C_1$-$C_3$ alkoxy, and methyl or methoxy substituted by 1 to 3 fluorine atoms, and in cycloalkyl groups one or two methylene groups are optionally replaced independently of one another by $NR^b$, O, S, CO, SO or $SO_2$; and optionally if $R^3$ and $R^4$ are bound to two adjacent vertices of the phenyl ring, $R^3$ and $R^4$ are optionally joined together to form a $C_3$-$C_5$ alkylene or $C_3$-$C_5$ alkenylene bridge, which is optionally partly or completely fluorinated or mono- or disubstituted by identical or different substituents selected from chlorine, hydroxy, $C_1$-$C_3$ alkoxy and $C_1$-$C_3$ alkyl, and wherein one or two methylene groups of the bridge are optionally replaced independently of one another by O, S, CO, SO, $SO_2$ or $NR^b$, and wherein one or two methyne groups are optionally replaced by an N atom;

$R^5$ is a member selected from the group consisting of hydrogen, halo, hydroxy, cyano, nitro, $C_1$-$C_3$ alkyl, $C_3$-$C_{10}$ cycloalkyl, $C_1$-$C_3$ alkoxy and methyl or methoxy substituted by 1 to 3 fluorine atoms, wherein in cycloalkyl groups one or two methylene groups are optionally replaced independently of one another by $NR^b$, O, S, CO, SO or $SO_2$;

$R^6$, $R^7$, $R^8$ and $R^9$ are each independently selected from the group consisting of hydroxy, ($C_1$-$C_{18}$ alkyl)carbonyloxy, ($C_1$-$C_{18}$ alkyl)oxycarbonyloxy, arylcarbonyloxy, aryl-($C_1$-$C_3$ alkyl)carbonyloxy, hydrogen, halo, $C_1$-$C_6$ alkyl, $C_2$-$C_6$ alkenyl, $C_2$-$C_6$ alkynyl, ($C_3$-$C_{10}$)cycloalkyl-($C_1$-$C_3$)alkyl, ($C_5$-$C_7$)cycloalkenyl-($C_1$-$C_3$)alkyl, aryl-($C_1$-$C_3$)alkyl, heteroaryl-($C_1$-$C_3$)alkyl, $C_1$-$C_6$ alkyloxy, $C_2$-$C_6$ alkenyloxy, $C_2$-$C_6$ alkynyloxy, ($C_3$-$C_7$)cycloalkyloxy, $C_5$-$C_7$ cycloalkenyloxy, aryloxy, heteroaryloxy, ($C_3$-$C_7$)cycloalkyl-($C_1$-$C_3$)alkyloxy, ($C_5$-$C_7$)cycloalkenyl-($C_1$-$C_3$)alkyloxy, aryl-($C_1$-$C_3$) alkyloxy, heteroaryl-($C_1$-$C_3$)alkyloxy, aminocarbonyl, hydroxycarbonyl, ($C_1$-$C_4$ alkyl)alkylaminocarbonyl, di-($C_1$-$C_3$ alkyl)aminocarbonyl, ($C_1$-$C_4$ alkyloxy)carbonyl, aminocarbonyl-($C_1$-$C_3$)alkyl, ($C_1$-$C_4$)alkylaminocarbonyl-($C_1$-$C_3$)alkyl, di-($C_1$-$C_3$ alkyl)aminocarbonyl-($C_1$-$C_3$)alkyl, hydroxycarbonyl-($C_1$-$C_3$)alkyl, ($C_1$-$C_4$ alkyloxy)carbonyl-($C_1$-$C_3$)alkyl, ($C_3$-$C_7$)cycloalkyloxy-($C_1$-$C_3$)alkyl, ($C_5$-$C_7$) cycloalkenyloxy-($C_1$-$C_3$)alkyl, aryloxy-($C_1$-$C_3$)alkyl, heteroaryloxy-($C_1$-$C_3$)alkyl, $C_1$-$C_4$ alkylsulfonyloxy, arylsulfonyloxy, aryl-($C_1$-$C_3$)alkyl-sulfonyloxy, trimethylsilyloxy, t-butyldimethylsilyloxy and cyano;

wherein alkyl, alkenyl, alkynyl, cycloalkyl and cycloalkenyl groups or portions are optionally partly or completely fluorinated or mono- or disubstituted by identical or different substituents selected from chlorine, hydroxy, $C_1$-$C_3$ alkoxy and $C_1$-$C_3$ alkyl, and in cycloalkyl and cycloalkenyl groups or portions one or two methylene groups are optionally replaced independently of one another by $NR^b$, O, S, CO, SO or $SO_2$;

each $R^b$ is independently selected from the group consisting of H, $C_1$-$C_6$ alkyl, $C_3$-$C_6$ cycloalkyl and ($C_1$-$C_4$ alkyl)carbonyl, wherein the alkyl groups are optionally partly or completely fluorinated;

$R^d$ is a member selected from the group consisting of H, $C_1$-$C_6$ alkyl, ($C_1$-$C_4$ alkyl)carbonyl, $CHR^eR^f$, $SO_2R^e$, $C(O)OR^e$ and $C(O)NR^eR^f$, wherein the alkyl groups are optionally partly or completely fluorinated; and $R^e$ and $R^f$ are each independently selected from the group consisting of H and $C_1$-$C_6$ alkyl, wherein the alkyl groups are optionally partly or completely fluorinated;

and pharmaceutically acceptable salts thereof.

* * * * *

UNITED STATES PATENT AND TRADEMARK OFFICE
CERTIFICATE OF CORRECTION

PATENT NO. : 7,795,228 B2  Page 1 of 1
APPLICATION NO. : 11/964493
DATED : September 14, 2010
INVENTOR(S) : Hadd et al.

It is certified that error appears in the above-identified patent and that said Letters Patent is hereby corrected as shown below:

In the Claims:

Column 56, Claim 1, Line 17: please delete the second "arylsulfanyl" and replace it with -- arylsulfinyl --

Column 57, Claim 1, Line 1: please insert -- alkyl)silyl-$C_1$-$C_6$ -- after -- tri-($C_1$-$C_4$ --

Column 57, Claim 1, Line 50: please insert -- di-($C_1$-$C_3$ -- after -- aminocarbonyl, --

Column 57, Claim 1, Line 53: please insert -- di-($C_1$-$C_3$ -- after -- $C_3$)alkyl, --

Column 64, Claim 41, Line 1: please delete the second "arylsulfanyl" and replace it with -- arylsulfinyl --

Signed and Sealed this
Eighth Day of February, 2011

David J. Kappos
*Director of the United States Patent and Trademark Office*